United States Patent
Thatcher et al.

(10) Patent No.: US 8,957,086 B2
(45) Date of Patent: Feb. 17, 2015

(54) COMPOUNDS AND METHODS OF TREATING BRAIN DISORDERS

(75) Inventors: Gregory R. J. Thatcher, Chicago, IL (US); Zhihui Qin, Chicago, IL (US); Jia Luo, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 13/695,731

(22) PCT Filed: May 4, 2011

(86) PCT No.: PCT/US2011/035155
§ 371 (c)(1),
(2), (4) Date: Feb. 5, 2013

(87) PCT Pub. No.: WO2011/140198
PCT Pub. Date: Nov. 10, 2011

(65) Prior Publication Data
US 2013/0131099 A1    May 23, 2013

Related U.S. Application Data

(60) Provisional application No. 61/331,483, filed on May 5, 2010, provisional application No. 61/371,356, filed on Aug. 6, 2010, provisional application No. 61/376,411, filed on Aug. 24, 2010.

(51) Int. Cl.
| | | |
|---|---|---|
| A01N 43/42 | (2006.01) |
| A61K 31/44 | (2006.01) |
| A01N 43/78 | (2006.01) |
| A61K 31/425 | (2006.01) |
| C07D 471/04 | (2006.01) |
| C07D 277/22 | (2006.01) |
| C07D 277/24 | (2006.01) |
| C07D 277/28 | (2006.01) |
| C07D 277/32 | (2006.01) |
| C07D 277/56 | (2006.01) |
| C07D 277/587 | (2006.01) |
| C07D 417/06 | (2006.01) |
| C07D 417/14 | (2006.01) |

(52) U.S. Cl.
CPC ............ *C07D 471/04* (2013.01); *C07D 277/22* (2013.01); *C07D 277/24* (2013.01); *C07D 277/28* (2013.01); *C07D 277/32* (2013.01); *C07D 277/56* (2013.01); *C07D 277/587* (2013.01); *C07D 417/06* (2013.01); *C07D 417/14* (2013.01)
USPC ......................................... 514/292; 514/365

(58) Field of Classification Search
None
See application file for complete search history.

(56) References Cited

U.S. PATENT DOCUMENTS

| | | | |
|---|---|---|---|
| 5,712,299 A | 1/1998 | Boar et al. | |
| 6,310,052 B1 * | 10/2001 | Thatcher et al. | 514/509 |
| 6,579,871 B2 | 6/2003 | Panetta et al. | |
| 7,115,661 B1 * | 10/2006 | Thatcher et al. | 514/509 |
| 2005/0137191 A1 | 6/2005 | Thatcher et al. | |
| 2008/0233163 A1 | 9/2008 | Assaf | |

FOREIGN PATENT DOCUMENTS

| | | |
|---|---|---|
| CA | 2683882 A1 | 10/2008 |
| WO | WO-2004/076424 A1 | 9/2004 |
| WO | WO-2005/105065 A2 | 11/2005 |

OTHER PUBLICATIONS

CAS RN: 294191-00-7 (entered Oct. 10, 2000).*
STN CAS RN: 294191-00-7 (entered STN Oct. 2000).*
Abe, K., et al., "Effects of S-8510, a Novel Benzodiazepine Receptor Partial Inverse Agonist, on Basal Forebrain Lesioning-Induced Dysfunction in Rats," *Eur. J. Pharmacol.* 347 (1998) 145-152.
Arancio, O., et al.,"Activity-Dependent Long-Term Enhancement of Transmitter Release by Presynaptic 3',5'-Cyclic GMP in Cultured Hippocampal Neurons," *Nature* 376 (1995) 74-80.
Barger, S.W., et al., "Role of Cyclic GMP in the Regulation of Neuronal Calcium and Survival by Secreted Forms of β-Amyloid Precursor," *J. Neurochem.* 64 (1995) 2087-2096.
Beninger, Richard J., et al.,"Subchronic MK-801 Behavioural Deficits in Rats: Partial Reversal by the Novel Nitrate GT 1061," *Pharmacology, Biochemistry and Behavior*, 2009, vol. 91, No. 4, pp. 495-502.
Bennett, Brian M., et al., "Cognitive Deficits in Rats After Forebrain Cholinergic Depletion are Reversed by a Novel NO Mimetic Nitrate Ester," *Neuropsychopharmacology*, 2007, vol. 32, No. 3, pp. 505-513.
Berge, S.M., et al, "Pharmaceutical Salts," *J. Pharm. Sci.* 66 (1977) 1-19.
Bernabeu, R., et al., "Further Evidence for the Involvement of a Hippocampal cGMP/cGMP-Dependent Protein Kinase Cascade in Memory Consolidation," *NeuroReport* 8 (1997) 2221-2224.
Bernabeu, R., et al., "Hippocampal cGMP and cAMP are Differentially Involved in Memory Processing of Inhibitory Avoidance Learning," *NeuroReport* 7 (1996) 585-588.

(Continued)

*Primary Examiner* — Craig Ricci
*Assistant Examiner* — Jared D Barsky
(74) *Attorney, Agent, or Firm* — Marshall, Gerstein & Borun LLP

(57) ABSTRACT

Nitrated and non-nitrated compounds capable of protecting brain tissue from injury and useful as therapeutic agents to treat neurodegenerative diseases and conditions are disclosed. Methods of using the compounds in therapeutic treatments, and methods of preparing the compounds, also are disclosed.

7 Claims, 4 Drawing Sheets

(56) References Cited

OTHER PUBLICATIONS

Bloeman, P. G., et al., "Adhesion Molecules: a New Target for Immunoliposome-Mediated Drug Delivery," *FEBS Lett.* 357 (1995) 140.

Briscoe, P., et al., "Delivery of Superoxide Dismutase to Pulmonary Epithelium Via pH-Sensitive Liposomes," *Am. J. Physiol.* 1233 (1995) 134.

Bullock, R., et al., "Factors Affecting Excitatory Amino Acid Release Following Severe Human Head Injury," *J. Neurosurg.* 89 (1998) 507-518.

Chan, P. H., et al., "Overexpression of SOD1 in Transgenic Rats Protects Vulnerable Neurons Against Ischemic Damage After Global Cerebral Ischemia and Reperfusion," *J. Neurosci.* 18 (1998) 8292-8299.

Chen, J., et al., "Induction of Caspase-3-Like Protease May Mediate Delayed Neuronal Death in the Hippocampus after Transient Cerebral Ischemia," *J. Neurosci.* 18 (1998) 4914-4928.

Cohen, G. M., et al., "Caspases: the executioners of apoptosis," *Biochem. J.* 326 (1997) 1-16.

Du, Y., et al., "Activation of a Caspase 3-Related Cysteine Protease is Required for Glutamate-Mediated Apoptosis of Cultured Cerebellar Granule Neurons," *Proc. Natl. Acad. Sci. USA* 94 (1997) 11657-11662.

Endres, M., et al., "Attenuation of Delayed Neuronal Death After Mild Focal Ischemia in Mice by Inhibition of the Caspase Family," *J. Cereb. Blood Flow Metab.* 18 (1998) 238-247.

Estevez, A. G., et al., "Nitric Oxide-Dependent Production of cGMP Supports the Survival of Rat Embryonic Motor Neurons Cultured with Brain-Derived Neurotrophic Factor," *J. Neurosci.* 18 (1998) 3708-3714.

Farinelli, S. E., et al, "Nitric Oxide Delays the Death of Trophic Factor-Deprived PC12 Cells and Sympathetic Neurons by a cGMP-Mediated Mechanism," *J. Neurosci.* 16 (1996) 2325-2334.

Furukawa, K., et al., "Activation of K+ Channels and Suppression of Neuronal Activity by Secreted β-Amyloid-Precursor Protein," *Nature* 379 (1996) 74-78.

Gaetani, P., et al., "Oxidative Stress in the Human Brain After Subarachnoid Hemorrhage," *J. Neurosurg.* 89 (1998) 748-754.

Goda, H., et al., "Modulation of Ischemia-Evoked Release of Excitatory and Inhibitory Amino Acids by Adenosine A1 Receptor Agonist," *Eur. J. Pharmacol.* 357 (1998) 149-155.

Gottron, F. J., et al., "Caspase Inhibition Selectively Reduces the Apoptotic Component of Oxygen-Glucose Deprivation-Induced Cortical Neuronal Cell Death," *Mol. Cell. Neurosci.* 9 (1997) 159-169.

Haviv, R., et al., "Need for Caspases in Apoptosis of Trophic Factor-Deprived PC12 Cells," *J. Neurosci. Res.* 50 (1997) 69-80.

Huang, F. P., et al., "Effects of Mild Hypothermia on the Release of Regional Glutamate and Glycine During Extended Transient Focal Cerebral Ischemia in Rats," *Neurochem. Res.* 23 (1998) 991-996.

Ibarrola, D., et al, "The Effect of Eliprodil on the Evolution of a Focal Cerebral Ischaemia in Vivo," *Eur. J. Pharmacol.* 352 (1998) 29-35.

International Search Report in international application No. PCT/US2011/035155, dated Jan. 5, 2013.

Kim, Y. M., et al., "Cell Biology and Metabolism: Nitric Oxide Inhibits Apoptosis by Preventing Increases in Caspase-3-like Activity via Two Distinct Mechanisms," *J. Biol. Chem.* 272 (1997) 31138-31148.

Louw, R., et al., "Reaction of Sulphides with Acyl Nitrates; a Simple and Rapid Method for Preparing Sulphoxides," *J. Chem. Soc., Chem. Comm.* (1976) 496-497.

MacDonald, R. L., et al, "Pathophysiology of Cerebra Ischemia," *Neurol. Med. Chir.* (Tokyo) 38 (1998) 1-11.

Mizuno, A., et al, Inhibitory Effect of MCI-186, a Free Radical Scavenger, on Cerebral Ischemia Following Rat Middle Cerebral Artery Occlusion, *Gen. Pharmacol.* 30 (1998) 575-578.

Morgan, B. A., et al, "Approaches to the Discovery of Non-Peptide Ligands for Peptide Receptors and Peptidases," Annual Reports in Medicinal Chemistry. (editors Virick F.J., et al.) (1989) pp. 243-253, Academic Press, San Diego, CA.

Namura, S., et al., "Activation and Cleavage of Caspase-3 in Apoptosis Induced by Experimental Cerebral Ischemia," *J. Neurosci.* 18 (1998) 3659-3668.

Ni, B., et al, "Transient Global Forebrain Ischemia Induces a Prolonged Expression of the Caspase-3 mRNA in Rat Hippocampal CA1 Pyramidal Neurons," *J. Cereb. Blood Flow Metab.* 18 (1998) 248-256.

Nicholson, D. W., et al, "Caspases: Killer Proteases," *Trends Biochem. Sci.* 22 (1997) 299-306.

O'Neill, M. J., et al., "Decahydroisoquinolines: Novel Competitive AMPA/Kainate Antagonists with Neuroprotective Effects in Global Cerebral Ischaemia," *Neuropharmacol.* 37 (1998) 1211-1222.

Ouellette, R. J., et al., "Formation of Nitrate Esters by the Oxidation of Alkenes and Cyclopropanes with Thallium (III) Nitrate in Pentane," *J. Org. Chem.* 41 (1976) 2782-2783.

Owais, M., et al., "Chloroquine Encapsulated in Malaria-Infected Erythrocyte-Specific Antibody-Bearing Liposomes Effectively Controls Chloroquine-Resistant *Plasmodium berghei* Infections in Mice," *Antimicrob. Agents Chemother.* 39 (1995) 180.

Pallares, M., et al, "The Neurosteroid Pregnenolone Sulfate Infused Into the Nucleus Basalis Increases Both Acetylcholine Release in the Frontal Cortex or Amygdala and Spatial Memory," *Neurosci.* 87 (1998) 551-558.

PubChemCompound, datasheet [online compound summary of 5-(1-hydroxyethyl)-4-methylthiazole] Retrieved from the Internet: <URL: <http://pubchem.ncbi.nlm.nih.gov/search/search.cgi>> See CID 581758 (create date: Mar. 28, 2005), etc.

Ranade, V.V., et al., Site-Specific Drug Delivery Using Liposomes as Carriers, *J. Clin. Pharmacol.* 29 (1989) 685.

Strejan, G. H., et al., "Suppression of Chronic-Relapsing Experimental Allergic Encephalomyelitis in Strain-13 Guinea Pigs by Administration of Liposome-Associated Myelin Basic Protein," *J. Neuroimmunol.* 7 (1984) 27.

Tagami, M., et al, "Vitamin E Prevents Apoptosis in Cortical Neurons During Hypoxia and Oxygen Reperfusion," *Lab. Invest.* 78 (1998) 1415-1429.

Umemura, K., et al., "Neuroprotective Effect of a Novel AMPA Receptor Antagonist, YM90K, in Rat Focal Cerebral Ischaemia," *Brain Res.* 773 (1997) 61-65.

Umezawa, F., et al, "Liposome Targeting to Mouse Brain: Mannose As a Recognition Marker," *Biochem. Biophys. Res. Commun.* 153 (1988) 1038.

Venault, P. G., et al., "Effects of Convulsant Ligands of the GABA-Benzodiazepine Receptor Complex in Conflict and Learning Tasks in Mice," *J. L'Encéphale.* 18 (1992) 655.

Wu, J. et al., "Evidence for Involvement of the cGMP-Protein Kinase G Signaling System in the Induction of Long-Term Depression, But Not Long-Term Potentiation, in the Dentate Gyrus In Vitro," *J. Neurosci.* 18 (1998) 3589-3596.

Yang, K., et al., "Synthesis of Novel Organic Nitrate Esters: Guanylate Cyclase Activation and Tissue Relaxation," *J. Chem. Soc., Perkin Trans.* 1 (1996) 1073-1075.

Yang, Y. L., et al., "Striatal Glutamate Release is Important for Development of Ischemic Damage to Striatal Neurons During Rat Heatstroke," *Brain Res.* 795 (1998) 121-127.

Buchman, E., et al., "Studies of Crystalline Vitamin B1.1 X. Sulfite Cleavage. III. Chemistry of the Basic Product," *Journal of American Chemical Society*, 1935, vol. 57, No. 10, 1849-1851.

Sohda, T., et al., "Studies on Antidiabetic agents. II. Synthesis of 5-[4-(1-methylcyclohexylmethoxy)-benzyl]thiazolidine-2,4-dione (ADD-3878) and its derivatives," *Chemical and Pharmaceutical Bulletin* (Tokyo, Japan), 1982, vol. 30, No. 10, pp. 3580-3600.

Supplementary European Search Report in European patent application No. EP 11 77 8247.4, dated Oct. 17, 2013.

Bin, T., et al., "Analysis of Volatile Compounds of a Meat (Beef) Process Flavoring Made from Maillard Reaction of Model System." *Journal of Flavour and Fragrance Cosmetics*, 2005, No. 1. (English abstract).

Compound summary for 4-methyl-5-propan-2-yl-1,3-thiazole. National Center for Biotechnology Information. PubChem Com-

(56) References Cited

OTHER PUBLICATIONS pound Database; CID=207278, http://pubchem.ncbi.nlm.nih.gov/summary/summary.cgi?cid=207278 (accessed Feb. 20, 2014).
Compound summary for 5-Ethyl-4-methylthiazole. National Center for Biotechnology Information. PubChem Compound Database; CID=40380, http://pubchem.ncbi.nlm.nih.gov/summary/summary.cgi?cid=40380 (accessed Feb. 20, 2014).
Hamzé, A., et al., "Mono-and Bis-Thiazolium Salts Have Potent Antimalarial Activity." *Journal of Medicinal Chemistry*, 2005, vol. 48, No., pp. 3639-3643.

* cited by examiner

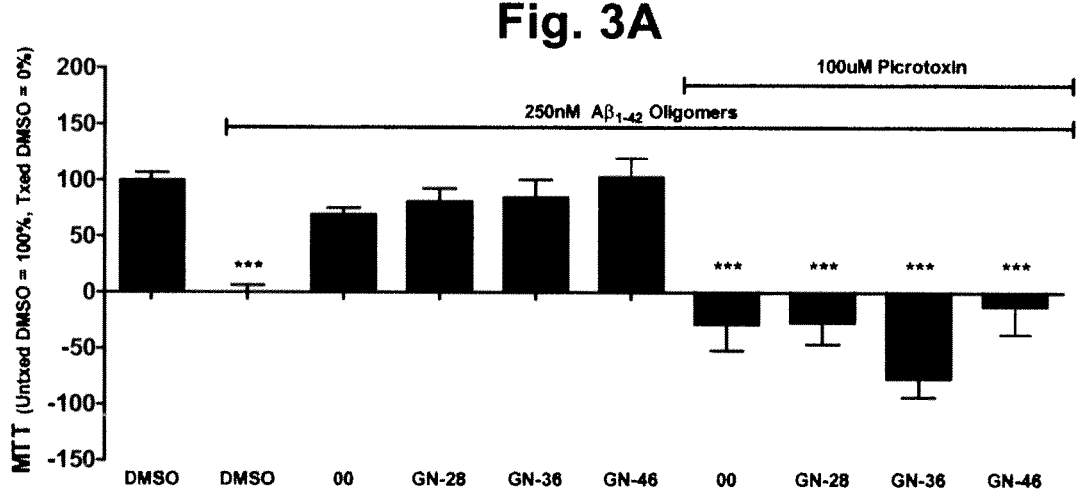
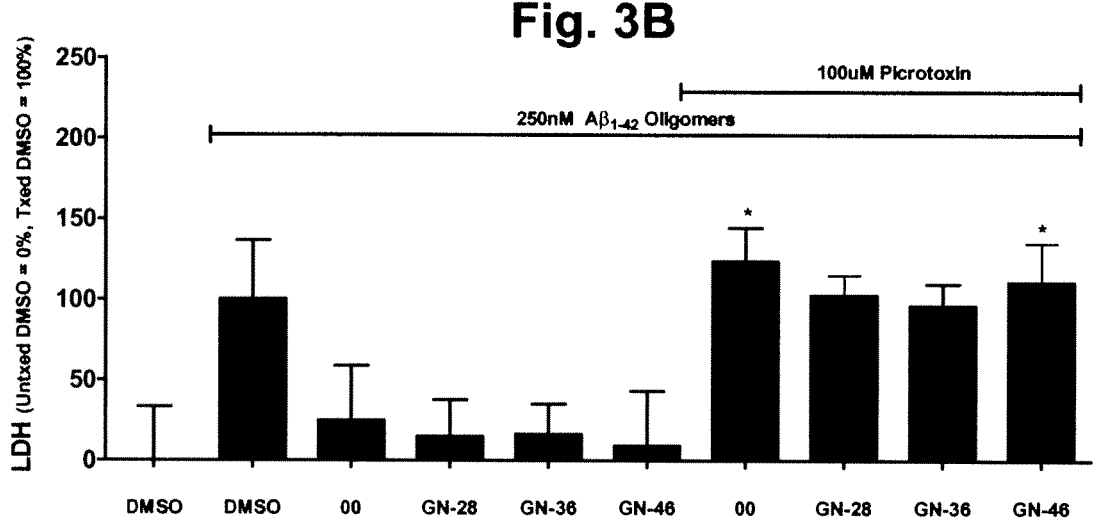

US 8,957,086 B2

COMPOUNDS AND METHODS OF TREATING BRAIN DISORDERS

CROSS REFERENCE TO RELATED APPLICATION

This application claims the benefit of U.S. provisional patent application No. 61/376,411, filed Aug. 24, 2010, U.S. provisional patent application No. 61/371,356, filed Aug. 6, 2010, and U.S. provisional patent application No. 61/331,483, filed May 5, 2010, each incorporated herein by reference in its entirety.

STATEMENT OF GOVERNMENT INTEREST

This invention was made with U.S. government support under grant number U01 AG031294 awarded by the National Institutes of Health (NIH)/National Institute on Aging (NIA). The U.S. government has certain rights in the invention.

FIELD OF THE INVENTION

The present invention relates to nitrated and non-nitrated compounds and use thereof in mitigating cellular damage. More particularly, the present invention relates to nitrated and non-nitrated thiazole compounds having therapeutic utility as agents that protect brain tissue from injury, that ameliorate symptoms and pathologies associated with brain injuries, and that are useful in the treatment of neurodegenerative diseases and conditions.

BACKGROUND OF THE INVENTION

Nitric oxide (NO) signaling is essential for normal physiological function in the central nervous system (CNS) and is compromised in many disease states. NO can serve as a retrograde synaptic messenger, as an intracellular messenger, and as a lateral diffusible messenger in the CNS. NO plays a critical role in signal transduction cascades that are compromised in dementia, and thereby contribute to the symptoms of cognitive impairment that characterize Alzheimer's Disease (AD). NO activates soluble guanylyl cyclase (sGC) to release cyclic guanosine-2':3'-monophosphate (cGMP). NO/cGMP signaling is important for modulating synaptic transmission and plasticity in brain regions, such as the hippocampus and cerebral cortex, which are critical for learning and memory (H. Son et al., *Learn Mem* 1998, 5, 231-245; and Y. F. Lu et al., *J Neurosci* 1999, 19, 10250-10261). Evidence exists that NO may positively impact learning, memory, and cognition through cGMP-dependent and independent pathways (T. M. Edwards et al., *Neurobiol Learn Mem* 2002, 77, 313-326).

Compounds that mimic the effects of NO, i.e., NO mimetics, bypass cholinergic receptor activation and are expected to provide multiple pathways of treating and circumventing dementia. The action of an appropriate nitrate in the hippocampus modulates signaling cascades, in part via MAPK/ERK (mitogen activated protein kinase-extracellular signal-regulated kinase) and CREB (cAMP responsive element binding protein), leading to amelioration of learning and memory pathways under pathophysiological conditions which might lead to neurodegeneration.

Nitrates are NO mimetics that can act as NO donors. In contrast to other NO donors, nitrates do not release high fluxes of NO, which is potentially harmful. Bioactivation and metabolism of nitrates is a variable that strongly influences activity and pharmaceutical use. Whereas the potent hypotensive effects of the organic nitrate vasodilator nitroglycerin may be deleterious in the treatment of depression and dementia, it is theorized herein, but not relied upon, that regulation of systemic versus central effects is required for development of new and useful therapeutic agents useful in the treatment of brain injuries, dementia, and neurological diseases.

Cerebral ischemia results in marked increases in the release of the excitatory amino acid glutamate in the affected brain region (Bullock et al., 1998; Huang et al., 1998; Yang et al., 1998). In both humans (Bullock et al., 1998) and experimental animals (Huang et al., 1998; Goda et al., 1998; Yang et al., 1998), the amount of glutamate released during ischemia is positively correlated with the extent of brain injury. In experimental animal models of cerebral ischemia, a decreased release of glutamate during ischemia (Goda et al., 1998) or a blockade of glutamate receptors with antagonists (Ibarrola et al., 1998; O'Neill et al., 1998; Umemura et al., 1997) significantly reduces the extent of brain injury. However, these interventions are only effective when administered prior to or during the ischemic insult. To be broadly useful, a therapeutic intervention preferably is effective when administered after a period of ischemia.

Reoxygenation and reperfusion after a period of ischemia contributes significantly to the development of brain injury. Oxygen radicals, especially superoxide and peroxynitrite, formed in the period after an ischemic event, may initiate processes, such as breakdown of membrane lipids (lipid peroxidation), that lead to loss of cell membrane integrity and inhibition of mitochondrial function (Macdonald and Stoodley, 1998; Gaetani et al, 1998). Oxidative stress may be a factor involved in initiation of apoptotic neuronal cell death (Tagami et al., 1998). In experimental animal models of ischemic brain injury, a cytokine attenuating anti-inflammatory compound has been found to reduce the extent of neuronal injury and cell death (Chan et al., 1998; Mizuno et al., 1998; Tagami et al., 1998). Neurodegeneration therefore is mitigated by inhibition of cytokine induced damage.

Clomethiazole (CMZ) is a sedative/hypnotic and anticonvulsant, currently in clinical use for anxiety in the elderly. Ample evidence supports the actions of CMZ as both GABAmimetic and anti-inflammatory. These properties together provide neuroprotection in animal models of ischemic stroke (A. N. Clarkson et. al., 2005, *The FASEB Journal*, 19, 1036-1038). In addition to acting as a $GABA_A$ potentiator, it has been proposed that CMZ also inhibits the p38 mitogen-activated protein kinase pathway (A. Simi et al., 2000, *Journal of Cerebral Blood Flow & Metabolism*, 20, 1077-1088) and decreases inducible nitric oxide synthase (iNOS) expression in cortical glial cells (M. J. Wilby et. al., 2004, *CNS Drug Reviews*, 10, 281-294). AR-A008055 was reported as a CMZ analog (R. M. Nelson et. al., 2001, *Neuropharmacology*, 41, 159-166).

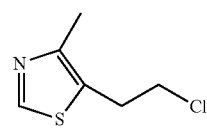

CMZ

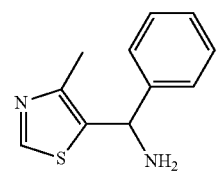

AR-A008055

-continued

GT-1061

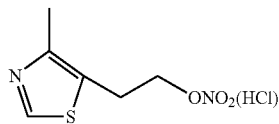
ONO₂(HCl)

GT-1061 incorporates the 5-methylthiazole (MZ) pharmacophore of CMZ and retains GABA$_A$ potentiating, as well as anticonvulsant, activity with attenuated sedative/hypnotic effects. In preclinical studies, GT-1061 reversed cognitive impairment in experimental models of dementia, and also significantly improved learning and memory in experimental animals in which the cholinergic systems of the basal forebrain had been lesioned (B. M. Bennett et al., *Neuropsychopharmacology* 2007, 32, 505-13; G. R. J. Thatcher et al., *Curr Alzheimer. Res.* 2006, 3, 237-45; G. R. J. Thatcher et al., *J. Alzheimer's Dis.* 2004, 6, S75-84.). The aliphatic nitrate group of GT-1061 provides nitric oxide (NO) mimetic activity via cGMP/ERK/CREB signal transduction enhancing synaptic plasticity and via brain-derived neurotrophic factor (BDNF) upregulation, thereby enhancing neuronal plasticity and neurogenesis. Evidence exists for attenuated NO/cGMP signaling and downregulated BDNF in Alzheimer's disease (AD) and other neurodegenerative diseases associated with aging. GT-1061 has completed Phase 1A clinical trials for AD.

The present invention therefore is directed to novel 4-methylthiazole compounds having neuroprotective and anti-neuroinflammatory properties, and that are useful in the methods of protecting brain tissue from injury and of ameliorating symptoms and pathologies associated with brain injuries.

SUMMARY OF THE INVENTION

The present invention is directed to compounds having the following generic structures:

(I, non-nitrate)

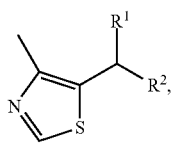

wherein $R^1$ is selected from the group consisting of H, substituted or unsubstituted aryl, substituted or unsubstituted heteroaryl, a substituted or unsubstituted $C_{1-24}$ aliphatic group, —$(CH_2)_{1-3}$aryl, and —$(CH_2)_{1-3}$heteroaryl;

$R^2$ is selected from the group consisting of H, substituted or unsubstituted aryl, substituted or unsubstituted heteroaryl, a substituted or unsubstituted $C_{1-24}$ aliphatic group, —$OR^a$, halo, $N(R^a)(R^b)$, $N_3$, —$(CH_2)_{1-3}N_3$, —$(CH_2)_{1-3}OR^a$, and —$(CH_2)_{1-3}$halo, wherein at least one of $R^1$ and $R^2$ is different from H; and $R^a$ and $R^b$, independently, are selected from the group consisting of H, $C_{1-3}$alkyl, aryl, and heteroaryl, or $R^a$ and $R^b$ are taken together with the atom to which they are attached to from a 3 to 6 membered ring;

or a pharmaceutically acceptable salt, prodrug or hydrate thereof; and (II, nitrate)

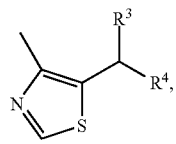

wherein $R^3$ is selected from the group consisting of H, substituted or unsubstituted aryl, substituted or unsubstituted heteroaryl, a substituted or unsubstituted $C_{1-24}$ aliphatic group, —$N_3$, —$(CH_2)_{1-3}$aryl, and —$(CH_2)_{1-3}$heteroaryl;

$R^4$ is selected from the group consisting of $ONO_2$, —$(CH_2)_{1-3}ONO_2$, —$NHC(=O)O(CH_2)_{1-6}ONO_2$, —$NHC(=O)C(R^a)(R^b)CH_2ONO_2$, —$NHC(=O)CH_2C(R^a)(R^b)ONO_2$, —$NHC(=O)YC(R^a)(R^b)CH_2ONO_2$, —$NHC(=O)YCH_2C(R^a)(R^b)ONO_2$, —$OC(=O)CH_2C(R^a)(R^b)ONO_2$, —$OC(=O)C(R^a)(R^b)CH_2ONO_2$, —$O(CH_2)_{1-3}ONO_2$, —$O(CH_2)_{1-2}O(CH_2)_{1-2}ONO_2$, and —$O(CH_2)_{1-3}YCH_2$—$[CH(ONO_2)]_n$—$(CH_2)_{1-2}ONO_2$, and heteroaryl having at least one aliphatic nitro substituent;

$R^a$ and $R^b$, independently, are selected from the group consisting of H, $C_{1-3}$alkyl, aryl, and heteroaryl, or $R^a$ and $R^b$ are taken together with the carbon to which they are attached to from a 3 to 6 membered ring;

n is an integer of 1 through 5; and

Y is O, S, or NH;

or a pharmaceutically acceptable salt, prodrug, or hydrate thereof.

Another aspect of the present invention is to provide nitrated derivatives of the compounds of structural formula (I).

Another aspect of the present invention is to provide a method of protecting the brain from injury, and to provide a method of mitigating brain tissue and cellular damage by administering a therapeutically effective amount of a compound of structural formula (I) or (II) to an individual in need thereof. A compound of structural formula (I) or (II) can be administered before, during, or after the brain injury, e.g., a period of ischemia.

Yet another aspect of the present invention is to protect brain tissue and/or to mitigate cellular damage associated with cytokine therapy by administering a therapeutically effective compound of structural formula (I) or (II) to an individual undergoing cytokine therapy before, during, or after cytokine therapy.

Still another aspect of the present invention is to provide a composition comprising a compound of structural formula (I) or (II) and a pharmaceutically acceptable carrier and/or excipient.

These and other aspects and features of the present invention will become apparent from the following detailed description of the preferred embodiments.

BRIEF DESCRIPTION OF THE DRAWINGS

FIG. 3A contains bar graphs of M DMSO control) for control samples and compounds of structural formula (I);

FIG. 3B contains bar graphs of LDH (% DMSO control) for control samples and compounds of structural formula (I);

DETAILED DESCRIPTION OF THE PREFERRED EMBODIMENTS

Figure 1A:
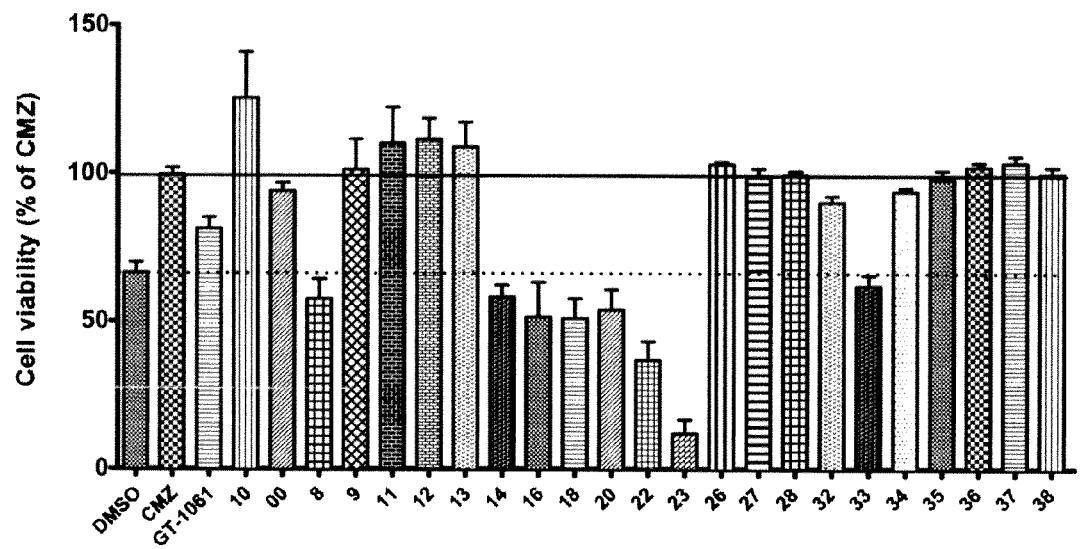
FIG. 1A contains bar graphs of cell viability (% of CMZ) for DMSO, CMZ, GT-1061, and compounds of structural formula (I)

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

The terms "present compound", "compounds of the invention", "compounds of the present invention", and similar terms mean compounds of structural formula (I) and structural formula (II).

As used herein, the terms "treat," "treating," "treatment," and the like refer to eliminating, reducing, or ameliorating a disease or condition and/or a symptom associated therewith. Although not precluded, treating a disease or condition does not require that the disease, condition, or symptom associated therewith be completely eliminated. The terms "treat", "treating", and "treatment" also refer to protecting tissues and cells prior to the onset of an injury and to preventing or ameliorating further injury after onset of the injury. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a present compound to an individual in need of such treatment.

Within the meaning of the invention, "treatment" also includes relapse prophylaxis or phase prophylaxis, as well as the treatment of acute or chronic signs, symptoms, and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of a therapeutic agent that is sufficient, when administered by a method of the invention, to efficaciously deliver an agent for the treatment of a condition or disease of interest to an individual in need thereof.

The term "container" means any receptacle and closure therefor suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

The use of the terms "a", "an", "the", and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

The compounds of the present invention mitigate cellular damage in the brain and modulate neurological conditions. The present compounds have therapeutic utility as agents that protect brain tissues from injury and dysfunction, ameliorate symptoms and pathologies associated with brain injury or dysfunction, and relieve neurological disorders, including anxiety. The present compounds protect neurons from dysfunction, damage, and death, and provide anti-inflammatory actions in neurons and other cells. The present compounds also provide sedation.

A compound of the present invention has the following generic formulas (I) and (II):

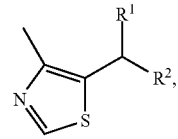

(I, non-nitrate)

wherein $R^1$ is selected from the group consisting of H, substituted or unsubstituted aryl, substituted or unsubstituted heteroaryl, a substituted or unsubstituted $C_{1-24}$ aliphatic group, $—(CH_2)_{1-3}aryl$, and $—(CH_2)_{1-3}heteroaryl$;

$R^2$ is selected from the group consisting of H, substituted or unsubstituted aryl, substituted or unsubstituted heteroaryl, a substituted or unsubstituted $C_{1-24}$ aliphatic group, $—OR^a$, halo, $N(R^a)(R^b)$, $N_3$, $—(CH_2)_{1-3}N_3$, $—(CH_2)_{1-3}OR^a$, and $—(CH_2)_{1-3}halo$, wherein at least one of $R^1$ and $R^2$ is different from H; and $R^a$ and $R^b$, independently, are selected from the group consisting of H, $C_{1-3}alkyl$, aryl, and heteroaryl, or $R^a$ and $R^b$ are taken together with the atom to which they are attached to from a 3 to 6 membered ring;

or a pharmaceutically acceptable salt, prodrug or hydrate thereof; and

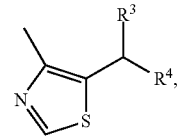

(II, nitrate)

wherein $R^3$ is selected from the group consisting of H, substituted or unsubstituted aryl, substituted or unsubstituted heteroaryl, a substituted or unsubstituted $C_{1-24}$ aliphatic group, —N3, —(CH$_2$)$_{1-3}$aryl, and —(CH$_2$)$_{1-3}$heteroaryl;

$R^4$ is selected from the group consisting of ONO$_2$, —(CH$_2$)$_{1-3}$ONO$_2$, —NHC(=O)O(CH$_2$)$_{1-6}$ONO$_2$, —NHC(=O)C(R$^a$)(R$^b$)CH$_2$ONO$_2$, —NHC(=O)CH$_2$C(R$^a$)(R$^b$)ONO$_2$, —NHC(=O)YC(R$^a$)(R$^b$)CH$_2$ONO$_2$, —NHC(=O)YCH$_2$C(R$^a$)(R$^b$)ONO$_2$, —OC(=O)CH$_2$C(R$^a$)(R$^b$)ONO$_2$, —OC(=O)C(R$^a$)(R$^b$)CH$_2$ONO$_2$, —O(CH$_2$)$_{1-3}$ONO$_2$, —O(CH$_2$)$_{1-2}$—O(CH$_2$)$_{1-2}$ONO$_2$, and —O(CH$_2$)$_{1-3}$YCH$_2$—[CH(ONO$_2$)]$_n$—(CH$_2$)$_{1-2}$ONO$_2$, and heteroaryl having at least one aliphatic nitro substituent;

$R^a$ and $R^b$, independently, are selected from the group consisting of H, $C_{1-3}$ alkyl, aryl, and heteroaryl, or $R^a$ and $R^b$ are taken together with the carbon to which they are attached to from a 3 to 6 membered ring;

n is an integer of 1 through 5; and

Y is O, S, or NH;

or a pharmaceutically acceptable salt, prodrug, or hydrate thereof.

In some preferred embodiments, W and $R^3$ are phenyl and $R^2$ and $R^4$ are heteroaryl, such as triazolyl and substituted triazolyl. In other preferred embodiments, $R_1$ and $R^2$ are H and $R^2$ and $R^4$ are —CH$_2$heteroaryl, such as —CH$_2$-triazolyl and substituted —CH$_2$-triazolyl, for example,

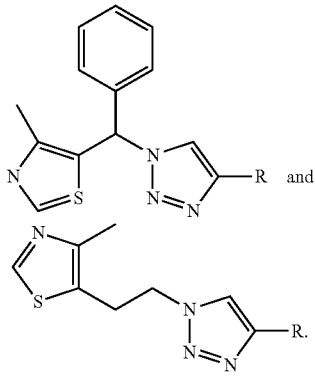

As used herein, the term "alkyl" refers to straight chained and branched saturated hydrocarbon groups, nonlimiting examples of which include methyl, ethyl, and straight chain and branched propyl, butyl, pentyl, and hexyl groups. The term (CH$_2$)$_{1-2}$ refers to CH$_2$ or CH$_2$CH$_2$. An alkyl group can be substituted or unsubstituted, for example with one or more of alkoxy (—OR$^a$), aryloxy (—Oaryl), sulfhydryl (—SH), alkylthio (—SR$^a$), arylthio (—Saryl), halo, hydroxyl (—OH), fluoroalkyl, perfluoralkyl, amino, aminoalkyl, disubstituted amino, quaternary amino, hydroxyalkyl, carboxyalkyl, and carboxyl groups, wherein $R^a$ is defined above.

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted, for example, with one or more, and in particular one to four, groups independently selected from, for example, halo, alkyl, —OR$^a$, —SW, —NO$_2$, —CN, —N(R$^a$)(R$^b$), —(CH$_2$)$_{1-3}$OR$^a$, —CO$_2$R$^a$, —CON(R$^a$)(R$^b$), —C(=O)(CH$_2$)$_{1-3}$N(R$^a$)(R$^b$), —CF$_3$, and —OCF$_3$, wherein $R^a$ and $R^b$ are defined above. Exemplary aryl groups include, but are not limited to, phenyl, naphthyl, tetrahydronaphthyl, chlorophenyl, methylphenyl, methoxyphenyl, trifluoromethylphenyl, 2,4-methoxychlorophenyl, and the like.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, —SR$^a$, —NO$_2$, —CN, —N(R$^a$)(R$^b$), —(CH$_2$)$_{1-3}$OR$^a$, —CO$_2$R$^a$, —CON(R$^a$)(R$^b$), —C(=O)(CH$_2$)$_{1-3}$N(R$^a$)(R$^b$), —CF$_3$, and OCF$_3$, wherein $R^a$ and $R^b$ are defined above. Examples of heteroaryl groups include, but are not limited to, thienyl, furyl, oxazolyl, quinolyl, thiophenyl, isoquinolyl, indolyl, triazinyl, triazolyl, isothiazolyl, isoxazolyl, imidazolyl, benzothiazolyl, pyrimidinyl, thiazolyl, thiadiazolyl, pyridinyl, pyridazinyl, pyrazolyl, pyrazinyl, quinolyl, tetrazolyl, oxazolyl, pyrrolyl, benzimidazolyl, benzofuranyl, cinnolinyl, indazolyl, indolizinyl, phthalazinyl, triazinyl, isoindolyl, purinyl, oxadiazolyl, furazanyl, benzofurazanyl, benzothiophenyl, benzotriazolyl, benzothiazolyl, benzisothiazolyl, benzoxazolyl, benzisoxazolyl, benzimidazolyl, quinazolinyl, quinoxalinyl, napththyridinyl, dihydroquinolyl, tetrahydroquinolyl, dihydroisoquinolyl, tetrahydroisoquinolyl, benzofuryl, furopyridinyl, pyrrolopyrimidinyl, and azaindolyl.

As used herein, the term "a $C_{1-24}$ aliphatic group" means an alkyl or alkenyl group containing the indicated number of 1 to 24 carbon atoms. The aliphatic group can contain up to four heteroatoms in the chain, which are independently selected from O, S, and NR$^a$. The aliphatic group also can contain 0 to 4 carbon-carbon double bonds. The aliphatic group can be unsubstituted or substituted with one to four substituents, for example, independently substituted with halo, $C_{1-3}$alkyl, —CF$_3$, —OCF$_3$, —OR$^a$, —NO$_2$, and —N(R$^a$)(R$^b$), or other substituents defined above in connection with an "alkyl" group. $R^a$ and $R^b$ are defined above.

As used herein the term "$C_{x-y}$" means a group containing from x to y carbon atoms. "Me" and "Et" are abbreviations for methyl and ethyl. As used herein, the term "halo" means fluoro, chloro, bromo, and iodo.

As used herein, a group such as

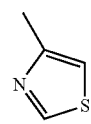

Is an abbreviation for

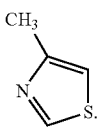

In one embodiment of the present invention the compound is free of nitrate groups and has a the structural formula (I). Examples of this embodiment include the following nonlimiting structures (a) through (g).

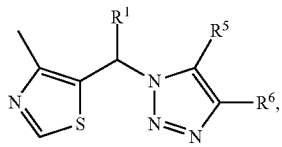
(a)

wherein $R^5$ is hydrogen, a substituted or unsubstituted aryl group, a substituted or unsubstituted heteroaryl group, such as 3-pyridinyl, or a substituted or unsubstituted aliphatic group having from 1 to 6 carbon atoms in the chain, which optionally contains 1 to 4 O, S, N($R^a$), and/or unsaturations in the chain; and $R^6$ is hydrogen, a substituted or unsubstituted aryl group, a substituted or unsubstituted heteroaryl group, such as 3-pyridinyl, a substituted or unsubstituted aliphatic group having from 1 to 6 carbon atoms in the chain, which optionally contains 1 to 4 O, S, N($R^a$), and/or unsaturations in the chain.

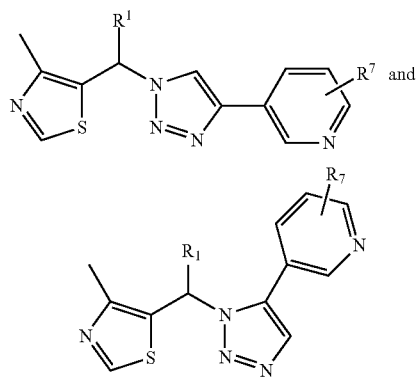
(b)

(c)

wherein $R^1$ is a substituted or unsubstituted phenyl group or a substituted or unsubstituted heteroaryl group, wherein substituents on $R^1$ are individually selected from the group consisting of halo (—F, —Cl, —Br), $C_{1-3}$alkyl (Me), $OR^a$, wherein $R^a$ is H or $C_{1-3}$alkyl (OMe), $NO_2$, $NR^a_2$($NMe_2$), $CH_2OR^a$($CH_2OH$), $CO_2R^a$($CO_2Et$, $CO_2H$, $CO_2Me$), $CONR^a_2$($CONH_2$), and $CO(CH_2)_{1-3}NR^a_2$ ($CO(CH_2)_2NEt_2$), and $R^7$ is selected from the group consisting of halo (—F, —Cl, —Br), $C_{1-3}$alkyl (Me), $OR^a$, wherein $R^a$ is H or $C_{1-3}$alkyl (OMe), $NO_2$, $NR^a_2$($NMe_2$), $CH_2OR^a$($CH_2OH$), $CO_2R^a$($CO_2Et$, $CO_2H$, $CO_2Me$), $CONR^a_2$($CONH_2$), $CO(CH_2)_{1-3}NR^3_2$($CO(CH_2)_2NEt_2$), and H.

Examples of this embodiment include:

GN-12

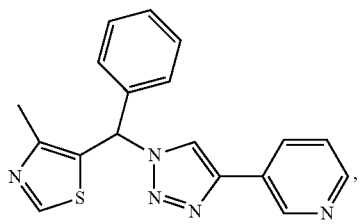

F-12

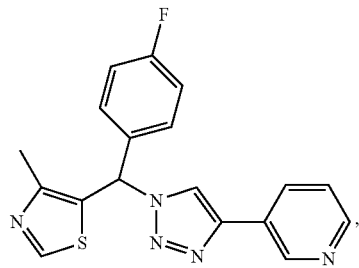

GN-31

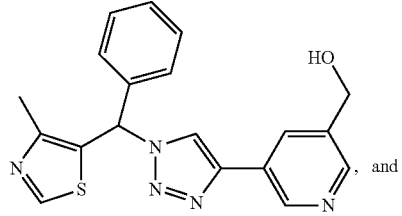, and

GN-37

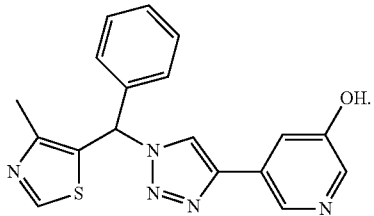

GN-38

(d)

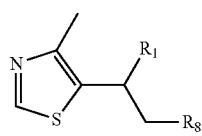

wherein $R^1$ is H a substituted or unsubstituted —$CH_2$-phenyl group or a substituted or unsubstituted —$CH_2$heteroaryl group, wherein substituents on $R^1$ independently are selected from the group consisting of halo (—F, —Cl, —Br), $C_{1-3}$alkyl (Me), $OR^a$, wherein $R^a$ is H or $C_{1-3}$alkyl (OMe), $NO_2$, $NR^a_2$($NMe_2$), $CH_2OR^a$ ($CH_2OH$), $CO_2R^a$($CO_2Et$, $CO_2H$, $CO_2Me$), $CONR^a_2$ ($CONH_2$), and CO(CH$_2$)$_{1-3}$NR$^a{}_2$(CO(CH$_2$)$_2$NEt$_2$) and R$^2$ is —CH$_2$R$^8$, wherein R$^8$ is selected from the group consisting of OR$^a$ (OH), halo (Cl), NR$^a{}_2$ (NH$_2$, NMe$_2$), N$_3$, and a 1,2,3-triazole ring having 3-pyridyl at the 4 or 5 position.

(e)

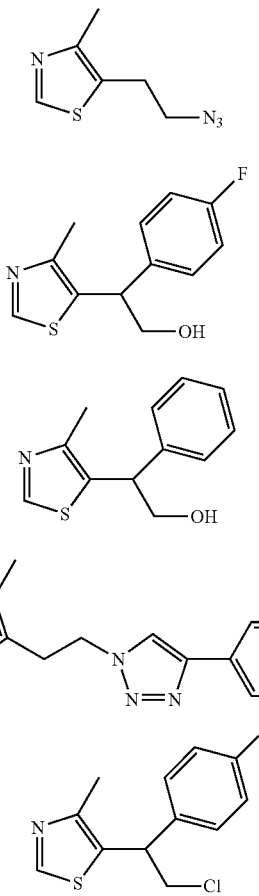

GN-26

GN-27

GN-28

GN-35

(f)

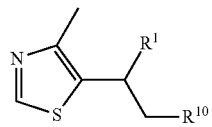

wherein R$^1$ is a substituted or unsubstituted phenyl group or a substituted or unsubstituted aryl heteroaryl group, wherein substituents on R$^1$ independently are selected from the group consisting of halo (—F, —Cl, —Br), C$_{1-3}$alkyl (Me), OR$^a$, wherein R$^a$ is H or C$_{1-3}$alkyl (OMe), NO$_2$, NR$^a{}_2$ (NMe$_2$), CH$_2$OR$^a$ (CH$_2$OH), CO$_2$R$^a$ (CO$_2$Et, CO$_2$H, CO$_2$Me), CONR$^a{}_2$ (CONH$_2$), and CO(CH$_2$)$_{1-3}$NR$^a{}_2$(CO(CH$_2$)$_2$NEt$_2$), and R$^{10}$ is selected from the group consisting of OR$^a$(OH), halo (Cl), NR$^a{}_2$ (NH$_2$, NMe$_2$), and N$_3$.

(g)

GN-36

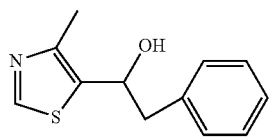

-continued

GN-43

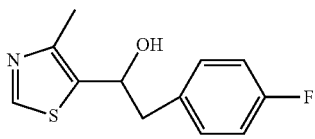

In another embodiment of the invention, the compound contains one or more aliphatic nitrate group and has a structural formula (II). Examples of this embodiment include the following nonlimiting structures.

(a)

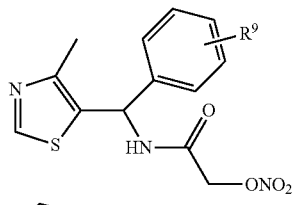

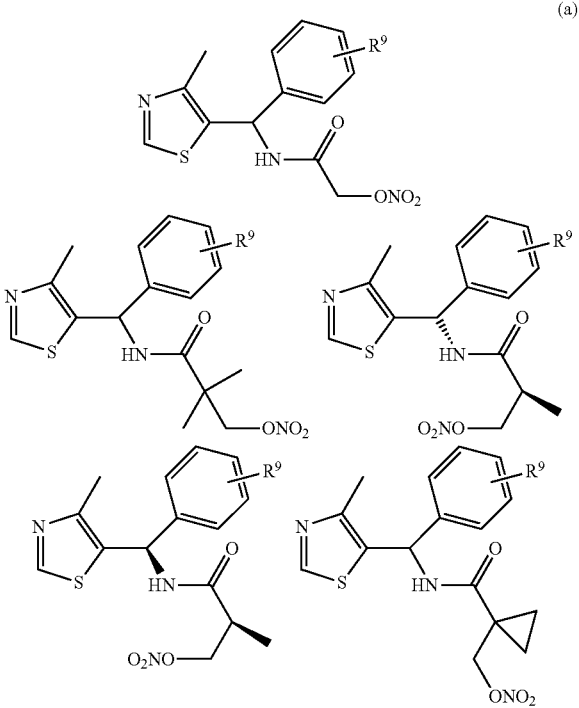

wherein R$^9$ is selected from the group consisting of halo (—F, —Cl, —Br), C$_{1-3}$alkyl (Me), OR$^a$, wherein R$^a$ is H or C$_{1-3}$alkyl (OMe), NO$_2$, CO$_2$R$^a$ (CO$_2$Et, CO$_2$H, CO$_2$Me), CONR$^a{}_2$ (CONH$_2$), and CO(CH$_2$)$_{1-3}$NR$^a{}_2$(CO(CH$_2$)$_2$NEt$_2$), and H.

(b)

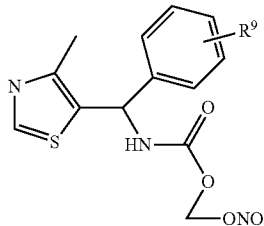

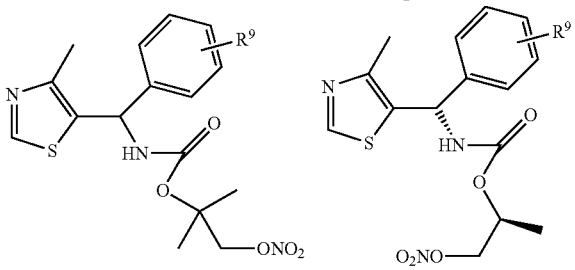

-continued
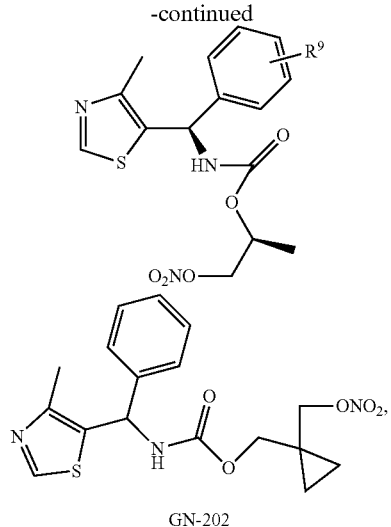
GN-202
wherein R⁹ is defined as above.
(c)
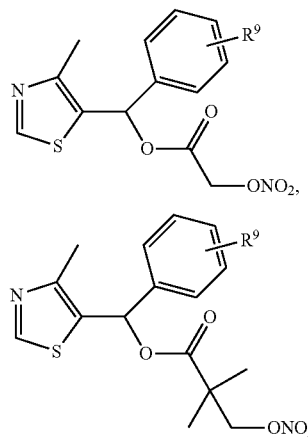
GM-30
wherein R⁹ is defined as above.
(d)
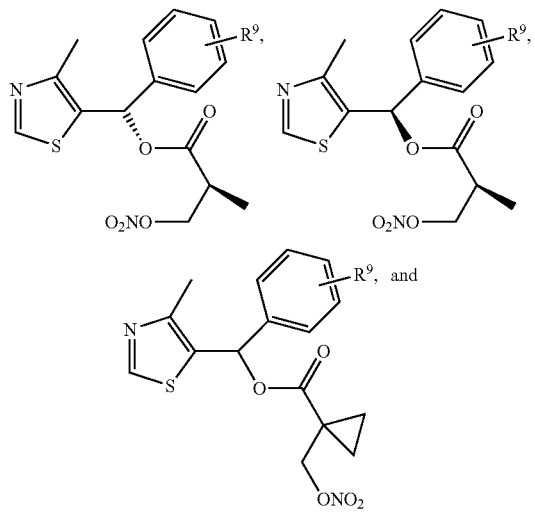
GN-30
wherein R⁹ is defined as above.
(e)
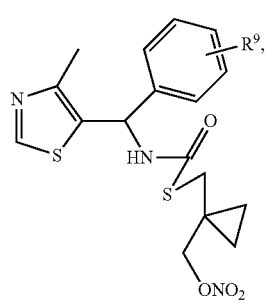

-continued
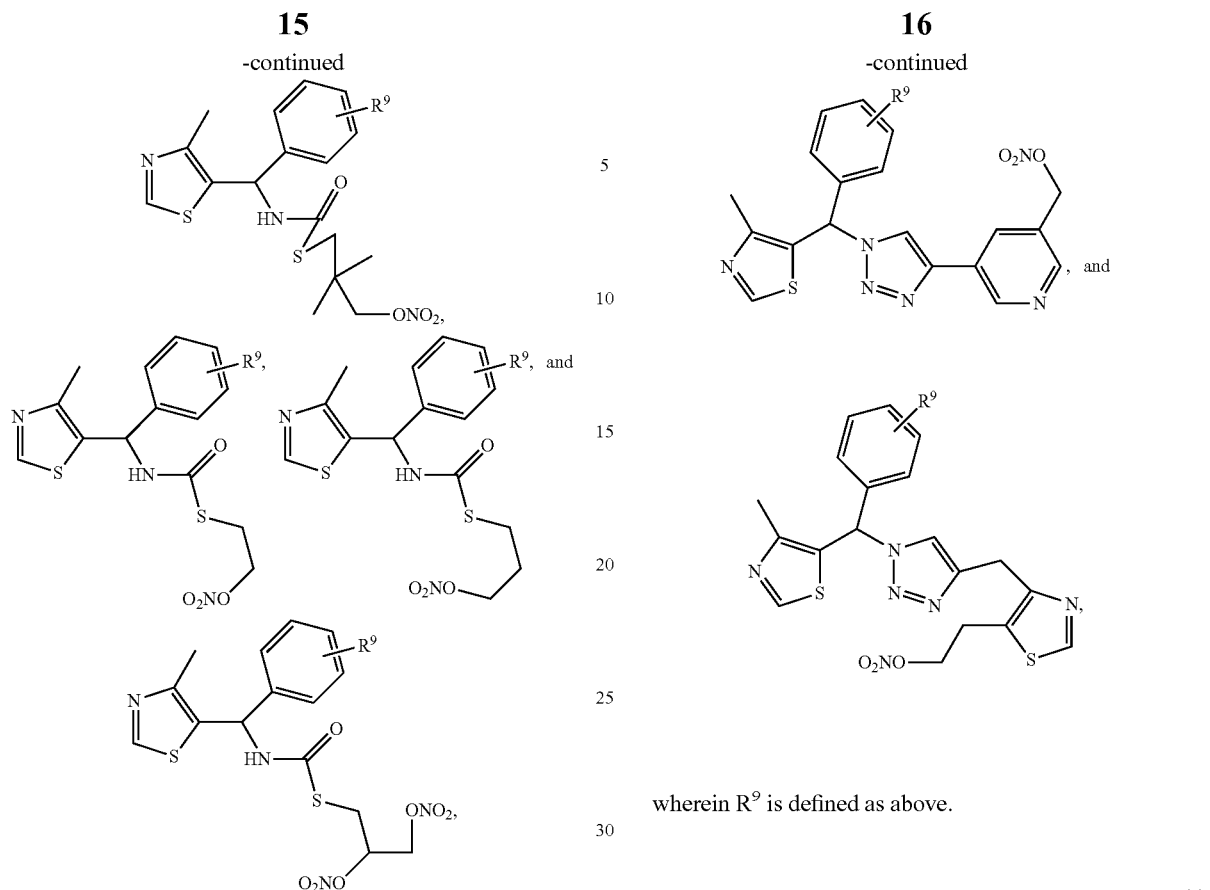
wherein R⁹ is defined as above.
(f)
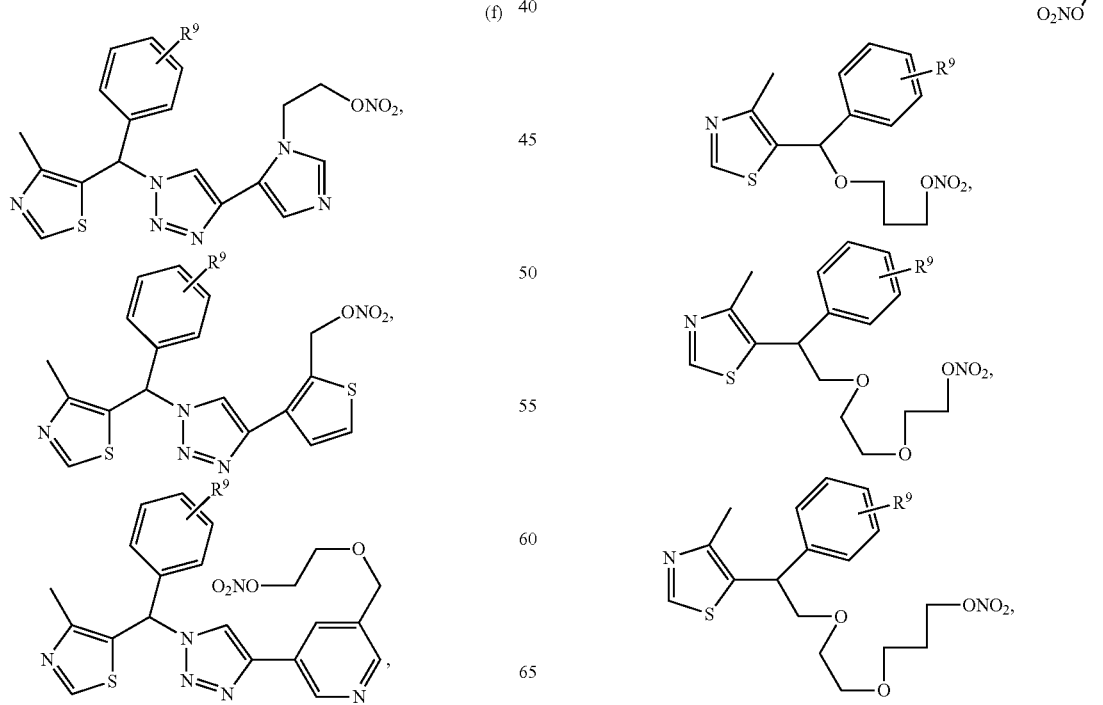
wherein R⁹ is defined as above.
(g)

GN-29

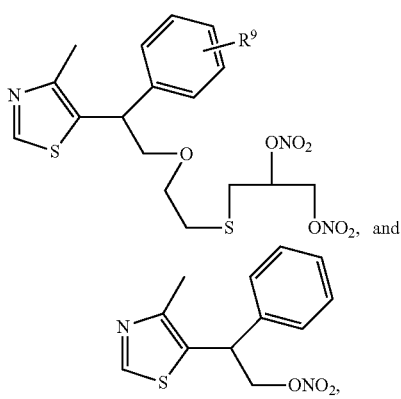

wherein R⁹ is defined as above.

Additionally, salts, prodrugs, and hydrates of the compounds of structural formulas (I) and (II) also are included in the present invention and can be used in the methods disclosed herein. The present invention further includes all possible stereoisomers and geometric isomers of the compounds of structural formulas (I) and (II). The present invention includes both racemic compounds and optically active isomers. When a present compound is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883-888 (1997). Resolution of the final product, an intermediate, or a starting material can be achieved by any suitable method known in the art. Additionally, in situations where tautomers of a present compound are possible, the present invention is intended to include all tautomeric forms of the compounds.

Prodrugs of the compounds of structural formulas (I) and (II) are included in the present invention. It is well established that a prodrug approach, wherein a compound is derivatized into a form suitable for formulation and/or administration, then released as a drug in vivo, has been successfully employed to transiently (e.g., bioreversibly) alter the physicochemical properties of the compound (see, H. Bundgaard, Ed., "Design of Prodrugs," Elsevier, Amsterdam, (1985); R. B. Silverman, "The Organic Chemistry of Drug Design and Drug Action," Academic Press, San Diego, chapter 8, (1992); K. M. Hillgren et al., *Med. Res. Rev.*, 15, 83 (1995)).

Compounds of the present invention can contain one or more functional groups. The functional groups, if desired or necessary, can be modified to provide a prodrug. Suitable prodrugs include, for example, acid derivatives, such as amides and esters. It also is appreciated by those skilled in the art that N-oxides can be used as a prodrug.

Compounds of the present invention can exist as salts. Pharmaceutically acceptable salts of the compounds of the invention often are preferred in the methods of the invention. As used herein, the term "pharmaceutically acceptable salts" refers to salts or zwitterionic forms of a compound of structural formula (I) or (II). Salts of various present compounds can be prepared during the final isolation and purification of the compounds or separately by reacting the compound with an acid having a suitable cation. The pharmaceutically acceptable salts of a present compound can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the invention include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference to compounds of the present invention appearing herein is intended to include a compound of structural formula (I) or (II), as well as pharmaceutically acceptable salts, hydrates, or prodrugs thereof.

Compounds of Structural Formula (I)

The compounds of structural formula (I) are used in methods of preventing or mitigating tissue and/or cellular damage in the brain of an individual by administering a therapeutically effective amount of the compound of structural formula (I) to the individual. The tissue and/or cellular damage can be associated with aging, septic shock, ischemia/reperfusion injury, encephalomyelitis, meningitis, lymphocytic choriomeningitis, bacterial infection, viral infection, fungal infection, parasitic infection, chronic fatigue syndrome, stroke, cerebral ischemia, chronic neurodegenerative disease, cystic fibrosis, schizophrenia, depression, premenstrual syndrome, anxiety, addiction, migraine, central nervous system (CNS) trauma, or vascular aneurysm.

The tissue and/or cellular damage also can be associated with neurological diseases such as, for example, Parkinson's disease, Alzheimer's disease, Huntington's disease, multiple sclerosis, amylotrophic lateral sclerosis, AIDS-induced dementia, epilepsy, alcoholism, alcohol withdrawal, drug-induced seizures, viral/bacterial/fever-induced seizures, trauma to the head, hypoglycemia, hypoxia due to myocardial infarction, cerebral vascular occlusion, cerebral vascular hemorrhage, hemorrhage, or environmental excitotoxins of plant, animal, or marine origin.

The tissue and/or cellular damage further can be associated with cytokine therapy, wherein a compound of structural formula (I) is administered to the subject before, during, and/or after the administration of the therapy to ameliorate such damage.

"Mitigating neurodegeneration" as used herein involves affecting neuroprotection, inhibiting or preventing neurodegeneration, and/or ameliorating the manifestations or symptoms of neurodegeneration. Such amelioration includes effecting cognition enhancement, as is quantified by tests known in the art (e.g., Venault et al., 1992, incorporated herein by reference). "Modulating" a biological process as used herein (for example, modulating activity of the non-glutamate neuroreceptors) encompasses both increasing (positively modulating) and decreasing (negatively modulating) such activity, and thus inhibition, potentiation, agonism, and antagonism of the biological process.

The compounds of structural formula (I) also are useful in methods of affecting neuroprotection, mitigating neurodegeneration, affecting cognition enhancement, and/or protecting tissues from oxidative injury. The compounds of structural formula (I) therefore are neuroprotective agents and are used for cognition enhancement.

As discussed below, compounds of structural formula (II) can be used in the same methods as the compounds of structural formula (I).

Specific compounds of structural formula (I) include the following:

| | GN Number |
|---|---|
| 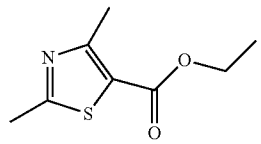 | 1 |
| 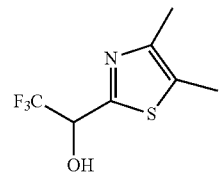 | 4 |
| 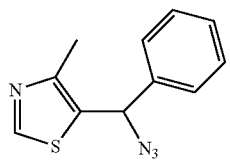 | 9 |
| 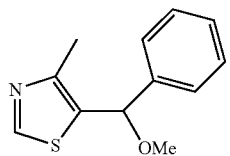 | 11 |
| 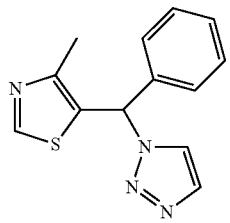 [SMILES: Cc1ncsc1C(c1ccccc1)n1ccnn1] | 14 |
| 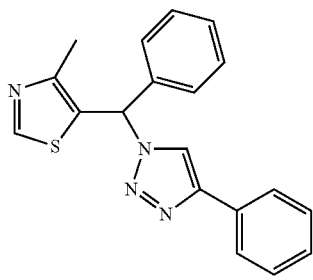 | 8 |

-continued

| | GN Number |
|---|---|
| 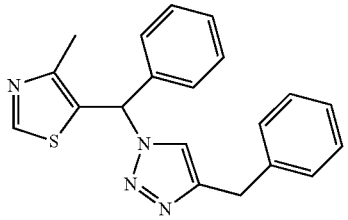 [SMILES: Cc1ncsc1C(c1ccccc1)n1cc(Cc2ccccc2)nn1] | 13 |
| 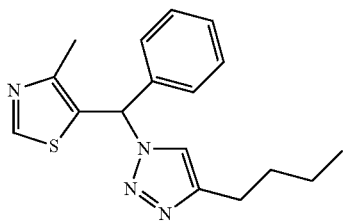 [SMILES: CCCCc1cn(C(c2ccccc2)c2scnc2C)nn1] | 7 |
| 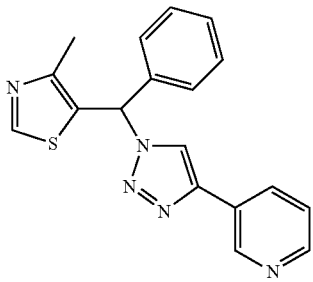 [SMILES: Cc1ncsc1C(c1ccccc1)n1cc(-c2cccnc2)nn1] | 12 |
| 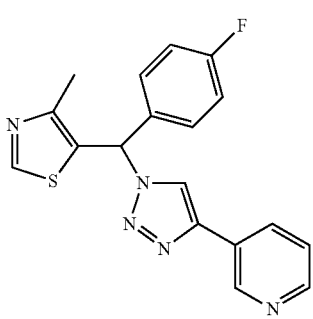 [SMILES: Cc1ncsc1C(c1ccc(F)cc1)n1cc(-c2cccnc2)nn1] | F-12 |
| 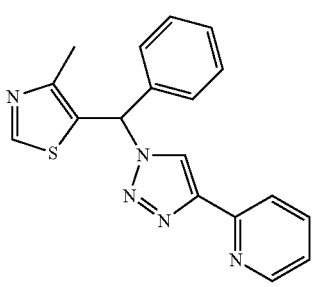 [SMILES: Cc1ncsc1C(c1ccccc1)n1cc(-c2ccccn2)nn1] | 18 |
| 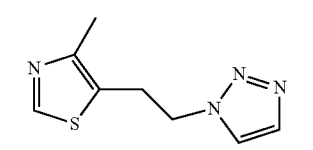 | 16 |

| | GN Number |
|---|---|
| 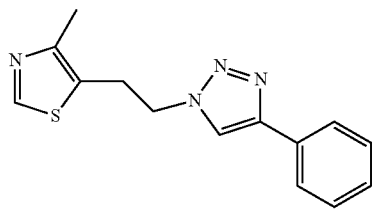 [SMILES: Cc1ncsc1CCn1cc(-c2ccccc2)nn1] | 20 |
| 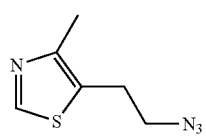 | 26 |
| 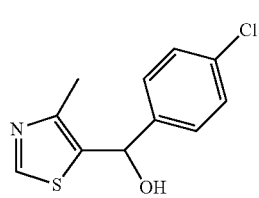 | 21 |
| 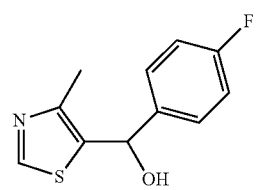 | 22 |
| 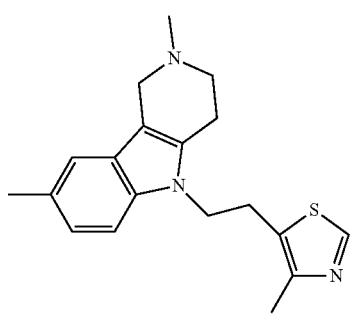 [SMILES: Cc1ccc2c(c1)c1c(n2CCc2scnc2C)CCN(C)C1] | 23 |
| 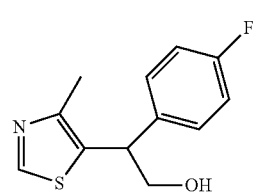 [SMILES: Cc1ncsc1C(CO)c1ccc(F)cc1] | 27 |
| 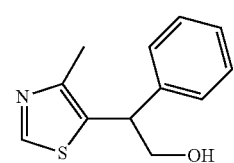 | 28 |
| | GN Number |
|---|---|
| 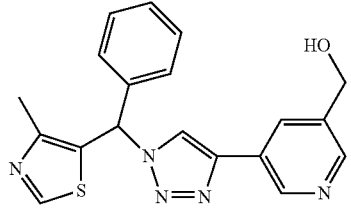 [SMILES: Cc1ncsc1C(c1ccccc1)n1cc(-c2cncc(CO)c2)nn1] | 31 |
| 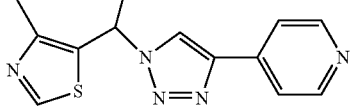 | 32 |
| 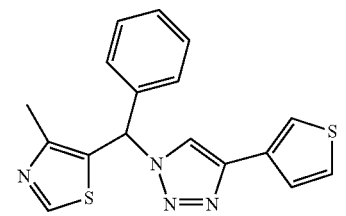 [SMILES: Cc1ncsc1C(c1ccccc1)n1cc(-c2ccsc2)nn1] | 33 |
| 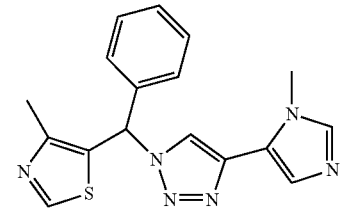 [SMILES: Cc1ncsc1C(c1ccccc1)n1cc(-c2cncn2C)nn1] | 34 |
| 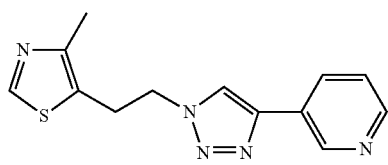 [SMILES: Cc1ncsc1CCn1cc(-c2cccnc2)nn1] | 35 |
| 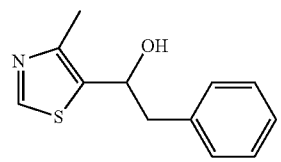 | 36 |

| GN Number |
|---|
| 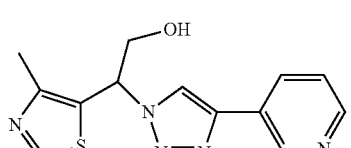 37 |
| 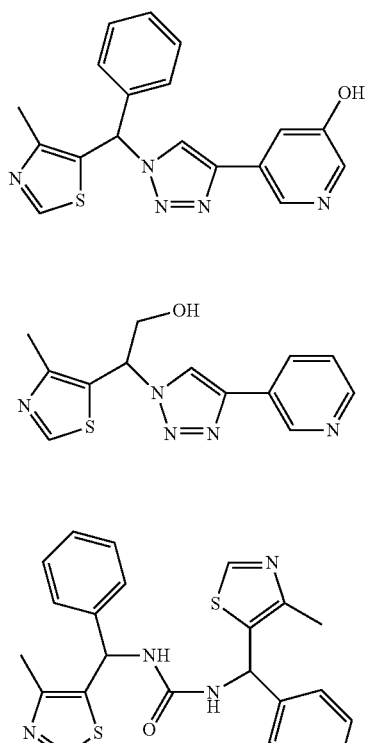 38 |
| 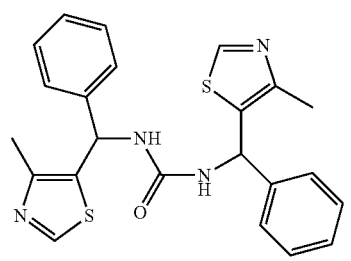 [SMILES: Cc1ncsc1C(NC(=O)NC(c1ccccc1)c1scnc1C)c1ccccc1] 39 |
| GN Number |
|---|
| 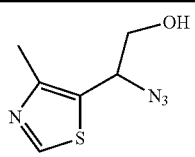 40 |
| 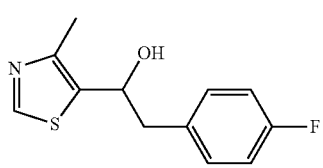 [SMILES: Cc1ncsc1C(O)Cc1ccc(F)cc1] 43 |
| 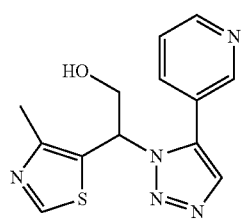 [SMILES: Cc1ncsc1C(CO)n1nncc1-c1cccnc1] 47 |
The following synthetic scheme illustrates the preparation of compounds of structural formula (I), such as compounds GN-27, 28, 36, 38, 40, 43 listed above.
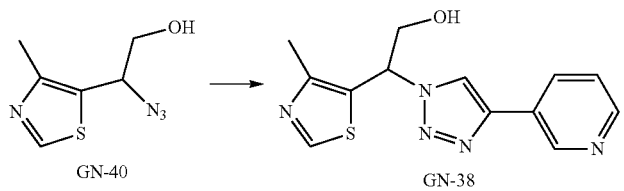
GN-40 → GN-38
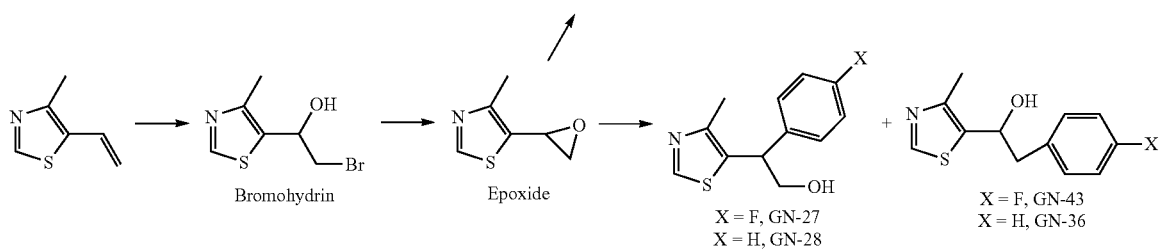
Bromohydrin → Epoxide → X = F, GN-27; X = H, GN-28 + X = F, GN-43; X = H, GN-36

More particularly, the compounds of structural formula (I) were prepared as follows.
Click Products from AR-N₃
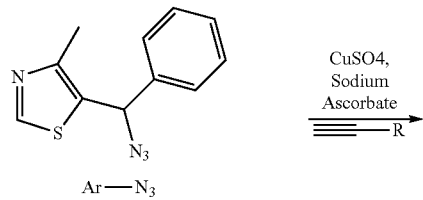
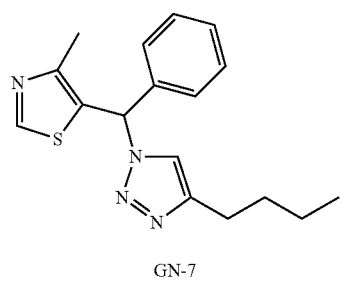
GN-7
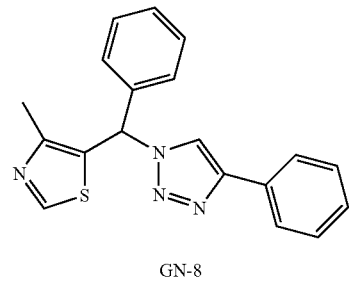
GN-8
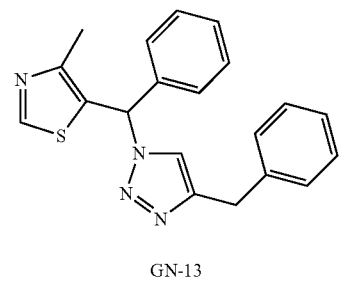
GN-13
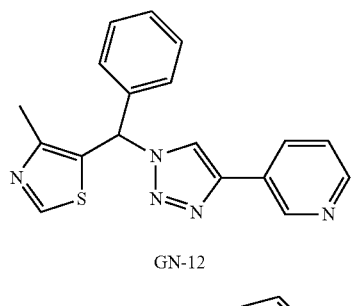
GN-12
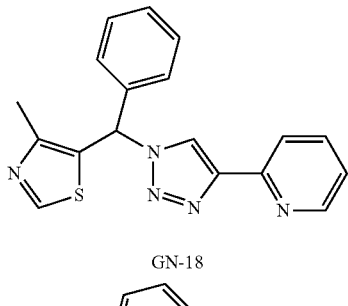
GN-18
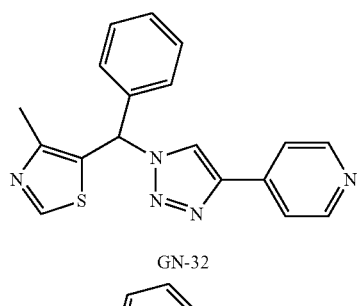
GN-32
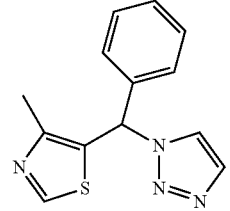
GN-14
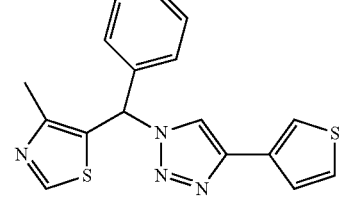
GN-33
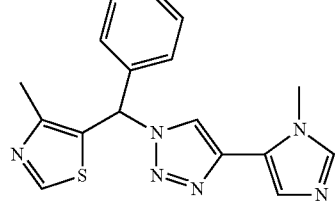
GN-34
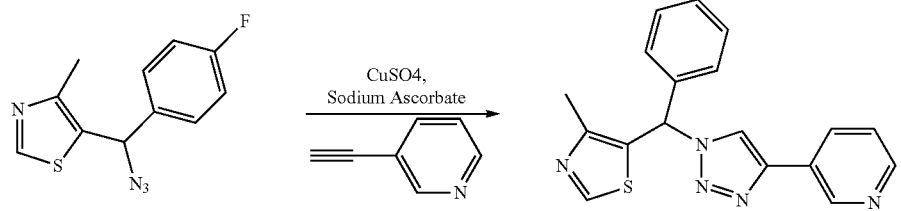
GN-F-12
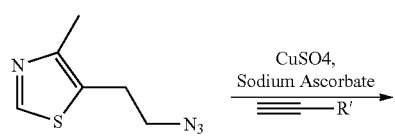

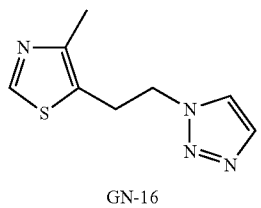
GN-16

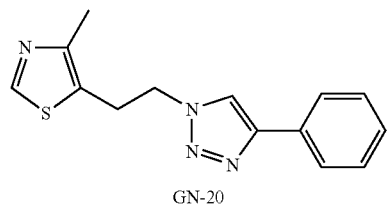
GN-20

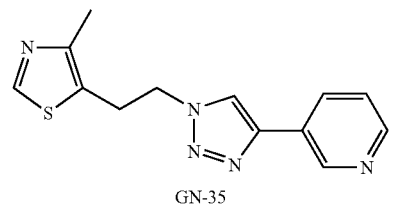
GN-35

Standard click chemistry procedure: Azide (1 equiv.) and alkyne (1 equiv.) were dissolved in t-butyl alcohol (t-BuOH) and water (1:1), then sodium ascorbate (0.2 equiv.) and copper sulfate pentahydrate ($CuSO_4.5H_2O$) (0.1 equiv.) were added. The reaction mixture was stirred overnight and diluted with ethyl acetate, washed with water, the organic phase was separated and concentrated, and the crude product was purified by column chromatography (dichloromethane (DCM)/methanol (MeOH).

GN-7: $^1$H-NMR (Acetone-$d_6$, 400 MHz): δ 8.92 (s, 1H), 7.83 (s, 1H), 7.48 (s, 1H), 7.35-7.41 (m, 3H), 7.27-7.28 (m, 2H), 2.68 (t, 2H, J=8.0 Hz), 2.36 (s, 3H), 1.58-1.66 (m, 2H), 1.29-1.38 (m, 2H), 0.88 (t, 3H, J=7.6 Hz).

GN-8: $^1$H-NMR (Acetone-$d_6$, 400 MHz): δ 9.02 (s, 1H), 8.48 (s, 1H), 7.92-7.94 (m, 2H), 7.58 (s, 1H), 7.30-7.45 (m, 8H), 2.41 (s, 3H); $^{13}$C-NMR (Acetone-$d_6$, 100 MHz): δ 147.98, 140.23, 131.82, 129.77, 129.55, 129.48, 128.75, 127.74, 126.29, 121.31, 61.47, 15.47.

GN-12: $^1$H-NMR (DMSO-$d_6$, 400 MHz): δ 9.10 (bs, 1H), 9.03 (s, 1H), 8.83 (s, 1H), 8.54 (bs, 1H), 8.25 (d, 1H, J=8.0 Hz), 7.67 (s, 1H), 7.29-7.49 (m, 6H), 2.45 (s, 3H); $^{13}$C-NMR (DMSO-$d_6$, 100 MHz): 6153.98, 151.42, 149.12, 146.58, 143.77, 139.09, 132.71, 129.48, 129.08, 128.76, 126.87, 126.41, 124.08, 122.18, 59.87, 15.12.

GN-F-12: $^1$H-NMR (CDCl$_3$, 400 MHz): δ 8.99 (s, 1H), 8.77 (s, 1H), 8.56 (d, 1H, J=3.6 Hz), 8.18-8.21 (m, 1H), 7.88 (s, 1H), 7.34-7.37 (m, 2H), 7.17-7.20 (m, 2H), 7.06-7.11 (m, 2H), 2.44 (s, 3H); $^{13}$C-NMR (CDCl$_3$, 100 MHz): δ 163.97, 161.49, 152.59, 152.09, 149.33, 146.89, 144.89, 113.71, 113.68, 132.89, 128.79, 128.61, 128.53, 126.16, 123.60, 119.27, 116.26, 116.04, 60.42, 15.30.

GN-13: $^1$H-NMR (DMSO-$d_6$, 400 MHz): δ 8.98 (s, 1H), 7.97 (s, 1H), 7.53 (s, 1H), 7.17-7.41 (m, 10H), 4.01 (s, 2H), 2.31 (s, 3H); $^{13}$C-NMR (CDCl$_3$, 100 MHz): δ 153.82, 150.92, 146.33, 139.46, 139.36, 129.81, 128.99, 128.57, 128.52, 126.81, 126.29, 122.78, 59.37, 31.19, 15.05.

GN-14: $^1$H-NMR (Acetone-$d_6$, 400 MHz): δ 8.90 (s, 1H), 8.06 (d, 1H, J=0.8 Hz), 7.75 (s, 1H, J=0.8 Hz), 7.57 (s, 1H), 7.26-7.43 (m, 5H), 2.37 (s, 3H); $^{13}$C-NMR (Acetone-$d_6$, 100 MHz): δ 153.57, 152.41, 140.39, 134.11, 130.73, 129.73, 129.42, 127.71, 125.00, 61.00, 15.35.

GN-16: $^1$H-NMR (Acetone-$d_6$, 400 MHz): δ 8.70 (s, 1H), 7.83 (s, 1H), 7.62 (s, 1H), 4.68 (t, 2H, J=6.8 Hz), 3.45 (t, 2H, J=6.8 Hz), 2.18 (s, 3H); $^{13}$C-NMR (Acetone-$d_6$, 100 MHz): δ 151.12, 150.93, 133.81, 127.25, 125.13, 51.14, 27.68, 14.59.

GN-18: $^1$H-NMR (Acetone-$d_6$, 400 MHz): δ 8.95 (s, 1H), 8.55 (d, 1H, J=4.0 Hz), 8.51 (s, 1H), 8.15 (d, 1H, J=8.0 Hz), 7.85 (triple doublet, 1H, J=8.0 Hz, 1.6 Hz), 7.64 (s, 1H), 7.21-7.45 (m, 6H), 2.43 (s, 3H); $^{13}$C-NMR (Acetone-$d_6$, 100 MHz): δ 153.73, 152.61, 151.51, 150.42, 148.90, 140.03, 137.59, 130.37, 129.79, 129.51, 127.74, 123.69, 123.32, 120.34, 61.43, 15.43.

GN-20: $^1$H-NMR (CDCl$_3$, 400 MHz): δ 8.60 (s, 1H), 7.76-7.78 (m, 2H), 7.51 (s, 1H), 7.39-7.43 (m, 2H), 7.31-7.35 (m, 1H), 4.60 (t, 2H, J=6.8 Hz), 3.44 (t, 2H, J=6.8 Hz), 2.25 (s, 3H); $^{13}$C-NMR (CDCl$_3$, 100 MHz): δ 150.73, 150.32, 147.78, 130.32, 128.80, 128.20, 125.84, 125.69, 119.94, 51.06, 27.34, 14.58.

GN-32: $^1$H-NMR (CDCl$_3$, 400 MHz): δ 8.75 (s, 1H), 8.61 (d, 2H, J=4.8 Hz), 8.01 (s, 1H), 7.71 (d, 2H, J=5.6 Hz), 7.34-7.40 (m, 4H), 7.18-7.20 (m, 2H), 2.42 (s, 3H); $^{13}$C-NMR (CDCl$_3$, 100 MHz): δ 152.49, 151.94, 150.09, 145.12, 137.55, 137.39, 129.02, 128.99, 128.81, 126.46, 120.65, 119.73, 60.96, 15.18.

GN-33: $^1$H-NMR (CDCl$_3$, 400 MHz): 8.69 (s, 1H), 7.67 (s, 1H), 7.30-7.43 (m, 6H), 7.15 (bs, 2H), 2.39 (s, 3H).

GN-34: $^1$H-NMR (CDCl$_3$, 400 MHz): δ 8.75 (s, 1H), 7.70 (s, 1H), 7.50 (bs, 2H), 7.39-7.40 (m, 3H), 7.31 (s, 1H), 7.17-7.19 (m, 2H), 3.93 (s, 3H), 2.44 (s, 3H).

GN-35: $^1$H-NMR (CDCl$_3$, 400 MHz): δ 8.95 (s, 1H), 8.61 (s, 1H), 8.56 (d, 1H, J=3.6 Hz), 8.13-8.15 (m, 1H), 7.70 (s, 1H), 7.34-7.37 (m, 1H), 4.64 (t, 2H, J=6.8 Hz), 3.47 (t, 2H, J=6.8 Hz), 2.26 (s, 3H).

Synthesis of GN-37 and GN-31: GN-12 Analogues

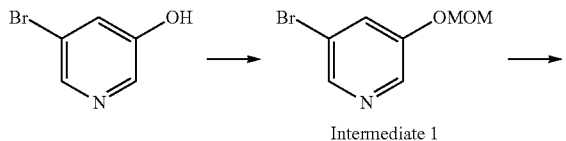
Intermediate 1

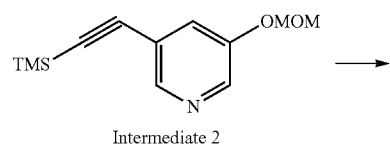
Intermediate 2

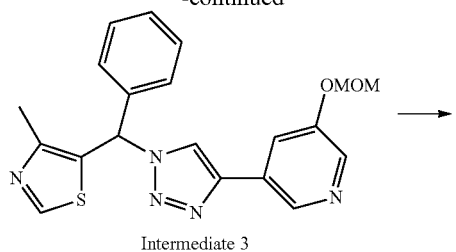

Intermediate 3 crude product was purified by column chromatography (DCM/MeOH 20:1, 1.15 g, 86%) ¹H-NMR (CDCl₃, 400 MHz): δ8.75 (s, 1H), 8.65 (s, 1H), 8.37 (s, 1H), 7.92 (s, 1H), 7.90 (s, 1H), 7.35-7.39 (m, 4H), 7.18-7.20 (m, 2H), 5.24 (s, 2H), 3.48 (s, 3H), 2.43 (s, 3H); ¹³C-NMR (CDCl₃, 100 MHz): δ153.40, 152.50, 151.92, 144.42, 140.07, 139.05, 137.69, 129.01, 128.96, 128.92, 126.79, 126.51, 119.70, 119.48, 94.31, 60.93, 56.03, 15.20.

GN-37: Intermediate 3 (230 mg, 0.58 mmol) was dissolved in a hydrochloric acid/isopropyl alcohol (HCl/i-PrOH) solution (1.5M, 5.0 mL) and heated at 70° C. for 1 hour. The solvent was removed, and the residue was dissolved in ethyl acetate (AcOEt) and washed with aqueous sodium bicarbonate (NaHCO₃). The organic phase was separated and concentrated, and the crude product was purified column chromatography (DCM/MeOH, 15:1). The product was obtained as white solid (170 mg, 83%). ¹H-NMR (Acetone-d₆, 400 MHz): δ 9.11 (bs, 1H), 8.93 (s, 1H), 8.61 (s, 1H), 8.59 (s, 1H), 8.17 (d, 1H, J=2.8 Hz), 7.76 (t, 1H, J=2.4 Hz), 7.60 (s, 1H), 7.35-7.46 (m, 5H), 2.41 (s, 3H); ¹³C-NMR (Acetone-d₆, 100 MHz): δ 154.63, 153.77, 152.72, 145.09, 140.14, 139.11, 138.41, 130.41, 129.83, 129.56, 128.41, 127.78, 122.09, 119.22, 61.50, 15.43.

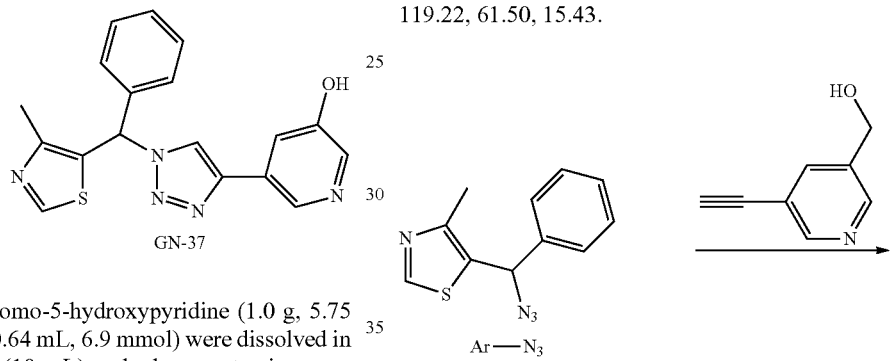

GN-37

Intermediate 1: 3-Bromo-5-hydroxypyridine (1.0 g, 5.75 mmol) and MOM-Br (0.64 mL, 6.9 mmol) were dissolved in tetrahydrofuran (THF) (10 mL), anhydrous potassium carbonate (K₂CO₃) (1.5 g, 10.9 mmol) was added, the reaction mixture was stirred overnight. After filtration and concentration, the product was purified by column chromatography (SiO₂, hexane/ethyl acetate 3:1), product was obtained as colorless oil (1.1 g, 88%). ¹H-NMR (CDCl₃, 400 MHz): δ 8.34 (s, 1H), 8.33 (s, 1H), 7.56 (t, 1H, J=2.4 Hz), 5.19 (s, 2H), 3.49 (s, 3H); ¹³C-NMR (CDCl₃, 100 MHz): δ153.70, 143.96, 137.81, 125.72, 120.18, 94.66, 56.27.

Intermediate 2: Intermediate 1 (1.0 g, 4.6 mmol), cuprous iodide (CuI) (44 mg, 0.23 mmol), Pd(Ph₃P)₂Cl₂(162 mg, 0.23 mmol) were placed in a flask and filled with argon. THF (10 mL) was added using a syringe followed by triethylamine (NEt₃) (3.0 mL, 21 mmol) and ethynyltrimethylsilane (0.7 mL, 5.1 mmol). The reaction mixture was stirred overnight. Most of the solvent was removed and the residue was purified by column chromatography (SiO₂, hexane/ethyl acetate 5:1), product was obtained as yellow oil (0.85 g, 81%). ¹H-NMR (CDCl₃, 400 MHz): δ 8.32-8.35 (m, 2H), 7.43-7.44 (m, 2H), 5.19 (s, 2H), 3.48 (s, 3H), 0.26 (s, 9H); ¹³C-NMR (CDCl₃, 100 MHz): δ152.65, 145.97, 139.21, 125.18, 120.38, 101.15, 98.03, 94.53, 56.17.

Intermediate 3: Azide (783 mg, 3.4 mmol) and intermediate 2 (0.8 g, 3.4 mmol) were dissolved in a mixture of MeOH and water (2:1, 5 mL), then K₂CO₃ (484 mg, 3.5 mmol), CuSO₄.5H₂O (170 mg, 0.68 mmol), and sodium ascorbate (272 mg, 0.68 mmol) were added. The reaction mixture was stirred at room temperature overnight. Most of the solvent was removed under reduced pressure, then the residue was dissolved in dichloromethane (DCM) and washed with water, the organic phase was separated and concentrated, and the

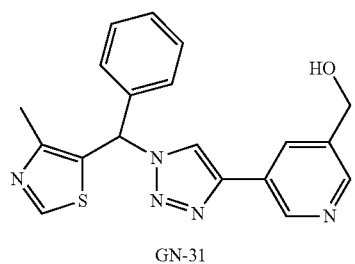

GN-31

GN-31: GN-31 was prepared using standard click chemistry procedure described above. ¹H-NMR (CDCl₃, 400 MHz): δ 8.82 (s, 1H), 8.73 (s, 1H), 8.48 (s, 1H), 8.19 (s, 1H), 7.87 (s, 1H), 7.35-7.39 (m, 3H), 7.32 (s, 1H), 7.14-7.17 (m, 2H), 4.74 (s, 2H), 2.41 (s, 3H); ¹³C-NMR (CDCl₃, 100 MHz): δ 152.72, 152.06, 147.77, 145.63, 144.71, 137.72, 137.00, 131.84, 129.25, 129.22, 129.11, 126.69, 126.00, 119.81, 61.95, 61.16, 15.35.

Preparation of Additional Compounds of Structural Formula (I)

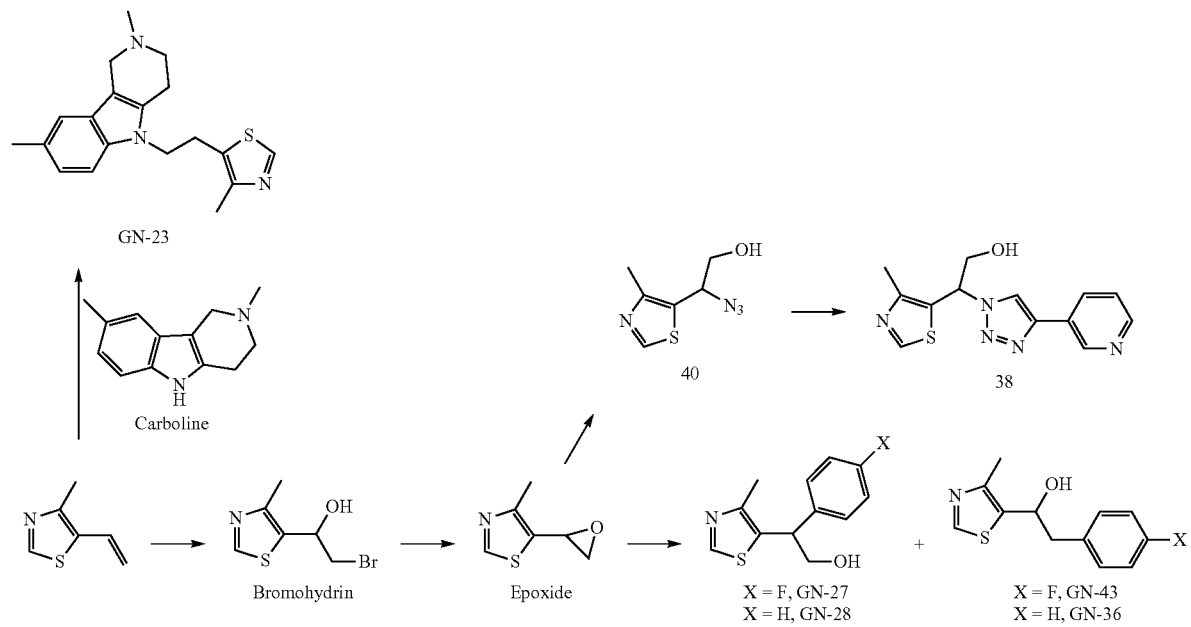

Bromohydrin: 4-Methyl-5-vinylthiazole (900 mg, 7.19 mmol) was dissolved in a mixture of dioxane (2.5 mL), H$_2$O (5 mL) and acetic acid (430 mg), N-bromo-succinimide (NBS) (1.4 g, 7.9 mmol) was added in 3 portions. The reaction mixture was stirred at room temperature for 1 hour, then diluted with ethyl acetate (50 mL). Organic phase was separated and concentrated, and the product was obtained as colorless oil by column chromatography purification (SiO$_2$, hexane/ethyl acetate 1.5:1, 900 mg, 52%). $^1$H-NMR (CDCl$_3$, 400 MHz): δ 8.63 (s, 1H), 5.22 (t, 1H, J=6.8 Hz), 3.53-3.62 (m, 2H), 2.71 (s, 1H), 2.36 (s, 3H).

Epoxide: Bromohydrin (650 mg, 2.94 mmol) was dissolved in MeOH (10 mL). K$_2$CO$_3$ (1.2 g, 8.8 mmol) was added, and the reaction mixture was stirred at room temperature for 1 hour. A majority of the solvent was removed, and the residue was diluted with ethyl acetate (50 mL). After filtration and concentration, a product of sufficient purity was obtained for the next step reaction. $^1$H-NMR (CDCl$_3$, 400 MHz): δ 8.63 (s, 1H), 4.10 (t, 1H, J=3.6 Hz), 3.22-3.24 (m, 1H), 2.91-2.93 (m, 1H), 2.53 (s, 3H); $^{13}$C-NMR (CDCl$_3$, 100 MHz): δ 151.90, 150.69, 128.97, 51.25, 46.80, 14.95.

GN-28 and GN-36: Crude epoxide (1.0 g, 7.1 mmol) was dissolved in anhydrous THF (10 mL) and added dropwise to a phenylmagnesium bromide solution (1M in THF, 10 mL) at 4° C. The reaction mixture was stirred overnight at room temperature, quenched with aqueous ammonium chloride (NH$_4$Cl) solution, and extracted with ethyl acetate. The organic phase was separated, and concentrated GN-28 and GN-36 were separated and purified by column chromatography (SiO$_2$, hexane/ethyl acetate 1:1). GN-28 (major product): $^1$H-NMR (CDCl$_3$, 400 MHz): δ 8.43 (s, 1H), 7.25-7.29 (m, 2H), 7.17-7.21 (m, 3H), 4.38 (t, 1H, J=6.4 Hz), 3.95-4.05 (m, 2H), 3.87 (s, 1H), 2.28 (s, 3H). GN-36: $^1$H-NMR (CDCl$_3$, 400 MHz): δ 8.43 (s, 1H), 7.28-7.33 (m, 5H), 4.83 (t, 1H, J=6.4 Hz), 3.29 (s, 1H), 3.10-3.19 (m, 2H), 2.17 (s, 3H); $^{13}$C-NMR (CDCl$_3$, 100 MHz): δ 150.07, 149.89, 143.23, 128.42, 127.82, 126.95, 125.77, 74.36, 36.08, 14.63.

GN-27 and GN-43: GN-27 and GN-43 were synthesized using the procedure described above from epoxide and 4-fluoro-phenylmagnesium bromide. GN-27 (major product): $^1$H-NMR (CDCl$_3$, 400 MHz): δ 8.45 (s, 1H), 7.16-7.19 (m, 2H), 6.30-6.97 (m, 2H), 4.37 (t, 1H, J=6.4 Hz), 3.94-4.03 (m, 2H), 2.26 (s, 3H); $^{13}$C-NMR (CDCl$_3$, 100 MHz): δ 162.66, 160.22, 150.07, 148.95, 136.24, 136.21, 131.98, 129.26, 129.18, 115.36, 115.14, 66.22, 45.16, 14.82. GN-43: $^1$H-NMR (CDCl$_3$, 400 MHz): δ 8.39 (s, 1H), 7.21-7.24 (m, 2H), 6.96-6.99 (m, 2H), 4.81 (t, 1H, J=6.4 Hz), 3.04-3.16 (m, 2H), 2.12 (s, 3H).

GN-40: Epoxide (400 mg, 2.8 mmol) was dissolved in acetonitrile and water (1:1, 10 mL) sodium azide (NaN$_3$) (553 mg, 8.4 mmol) was added, and the reaction mixture was refluxed for 1 hour. A majority of the solvent was removed under reduced pressure. The residue was dissolved in DCM (20 mL) and washed with water. The organic phase was separated and concentrated, and GN-40 was purified by column chromatography (SiO$_2$, hexane/ethyl acetate 1:1, 410 mg, yellow solid, 61%). $^1$H-NMR (CDCl$_3$, 400 MHz): δ 8.71 (s, 1H), 4.98-5.00 (m, 1H), 4.80 (bs, 1H), 3.76-3.87 (m, 2H), 2.49 (s, 3H); $^{13}$C-NMR (CDCl$_3$, 100 MHz): δ 152.35, 150.67, 126.97, 65.28, 59.85, 15.01.

GN-38: GN-38 was prepared according to the standard click chemistry procedure described above from GN-40 and 3-ethynyl pyridine. The product was purified by column chromatography (SiO$_2$, DCM/MeOH). $^1$H-NMR (CDCl$_3$, 400 MHz): δ 9.05 (s, 1H), 9.01 (s, 1H), 8.80 (s, 1H), 8.52 (d, 1H, J=3.6 Hz), 8.21 (d, 1H, J=8.0 Hz), 7.45 (dd, 1H, J=5.2 Hz, 7.6 Hz), 6.22-6.25 (m, 1H), 4.15-4.20 (m, 1H), 4.04-4.08 (m, 1H), 2.44 (m, 3H); $^{13}$C-NMR (CDCl$_3$, 100 MHz): δ 153.49, 151.44, 148.90, 146.37, 143.36, 132.42, 126.56, 126.36, 123.96, 121.73, 63.87, 58.99, 15.07.

GN-23: Carboline (500 mg, 2.5 mmol) was dissolved in dimethyl sulfoxide (DMSO) (5 mL), and sodium hydride (NaH) (120 mg, 60%, 3 mmol) was added and stirred for 5 minutes. 4-Methyl-5-vinylthiazole (2.86 mL, 25 mmol) was added, and the reaction mixture was heated at 90° C. for 5 hours. The reaction was quenched with MeOH (0.5 mL), and the solvents were evaporated under high vacuum. The residue was dissolved in DCM (20 mL), washed with water, and the organic phase was separated and concentrated. The product was purified by column chromatography (SiO$_2$, DCM/MeOH 25:1, 0.1% HOAc, 350 mg, yellow solid, 36%), GN-23 was obtained as the acetic acid (AcOH) salt. $^1$H-NMR (Acetone-d$_6$, 400 MHz): δ 8.67 (s, 1H), 7.18-7.22 (m, 2H), 6.93 (d, 1H, J=8.4 Hz), 4.28 (t, 2H, J=6.4 Hz), 3.82 (s, 2H), 3.23 (t, 2H, J=6.4 Hz), 2.92 (t, 2H, J=6.0 Hz), 2.56-2.62 (m, 5H), 2.38 (s, 3H), 1.96 (s, 3H), 1.91 (s, 3H); $^{13}$C-NMR (Acetone-d$_6$, 100 MHz): δ 172.71, 150.34, 150.75, 135.69, 133.51, 128.69, 128.35, 126.83, 123.21, 118.16, 109.16, 106.11, 52.23, 51.42, 44.69, 44.22, 27.10, 21.84, 21.48, 20.89, 14.43.

GN-46, Metabolite of GM-30

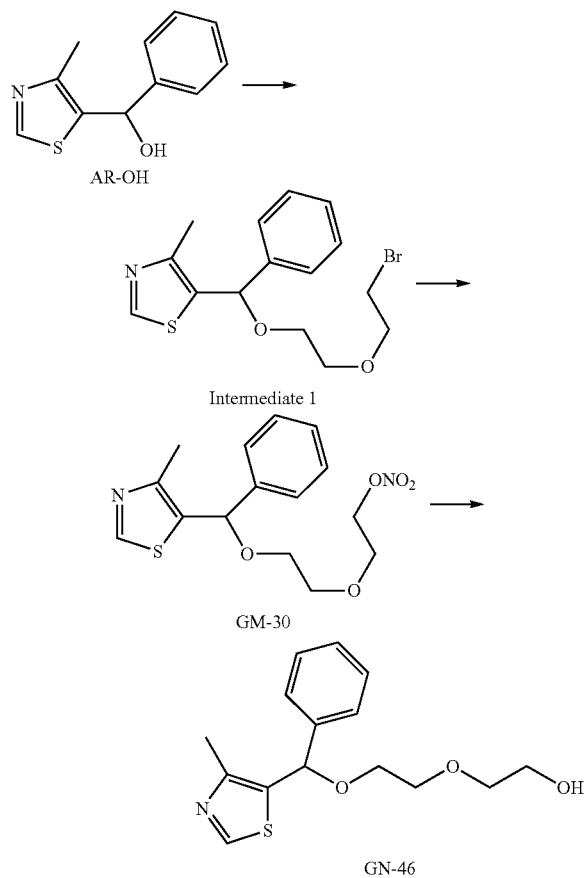

Intermediate 1: To a solution of (±)-1-(4-methyl-5-thiazolyl)-1-phenyl-methanol (500 mg, 2.4 mmol) in DMF (5 mL) was added NaH (117 mg, 2.92 mmol). The reaction mixture was stirred at room temperature for 15 minutes, then bis(2-bromomethyl)ether (2.2 g, 9.6 mmol) was added, and the reaction mixture was stirred for another 3 hours. The reaction was quenched with MeOH (1 mL), then a majority of the solvent was removed. The residue was dissolved in ethyl acetate (50 mL), washed with water, and the organic phase was separated and concentrated. Crude product was purified by column chromatography (SiO$_2$, hexane/ethyl acetate 2:1), intermediate 1 was obtained as colorless oil (740 mg, 86%). $^1$H-NMR (CDCl$_3$, 300 MHz): δ 8.65 (s, 1H), 7.26-7.39 (m, 5H), 5.75 (s, 1H), 3.81 (t, 2H, J=6.1 Hz), 3.62-3.73 (m, 4H), 3.46 (t, 2H, J=6.1 Hz), 2.45 (s, 3H).

GM-30: Silver nitrate (2.0 g, 11.8 mmol) was added to a solution of intermediate 1 (1.1 g, 3.1 mmol) in acetonitrile (CH$_3$CN) (15 mL). The reaction mixture was refluxed for 2 hours, then diluted with ethyl acetate (50 mL). After filtration and concentration, the crude product was purified by column chromatography (SiO$_2$, hexane/ethyl acetate 1.5:1). GM-30 was obtained as slightly yellow oil (720 mg, 69%). $^1$H-NMR (CDCl$_3$, 400 MHz): δ 8.62 (s, 1H), 7.26-7.38 (m, 5H), 4.59 (t, 2H, J=4.4 Hz), 3.77 (t, 2H, J=4.4 Hz), 3.67-3.69 (m, 2H), 3.62-3.64 (m, 2H), 2.45 (s, 3H); $^{13}$C-NMR (CDCl$_3$, 100 MHz): δ 151.40, 149.46, 140.63, 133.55, 128.49, 127.99, 126.39, 77.22, 72.03, 70.69, 68.26, 67.15.

GN-46: To a solution of GM-30 (70 mg, 0.21 mmol) in anhydrous THF (5 mL) was added lithium aluminum hydride (LiAlH$_4$) (35 mg, 0.85 mmol). The reaction mixture was refluxed for 1 hour, then the reaction was quenched with MeOH, concentrated, the residue was dissolved in AcOEt, and washed with H$_2$O. The product was purified by column chromatography (Hexane/Acetone 2:1, 25%). $^1$H-NMR (CDCl$_3$, 400 MHz): δ 8.64 (s, 1H), 7.26-7.38 (m, 5H), 5.70 (s, 1H), 3.70-3.73 (m, 4H), 3.60-3.66 (m, 4H), 2.45 (s, 3H); $^{13}$C-NMR (CDCl$_3$, 100 MHz): δ 151.60, 149.56, 140.71, 133.65, 128.65, 128.16, 126.51, 77.39, 72.38, 70.37, 68.49, 61.80, 15.52.

Analytical Data for Compounds of Structural Formula (I)

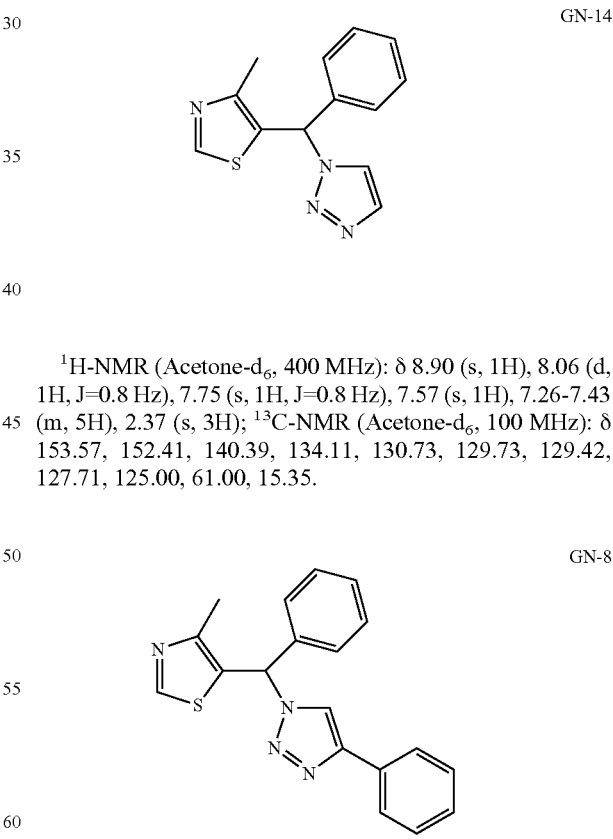

$^1$H-NMR (Acetone-d$_6$, 400 MHz): δ 8.90 (s, 1H), 8.06 (d, 1H, J=0.8 Hz), 7.75 (s, 1H, J=0.8 Hz), 7.57 (s, 1H), 7.26-7.43 (m, 5H), 2.37 (s, 3H); $^{13}$C-NMR (Acetone-d$_6$, 100 MHz): δ 153.57, 152.41, 140.39, 134.11, 130.73, 129.73, 129.42, 127.71, 125.00, 61.00, 15.35.

$^1$H-NMR (Acetone-d$_6$, 400 MHz): δ 9.02 (s, 1H), 8.48 (s, 1H), 7.92-7.94 (m, 2H), 7.58 (s, 1H), 7.30-7.45 (m, 8H), 2.41 (s, 3H); $^{13}$C-NMR (Acetone-d$_6$, 100 MHz): δ 147.98, 140.23, 131.82, 129.77, 129.55, 129.48, 128.75, 127.74, 126.29, 121.31, 61.47, 15.47.

GN-13

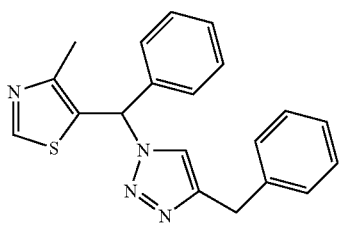

¹H-NMR (DMSO-d₆, 400 MHz): δ 8.98 (s, 1H), 7.97 (s, 1H), 7.53 (s, 1H), 7.17-7.41 (m, 10H), 4.01 (s, 2H), 2.31 (s, 3H); ¹³C-NMR (CDCl₃, 100 MHz): δ 153.82, 150.92, 146.33, 139.46, 139.36, 129.81, 128.99, 128.57, 128.52, 126.81, 126.29, 122.78, 59.37, 31.19, 15.05.

GN-7

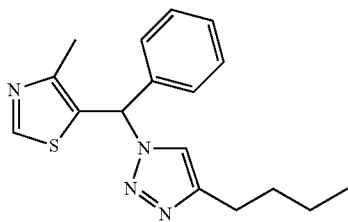

¹H-NMR (Acetone-d₆, 400 MHz): δ 8.92 (s, 1H), 7.83 (s, 1H), 7.48 (s, 1H), 7.35-7.41 (m, 3H), 7.27-7.28 (m, 2H), 2.68 (t, 2H, J=8.0 Hz), 2.36 (s, 3H), 1.58-1.66 (m, 2H), 1.29-1.38 (m, 2H), 0.880 (t, 3H, J=7.6 Hz).

GN-12

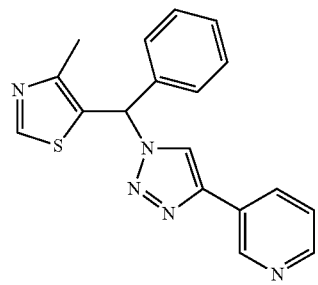

¹H-NMR (DMSO-d₆, 400 MHz): δ 9.10 (bs, 1H), 9.03 (s, 1H), 8.83 (s, 1H), 8.54 (bs, 1H), 8.25 (d, 1H, J=8.0 Hz), 7.67 (s, 1H), 7.29-7.49 (m, 6H), 2.45 (s, 3H); ¹³C-NMR (DMSO-d₆, 100 MHz): δ 153.98, 151.42, 149.12, 146.58, 143.77, 139.09, 132.71, 129.48, 129.08, 128.76, 126.87, 126.41, 124.08, 122.18, 59.87, 15.12.

GN-F-12

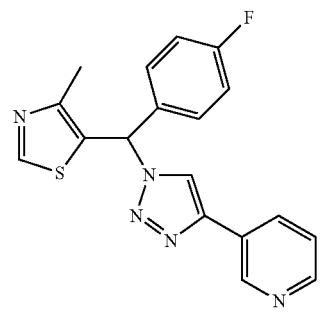

¹H-NMR (CDCl₃, 400 MHz): δ 8.99 (s, 1H), 8.77 (s, 1H), 8.56 (d, 1H, J=3.6 Hz), 8.18-8.21 (m, 1H), 7.88 (s, 1H), 7.34-7.37 (m, 2H), 7.17-7.20 (m, 2H), 7.06-7.11 (m, 2H), 2.44 (s, 3H); ¹³C-NMR (CDCl₃, 100 MHz): δ 163.97, 161.49, 152.59, 152.09, 149.33, 146.89, 144.89, 113.71, 113.68, 132.89, 128.79, 128.61, 128.53, 126.16, 123.60, 119.27, 116.26, 116.04, 60.42, 15.30.

GN-18

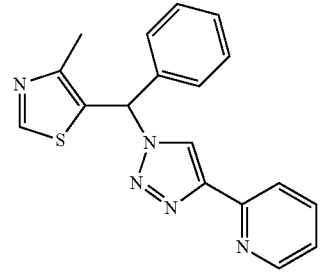

¹H-NMR (Acetone-d₆, 400 MHz): δ 8.95 (s, 1H), 8.55 (d, 1H, J=4.0 Hz), 8.51 (s, 1H), 8.15 (d, 1H, J=8.0 Hz), 7.85 (triple doublet, 1H, J=8.0 Hz, 1.6 Hz), 7.64 (s, 1H), 7.21-7.45 (m, 6H), 2.43 (s, 3H); ¹³C-NMR (Acetone-d₆, 100 MHz): δ 153.73, 152.61, 151.51, 150.42, 148.90, 140.03, 137.59, 130.37, 129.79, 129.51, 127.74, 123.69, 123.32, 120.34, 61.43, 15.43.

GN-16

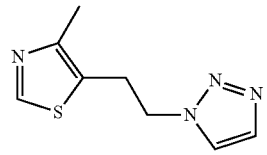

¹H-NMR (Acetone-d₆, 400 MHz): δ 8.70 (s, 1H), 7.83 (s, 1H), 7.62 (s, 1H), 4.68 (t, 2H, J=6.8 Hz), 3.45 (t, 2H, J=6.8 Hz), 2.18 (s, 3H); ¹³C-NMR (Acetone-d₆, 100 MHz): δ 151.12, 150.93, 133.81, 127.25, 125.13, 51.14, 27.68, 14.59.

GN-20

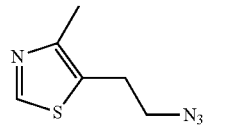

¹H-NMR (CDCl₃, 400 MHz): δ 8.60 (s, 1H), 7.76-7.78 (m, 2H), 7.51 (s, 1H), 7.39-7.43 (m, 2H), 7.31-7.35 (m, 1H), 4.60 (t, 2H, J=6.8 Hz), 3.44 (t, 2H, J=6.8 Hz), 2.25 (s, 3H).

GN-26

¹H-NMR (Acetone-d₆, 400 MHz): δ 8.74 (s, 1H), 3.59 (t, 2H, J=6.8 Hz), 3.09 (t, 2H, J=6.8 Hz), 2.38 (s, 3H); ¹³C-NMR (Acetone-d₆, 100 MHz): δ 150.75, 128.19, 52.72, 26.54, 14.96.

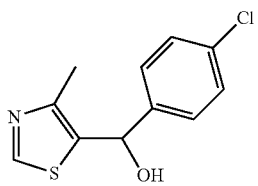

GN-21

¹H-NMR (CDCl₃, 400 MHz): δ 8.56 (s, 1H), 7.33 (s, 4H), 6.07 (s, 1H), 2.38 (s, 3H).

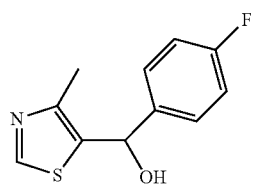

GN-22

¹H-NMR (CDCl₃, 400 MHz): 8.49 (s, 1H), 7.35 (dd, 2H, J=6.4 Hz, 8.4 Hz), 7.03 (t, 2H, J=8.4 Hz), 6.04 (s, 1H), 2.32 (s, 3H).

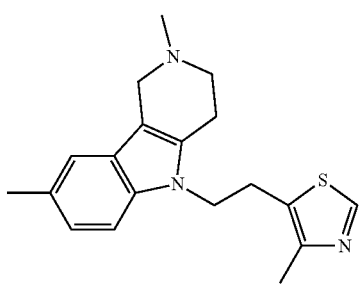

GN-23

AcOH Salt. ¹H-NMR (Acetone-d₆, 400 MHz): δ 8.67 (s, 1H), 7.18-7.22 (m, 2H), 6.93 (d, 1H, J=8.4 Hz), 4.28 (t, 2H, J=6.4 Hz), 3.82 (s, 2H), 3.23 (t, 2H, J=6.4 Hz), 2.92 (t, 2H, J=6.0 Hz), 2.56-2.62 (m, 5H), 2.38 (s, 3H), 1.96 (s, 3H), 1.91 (s, 3H); ¹³C-NMR (Acetone-d₆, 100 MHz): δ 172.71, 150.34, 150.75, 135.69, 133.51, 128.69, 128.35, 126.83, 123.21, 118.16, 109.16, 106.11, 52.23, 51.42, 44.69, 44.22, 27.10, 21.84, 21.48, 20.89, 14.43.

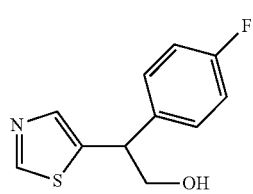

GN-27

¹H-NMR (CDCl₃, 400 MHz): δ 8.45 (s, 1H), 7.16-7.19 (m, 2H), 6.30-6.97 (m, 2H), 4.37 (t, 1H, J=6.4 Hz), 3.94-4.03 (m, 2H), 2.26 (s, 3H); ¹³C-NMR (CDCl₃, 100 MHz): δ 162.66, 160.22, 150.07, 148.95, 136.24, 136.21, 131.98, 129.26, 129.18, 115.36, 115.14, 66.22, 45.16, 14.82.

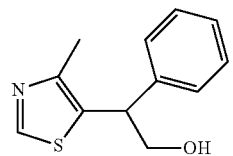

GN-28

¹H-NMR (CDCl₃, 400 MHz): δ 8.43 (s, 1H), 7.25-7.29 (m, 2H), 7.17-7.21 (m, 3H), 4.38 (t, 1H, J=6.4 Hz), 3.95-4.05 (m, 2H), 3.87 (s, 1H), 2.28 (s, 3H).

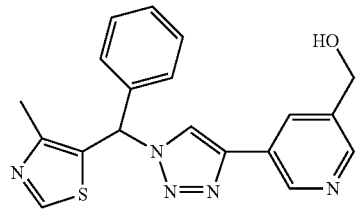

GN-31

¹H-NMR (CDCl₃, 400 MHz): δ 8.82 (s, 1H), 8.73 (s, 1H), 8.48 (s, 1H), 8.19 (s, 1H), 7.87 (s, 1H), 7.35-7.39 (m, 3H), 7.32 (s, 1H), 7.14-7.17 (m, 2H), 4.74 (s, 2H), 2.41 (s, 3H); ¹³C-NMR (CDCl₃, 100 MHz): δ 152.72, 152.06, 147.77, 145.63, 144.71, 137.72, 137.00, 131.84, 129.25, 129.22, 129.11, 126.69, 126.00, 119.81, 61.95, 61.16, 15.35.

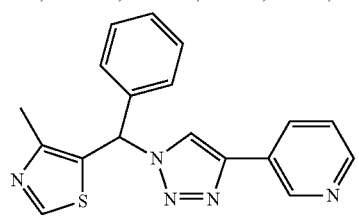

GN-32

¹H-NMR (CDCl₃, 400 MHz): δ 8.75 (s, 1H), 8.61 (d, 2H, J=4.8 Hz), 8.01 (s, 1H), 7.71 (d, 2H, J=5.6 Hz), 7.34-7.40 (m, 4H), 7.18-7.20 (m, 2H), 2.42 (s, 3H); ¹³C-NMR (CDCl₃, 100 MHz): δ 152.49, 151.94, 150.09, 145.12, 137.55, 137.39, 129.02, 128.99, 128.81, 126.46, 120.65, 119.73, 60.96, 15.18.

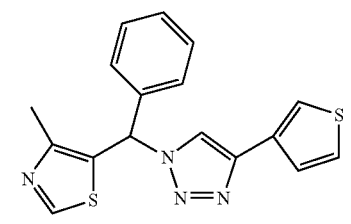

GN-33

¹H-NMR (CDCl₃, 400 MHz): δ 8.69 (s, 1H), 7.71 (s, 1H), 7.67 (s, 1H), 7.30-7.43 (m, 6H), 7.15 (bs, 2H), 2.39 (s, 3H).

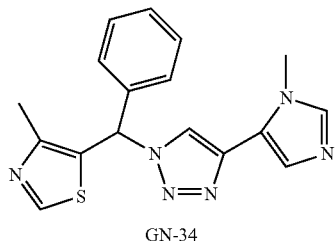 [SMILES: Cc1ncsc1C(c1ccccc1)n1cc(-c2cncn2C)nn1]

GN-34

¹H-NMR (CDCl₃, 400 MHz): δ 8.75 (s, 1H), 7.70 (s, 1H), 7.50 (bs, 2H), 7.39-7.40 (m, 3H), 7.31 (s, 1H), 7.17-7.19 (m, 2H), 3.93 (s, 3H), 2.44 (s, 3H).

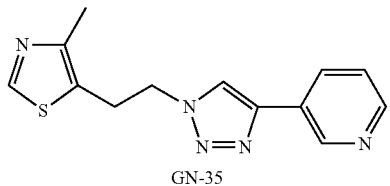 [SMILES: Cc1ncsc1CCn1cc(-c2cccnc2)nn1]

GN-35

¹H-NMR (CDCl₃, 400 MHz): δ 8.95 (s, 1H), 8.61 (s, 1H), 8.56 (d, 1H, J=3.6 Hz), 8.13-8.15 (m, 1H), 7.70 (s, 1H), 7.34-7.37 (m, 1H), 4.64 (t, 2H, J=6.8 Hz), 3.47 (t, 2H, J=6.8 Hz), 2.26 (s, 3H).

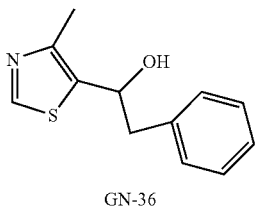

GN-36

¹H-NMR (CDCl₃, 400 MHz): δ 8.43 (s, 1H), 7.28-7.33 (m, 5H), 4.83 (t, 1H, J=6.4 Hz), 3.29 (s, 1H), 3.10-3.19 (m, 2H), 2.17 (s, 3H); ¹³C-NMR (CDCl₃, 100 MHz): δ 150.07, 149.89, 143.23, 128.42, 127.82, 126.95, 125.77, 74.36, 36.08, 14.63.

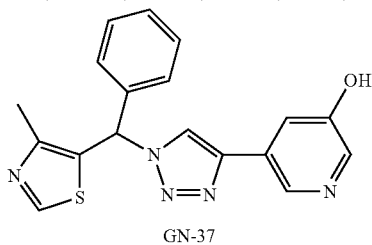 [SMILES: Cc1ncsc1C(c1ccccc1)n1cc(-c2cncc(O)c2)nn1]

GN-37

¹H-NMR (Acetone-d₆, 400 MHz): δ 9.11 (bs, 1H), 8.93 (s, 1H), 8.61 (s, 1H), 8.59 (s, 1H), 8.17 (d, 1H, J=2.8 Hz), 7.76 (t, 1H, J=2.4 Hz), 7.60 (s, 1H), 7.35-7.46 (m, 5H), 2.41 (s, 3H); ¹³C-NMR (Acetone-d₆, 100 MHz): δ 154.63, 153.77, 152.72, 145.09, 140.14, 139.11, 138.41, 130.41, 129.83, 129.56, 128.41, 127.78, 122.09, 119.22, 61.50, 15.43.

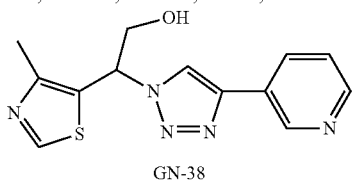

GN-38

¹H-NMR (CDCl₃, 400 MHz): δ 9.05 (s, 1H), 9.01 (s, 1H), 8.80 (s, 1H), 8.52 (d, 1H, J=3.6 Hz), 8.21 (d, 1H, J=8.0 Hz), 7.45 (dd, 1H, J=5.2 Hz, 7.6 Hz), 6.22-6.25 (m, 1H), 4.15-4.20 (m, 1H), 4.04-4.08 (m, 1H), 2.44 (m, 3H); ¹³C-NMR (CDCl₃, 100 MHz): δ 153.49, 151.44, 148.90, 146.37, 143.36, 132.42, 126.56, 126.36, 123.96, 121.73, 63.87, 58.99, 15.07.

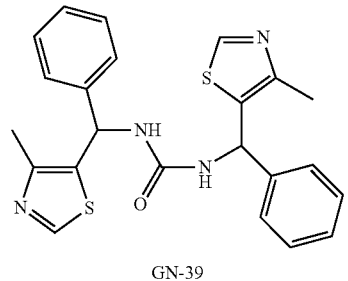 [SMILES: Cc1ncsc1C(NC(=O)NC(c1ccccc1)c1scnc1C)c1ccccc1]

GN-39

¹H-NMR (CDCl₃, 400 MHz): δ 8.46 (s, 1H), 7.24-7.29 (m, 2H), 7.14-7.17 (m, 2H), 6.19 (d, 1H, J=7.2 Hz), 5.80 (d, 1H, J=7.2 Hz), 2.25 (s, 3H); ¹³C-NMR (CDCl₃, 100 MHz): δ 156.02, 150.35, 149.27, 140.85, 134.70, 128.84, 127.97, 126.54, 51.37, 15.23.

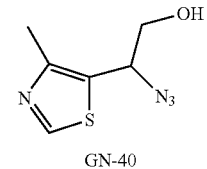

GN-40

¹H-NMR (CDCl₃, 400 MHz): δ 8.71 (s, 1H), 4.98-5.00 (m, 1H), 4.80 (bs, 1H), 3.76-3.87 (m, 2H), 2.49 (s, 3H); ¹³C-NMR (CDCl₃, 100 MHz): δ 152.35, 150.67, 126.97, 65.28, 59.85, 15.01.

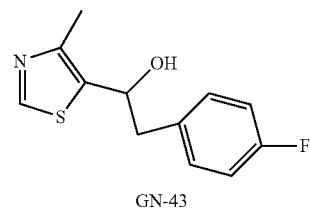 [SMILES: Cc1ncsc1C(O)Cc1ccc(F)cc1]

GN-43

¹H-NMR (CDCl₃, 400 MHz): δ 8.39 (s, 1H), 7.21-7.24 (m, 2H), 6.96-6.99 (m, 2H), 4.81 (t, 1H, J=6.4 Hz), 3.04-3.16 (m, 2H), 2.12 (s, 3H).

Neuroprotection in Primary Rat Neuron Cultures by Compounds of Structural Formula (I)

Neuroprotection by compounds of structural formula (I) in neurons using oxygen-glucose deprivation (OGD) followed by recovery for 24 hours in primary rat cortical neuron cultures, measured by LDH release and MTT viability was determined (FIG. 1).

Figure 1B:
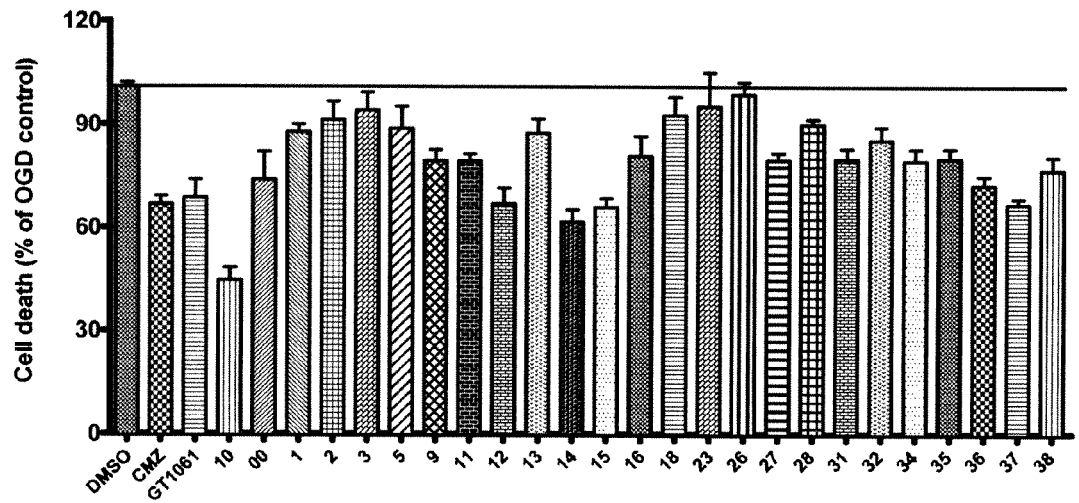
FIG. 1B contains a bar graphs of cell death (% of OGD control) for DMSO, CMZ, GT-1061, and compounds of structural formula (I)

In particular, FIG. 1 shows a comparison of neuroprotection by test compounds in primary rat neuronal cultures subjected to oxygen-glucose deprivation (OGD) and ischemia-reperfusion injury. Test compounds are compared to vehicle controls and the known neuroprotective agent CMZ. DMSO is dimethyl sulfoxide. Neuroprotection is represented by (i) a high cell viability relative to control as measured by the MIT assay and (ii) a low LDH activity as measured by assay of LDH. The abscissa in FIGS. 1A and 1B identify the compounds tested by GN number. The structures of AR-OH (also referred to as #00) and AR-N₃ (also referred to as #9 or GN-9)

are provided above. The structure of AR (also referred to as #10) and CMZ are as follows:

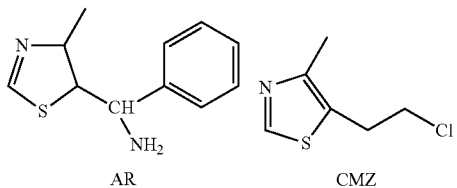

Primary cultures of cortical neurons were prepared as described (Madrigal et al., 2005). Briefly, brains were removed from embryonic day 16 Sprague Dawley rat embryos, cortices were dissected, and meninges were removed. Neurons were mechanically dissociated in Basal Medium Eagle 1× containing 33 mM glucose, 2 mM glutamine, 10% horse serum, and 10% FBS, then plated at $3 \times 10^5$ cells/cm$^2$ in poly-L-lysine-precoated plates. The medium was replaced 24 hours later with serum-free neuronbasal medium (NBM) supplemented with 0.5 mmol/L-glutamine and 2% complete B27 supplement. Four days later, 50% of the medium was replaced with fresh NBM. Neurons were used for OGD experiment after grown for 6-8 days in NBM.

Primary cortical cultured neurons were subjected to a transient OGD as described. On day 6-8 of culture, cultured neurons were placed in a humidified 37° C. incubator (95% $N_2$, 5% $CO_2$) and the culture medium were replaced with deoxygenated, glucose-free balanced salt solution, pH 7.4, containing the following (in mM): NaCl 116, CaCl$_2$ 1.8, MgSO$_4$ 0.8, KCl 5.4, NaH$_2$PO$_4$ 1, NaHCO$_3$ 14.7, HEPES 10. Following 2 hours of OGD incubation, OGD were ended by replacing OGD medium with drug conditioned fresh NBM (supplemented with 0.5 mmol/L-glutamine and B27 without antioxidants). Cultures were returned to the normoxic 37° C. incubator (5% $CO_2$) for 24 hours prior to evaluation of cell viability and neuronal death by MTT and LDH assay. The tested compounds (50 µM) were presented during 2-hour OGD and 24-hour reoxygenation.

FIG. 1A illustrates the evaluation of neuroprotection in primary neurons subject to transient OGD assayed by MTT. Primary cortical neurons were incubated with testing compounds (50 µM) in deoxygenated, glucose-free solution and placed in a humidified 37° C. incubator (95% $N_2$, 5% $CO_2$) for 2 hours, then conditioned neurobasal medium was given back to the cells. Cell viability was measured 24 hours after reperfusion by MTT assay. Cell viability percentage was calculated relative to 100% protection from CMZ against OGD-reperfusion injury. The data in FIG. 1A show mean and s.e.m., and are representative of at least 3 separate neuronal preparations. The dotted lines represent a neuroprotective zone equivalent to CMZ and compound neurotoxicity relative to the DMSO vehicle control.

FIG. 1B illustrates the evaluation of neuroprotection in primary rat neurons subject to transient OGD assayed by LDH. Primary cortical neurons were incubated with test compounds (50 µM) in deoxygenated, glucose-free solution and placed in a humified 37° C. incubator (95% $N_2$, 5% $CO_2$) for 2 h, followed by replacement with conditioned neurobasal medium under normoxic conditions. Cell viability was measured 24 hours after reperusion by MTT assay. Cell viability percentage was calculated relative to 100% cytoxicity from OGD-reperfusion in the presence of vehicle (DMSO). The data in FIG. 1B show mean and s.e.m., and are representative of at least three separate neuronal preparations. Components indicated as neurotoxic increased cell death relative to vehicle control in both assays.

Anti-Inflammatory Actions in Primary Rat Glial Cultures by Compounds of Structural Formula (I)

Attenuation of cytokine and inflammatory response by compounds of structural formula (I) were measured by induction of NOS reflected by inhibition of nitrite production in LPS/IFNγ treated primary rat glial cultures.

Primary mixed glia cultures were obtained as described previously (Vairano et al., 2002). Briefly, 1-2 day old Sprague Dawley rat pups were used to prepare primary mixed glial cultures. Cortices were dissected and meninges were removed. Tissues were cut into small pieces and transferred into PBS (without Ca$^{2+}$ and Mg$^{2+}$) containing 0.125% Trypsin and DNAse 35500 KU/ml, then incubated at 37° C. for 20 min. The cells were dissociated mechanically resuspended in DMEM (10% FBS), then grown in a T-75 flask. After 11-13 days in culture, the cells were replated at $2 \times 10^5$ cells/cm$^2$ in 96-well plates. Cells were used the next day.

Primary cultured cortical glia were incubated with LPS (1 mg/ml) in deoxygenated, glucose-free solution, pH 7.4, containing the following (in mM): NaCl 116, CaCl$_2$ 1.8, MgSO$_4$ 0.8, KCl 5.4, NaH$_2$PO$_4$ 1, NaHCO$_3$ 14.7, HEPES 10. The cells were placed in a humidified 37° C. incubator (95% $N_2$, 5% $CO_2$) for 2 hours, then conditioned DMEM media containing LPS or PBS were given back to the cells. The tested compounds (50 mM) or MAPK inhibitor (SB203580, 20 mM) were present during and after the OGD. The Griess assay for NO$_2^-$ production at 96 hours after OGD was used as measure of iNOS induction. Cell viability was measured later by MTT assay.

Compound GN-12, a 3-pyridyl substituted triazole pharmacore, manifested substantial neuroprotection and attenuation of inflammatory response in primary cultured rat cortical neuron and glial cells.

Figure 2A:
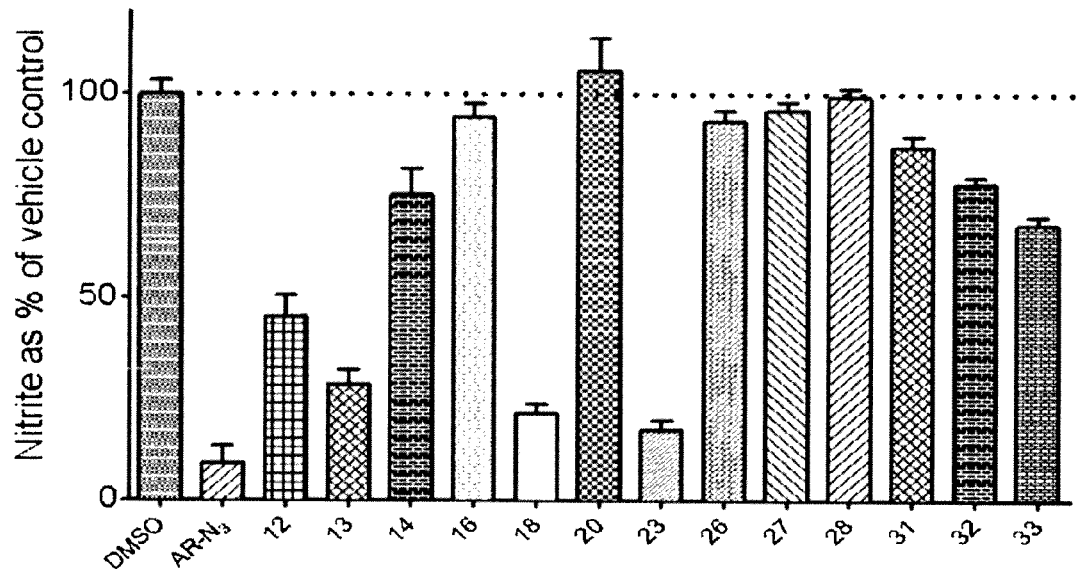
FIG. 2A contains bar graphs of nitrite (as % of vehicle control) for DMSO, AR-$N_3$, and compounds of structural formula (I)
Figure 2B:
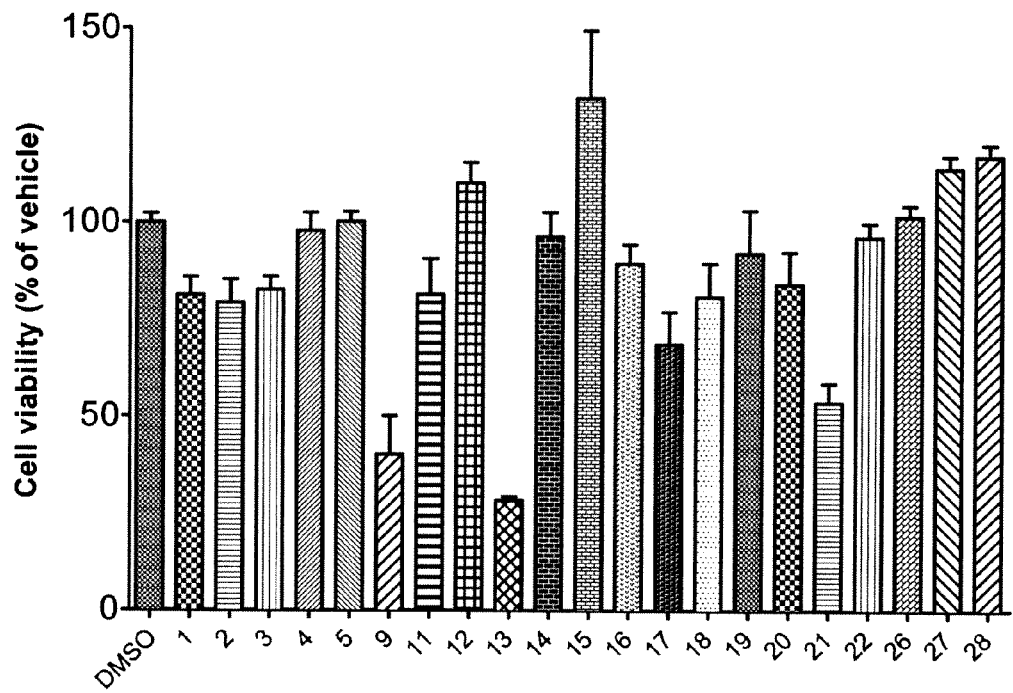
FIG. 2B contains bar graphs of cell viability (% of vehicle) for DMSO and compounds of structural formula (I)

FIGS. 2A and B illustrate primary rat glial cell cultures treated with LPS/IFG for 20 hours prior to measurement of nitrite in supernatant by Griess assay. FIG. 2 is a comparison of test compounds in primary rat glial cultures subjected to treatment with lipopolysaccharide (LPS) from *E. coli* and ODG to elicit production of cytokines and other pro-inflammatory mediators including inducible nitric oxide synthase. Test compounds were compared to vehicle controls and CMZ, a known inflammatory cytokine attenuating agent. Attenuation of inflammatory response was measured by nitrite production from NOS induced by the combination of LPS/OGD. A lower value corresponds to attenuation of cytokine production. The numbers on the abscissus of FIGS. 2A and 2B are GN numbers of the present compounds.

FIGS. 3A and 3B illustrate neuroprotection in response to amyloid neurotoxicity afforded by compounds of structural formula (I). FIGS. 3A and 3B show neuroprotection in primary neurons treated with Aβ$_{42}$. In particular, primary cortical cultures at 10-11 DIV were preincubated with 100 µM of picrotoxin for one hour, then perfused with test compounds at 50 µM. Soluble oligomers of human Aβ$_{1-42}$ then were added at a physiologically relevant concentration of 250 nM. Cultures then were incubated for 5 days, after which time MTT and LDH assays were performed. Results were normalized to untreated DMSO and treated DMSO and statistical analysis was performed with ANOVA, with post-hoc Dunnet's MCT comparing to untreated DMSO, *=p<0.5, ***=p<0.001. Picrotoxin acts as a noncompetitive antagonist for the GABA$_A$ receptor chloride channels. It is therefore a channel blocker rather than a receptor antagonist. FIG. 3 shows that the GABA antagonist picrotoxin blocks the neuroprotective actions of the test compounds.

In another test, compound GN-12 of structural formula (I) was shown to reverse a cognition deficit in scopolamine treated mice assayed by STPA. The scopolamine treatment results in mice having an attenuated cognitive function. STPA (step through passive avoidance task) is widely used to test long-term memory. The STPA apparatus consists of a two-compartment acrylic box with an illuminated side (15×12×12 cm) connected to a dark side (15×12×12 cm) by a vertical door. The dark side is equipped with an electric grid floor. During the habituation, animals were habituated to the normal behavior of rapidly translocating to the dark from the light side, where they were initially placed. Habituation trials are continued until latency of entering the dark side for each animal is less than 30 seconds. Animals that cannot pass this screening phase are excluded from the study. During the training, animals were trained by receiving an aversive electrical shock (0.5 mA, 2 sec), triggered by entry to the dark compartment, until the latency of entering the dark side reach 300 seconds. At 24 and 72 hours post-training, the animals again are individually placed in the light compartment and the latency to enter the dark compartment, without shock stimulus, is recorded. Statistical analysis of the latency data was performed with one-way ANOVA followed by Bonferroni multiple comparison test. For STPA tests using naïve animals, each animal was administered two ip injections. Amnesic agent (e.g., scopolamine 1 mg/kg, MK-801 0.07 mg/kg or diazepam 0.5 mg/kg) or vehicle was administered 30 minutes prior training to induce amnesia, and testing drug was given at 20 minutes prior training start., i.e. (Vehicle+Vehicle; Scopolamine+Vehicle; or Scopolamine+drug). For APP/PS1 animals, each animal only received one i.p. injection of testing drug at 20 min prior training. Test compounds are compared to vehicle controls. An enhanced latency time represents higher cognitive function and increased memory consolidation and retrieval.

Another test demonstrated the ability of compounds of structural formula (I) to restore normal LTP in hippocampal brain slices from amyloid transgenic mice. Animals were killed by cervical dislocation followed by decapitation. Hippocampi were quickly removed and sectioned into 400 μm slices. Hippocampal LTP were recorded as previously described (Vitolo et al., 2002). Briefly, hippocampal slices were transferred to a recording chamber where they were maintained at 29° C. and perfused continuously with artificial cerebrospinal fluid (aCSF) pre-bubbled with 95% $O_2$ and 5% $CO_2$. The aCSF contains (in M) following: 124.0 NaCl, 4.4 KCl, 1.0 $Na_2HPO_4$, 25.0 $NaHCO_3$, 2.0 $CaCl_2$, 2.0 $MgSO_4$, 10.0 glucose. After about one hour of recovering, the stimulating and the recording electrodes were both placed in CA1 stratum radiatum and CA1 field-excitatory-post-synaptic potential (fEPSP) were recorded. For LTP experiments, a 15 minute baseline was recorded every minute at an intensity that evokes a response about 35% of the maximum evoked response. LTP was induced using θ-burst stimulation (4 pulses at 100 Hz, with the bursts repeated at 5 Hz and each tetanus including 3 ten-burst trains separated by 15 seconds). In a set of experiments, LTP was induced with 1 or 2 ten-burst trains to assess the effect of drug on LTP induced with a different strength of the tetanus. Responses were recorded for 2 hours after tetanization and measured as fEPSP slope expressed as percentage of baseline. Hippocampal slices were perfused with testing compounds (100 μM) for 5 minutes before inducing LTP. The results were expressed as mean±Standard Error Mean (SEM).

A compound of structural formula (I) therefore is useful in a method of treating neurological conditions and/or preventing an undesirable mental condition (e.g., memory loss) comprising administering a therapeutically effective amount of a compound of structural formula (I) to an individual in need thereof. In one embodiment, the compound of structural formula (I) provides neuroprotection. In another embodiment, the compound of structural formula (I) provides cognition enhancement.

The above tests show that compounds of structural formula (I) have a high efficacy in effecting neuroprotection in vivo in models of transient global and focal cerebral ischemia when administered after the ischemic insult. The compounds of structural formula (I) can be used in the treatment of diseases and conditions including but not limited to stroke, Parkinson's disease, Alzheimer's disease, Huntington's disease, multiple sclerosis, amylotrophic lateral sclerosis, AIDS-induced dementia, epilepsy, alcoholism, alcohol withdrawal, drug-induced seizures, viral/bacterial/fever-induced seizures, trauma to the head, hypoglycemia, hypoxia, myocardial infarction, cerebral vascular occlusion, cerebral vascular hemorrhage, hemorrhage, vascular dementia, environmental excitotoxins of plant, animal, or marine origin, neurodegenerative disorders and dementia, including diseases of aging resulting in dementia, neuroinflammation, or neuronal, and synaptic dysfunction; and neurological disorders characterized by imbalanced excitatory stimuli, such as anxiety, epilepsy, and insomnia.

Neuroprotection and/or cognition enhancement by administration of a compound of structural formula (I) can be affected, for example, by modulating an interaction a glutamate or non-glutamate neuroreceptor or attenuating cytokine induced damage. The attenuation of cytokine concentration by a compound of structural formula (I) can also be useful for preventing or mitigating tissue and/or cellular damage.

Accordingly, in certain aspects and embodiments of the invention, compounds of structural formula (I) have an ability to inhibit production of pro-inflammatory cytokines.

Overproduction of pro-inflammatory cytokines is associated with a wide range of diseases and conditions, such as, for example, aging, septic shock, ischemia, overexpression of cytokines, ulcers, inflammatory bowel disease (e.g., gastritis, ulcerative colitis or Crohn's disease), diabetes, arthritis (e.g., rheumatoid arthritis), asthma, cirrhosis, allograft rejection (e.g., transplant rejection), encephalomyelitis, meningitis, pancreatitis, peritonitis, vasculitis, lymphocytic choriomeningitis, glomerulonephritis, ophthalmologic diseases (e.g., uveitis, glaucoma, blepharitis, chalazion, allergic eye disease, corneal ulcer, keratitis, cataract, retinal disorders, age-related macular degeneration, optic neuritis, and the like), ileitis, inflammation induced by overproduction of inflammatory cytokines (e.g., liver inflammation, renal inflammation, airway inflammation, and the like), hemorrhagic shock, anaphylactic shock, burn, infection leading to the overproduction of inflammatory cytokines (including bacterial (e.g., *E. coli* infection), viral (e.g., HIV), fungal (e.g., Candidiosis and histoplasmosis) and parasitic (e.g., Leishmaniasis and Schistosomiasis) infections), hemodialysis, chronic fatigue syndrome, stroke, cancers (e.g., breast, melanoma, carcinoma, and the like), cardiovascular diseases associated with overproduction of inflammatory cytokines (e.g., heart disease, cardiopulmonary bypass, ischemic/reperfusion injury, and the like), ischemic/reperfusion associated with overproduction of inflammatory cytokines, toxic shock syndrome, adult respiratory distress syndrome, cachexia, myocarditis, autoimmune disorders, eczema, psoriasis, heart failure, dermatitis, urticaria, cerebral ischemia, systemic lupus erythematosis, AIDS, neurodegenerative disorders (e.g., chronic neurodegenerative disease), chronic pain, priapism, cystic fibrosis, schizophrenia, depression, premenstrual syndrome, anxiety, addiction, migraine, gastrointestinal motility disorders, obesity, hyperphagia, solid tumors (e.g., neuroblastoma), malaria, hematologic cancers, myelofibrosis, lung injury, graft-versus-host disease, head injury, CNS trauma, hepatitis, renal failure, liver disease (e.g., chronic hepatitis C), drug-induced lung injury (e.g., paraquat), transplant rejection and preservation, fertility enhancement, bacterial translocation, circulatory shock, traumatic shock, and vascular aneurysm (e.g., aortic aneurysm), ileus, and myocardial infarction.

In addition, the compounds of structural formula (I) can be used in cytokine therapy (with consequent induction of cytokine overproduction) which, for example, is commonly used in the treatment of cancer, autoimmune disease, and in AIDS patients. Systemic hypotension due to the induction of cytokine overproduction is a dose-limiting side effect of cytokine therapy. Thus, a large patient population exists which benefit from the present invention.

Compounds of Structural Formula (II)

The compounds of structural formula (I) exhibit excellent neuroprotective properties. These properties are enhanced by introducing aliphatic nitro groups into the molecule. The nitrated compounds of structural formula (II), like the compounds of structural formula (I), therefore mitigate cellular damage, protect brain tissue from injury, and provide amelioration of symptoms and pathology associated with brain injury. The compounds of structural formula (II) provide both neuroprotection and neurorestoration utilizing the activity of the MZ pharmacophore and the NO mimetic nitrate. The compounds of structural formula (II) provide both neuroprotection and neurorestoration utilizing the activity of the MZ pharmacophore and the NO mimetic nitrate. The compounds of structural formula (II) also enhance NO/cGMP signaling.

The compounds of structural formula (II) are chimeric nitrate esters, i.e., organic nitrates that contain a 4-methylthiazole (MT) pharmacophore and an NO mimetic. A present chimeric nitrate ester incorporating an MT pharmacore represents a novel therapy for the treatment of brain injuries and neurodegenerative diseases and conditions.

The present invention therefore is directed to methods and compounds useful for treating neurodegeneration, or preventing or mitigating tissue and/or cellular damage, by administering to an individual in need thereof a nitrate ester of structural formula (II). Neuroprotection and/or cognition enhancement can be affected, for example, by modulating an interaction with soluble guanylyl cyclase (sGC, the enzyme responsible for cGMP production in various areas of the brain), a glutamate or non-glutamate neuroreceptor or attenuating cytokine induced damage. The attenuation of cytokine concentration by a nitrate ester of structural formula (II) also can be useful for preventing or mitigating tissue and/or cellular damage.

According to certain aspects of the invention, neurodegeneration is mitigated by stimulating cerebral sGC. One of the major targets for organic nitrates is sGC activation, resulting in the production of cGMP. Experimental evidence obtained in a number of in vitro model systems supports the notion that elevated levels of cGMP help to prevent apoptotic (programmed) cell death. Thus, a cGMP-dependent mechanism significantly increases the survival of trophic factor-deprived PC12 cells and rat sympathetic neurons (Farinelli et al., 1996), and of primary cultures of rat embryonic motor neurons (Estevez et al., 1998). The mechanism of action for organic nitrates in preventing apoptotic cell death may be inhibition of caspase-3 activation indirectly through elevations in cGMP levels or directly via protein S-nitrosylation of the enzyme by an NO-intermediate (Kim et al., 1997). Caspase-3 is a member of the cysteine protease family of enzymes that are essential for the execution step in apoptosis (Cohen, 1997; Nicholson and Thornberry, 1997). Activation of caspase-3 is required for apoptotic cell death in trophic factor-deprived PC12 cells (Haviv et al., 1997) and in glutamate-mediated apoptotic cell death of cultured cerebellar granule neurons (Du et al., 1997). In animal models of cerebral ischemia, caspase-3 activity is induced and may be responsible for the apoptotic component of delayed neuronal cell death (Chen et al., 1998; Namura et al., 1998; Ni et al., 1998). Inhibitors of caspase-3 significantly decrease the apoptotic component of delayed neuronal cell death in response to ischemic injury both in vitro (Gottron et al., 1997) and in vivo (Endres et al., 1998). A secreted region of the Alzheimer's disease β-amyloid precursor protein lowers intracellular calcium levels and provides neuroprotective effects on target cells through increases in cGMP levels and activation of protein kinase G (Barger et al., 1995; Furukawa et al., 1996). In accordance with the present invention, nitrated compounds of structural formula (II) have the capacity to activate sGC directly, or via release of an NO-containing intermediate, to modulate sGC activity.

In one aspect of the invention, cognition enhancement (e.g., improved memory performance) is achieved by stimulating cerebral sGC. Several lines of experimental evidence support the notion that sGC and cGMP are involved in the formation and retention of new information. cGMP has been directly implicated in both long-term potentiation (LTP) and long-term depression (LTD), which are proposed cellular models for learning and memory (Arancio et al., 1995; Wu et al., 1998). In animal models, elevation of hippocampal cGMP levels leading to increased protein kinase G activity has been shown to be important for retention and consolidation of new learning (Bernabeu et al., 1996, 1997). Thus, stimulation of cerebral sGC activity is expected to improve learning and memory performance in individuals in whom cognitive abilities are impaired by injury, disease, or aging.

Compounds of structural formula (II) activate soluble sGC and cause cGMP accumulation in vascular and brain tissue. Activation of sGC and accumulation of cGMP have been shown to be important in the neuroprotection of hippocampal brain slices subjected to a period of in vitro ischemia.

The potent, peripheral hypotension effects of organic nitrates may have deleterious effects. These deleterious effects are overcome by the present organic nitrates of structural formula (II) that incorporate sulfur-containing functionalities, which themselves deliver protective effects to cells. The compounds of structural formula (II) therefore protect against, and provide behavioral relief of symptoms of diseases and conditions including cognition deficits resulting from brain insults (including amyloid neurotoxicity and synaptic dysfunction), and neurodegenerative disorders and dementia, including stroke, vascular dementia, Alzheimer's disease, Parkinson's disease, and other diseases of aging resulting in dementia, neuroinflammation, or neuronal and synaptic dysfunction. In particular, the compounds of structural formula (II) are useful in the same methods as the compounds of structural formula (I).

The compounds of structural formula (II) are "aliphatic nitrates", in which a nitrate group is bonded to a non-aromatic carbon atom. By incorporating one or more nitrate group into the compound, an aliphatic nitrate acts as a nitric oxide (NO) mimetic. In some preferred embodiments, a compound of structural formula (II) contains at least two nitrate groups, and in other embodiments, a nitrate group is beta, gamma, or delta to a sulfur atom. In other preferred embodiments, a compound of structural formula (II) contains at least one aliphatic nitrate group and at least one heterocyclic sulfur atom in a thiazole ring. A compound of structural formula (II) can contain 1, 2, 3, 4, 5, 6, 7, 8, 9, or 10 nitro groups. In another embodiment, a compound of structural formula (II) is used in methods of preventing or mitigating tissue and/or cellular damage in the brain of a subject by administering a therapeutically effective amount of a compound of structural formula (II) to the subject.

The compounds of structural formula (II) are used in methods of affecting neuroprotection, mitigating neurodegeneration, affecting cognition enhancement, and/or protecting tissues from oxidative injury. The compounds of structural formula (II) also are neuroprotective agents and are used to protect tissues from oxidative injury.

Compounds of structural formula (II) often position a sulfur atom with respect to a nitrate functional group such that a linker, like a carbonyl group, intervenes to form a linkage that can be bioactivated by cleavage. Such compounds form part of the invention if cleavage at the bond produces two entirely separate molecules, i.e., one containing the nitrate functionality and another the S-functionality. It is understood by one skilled in the art that facile cleavage of a carbonyl linkage in an aqueous biological milieu will render an aliphatic nitrate that may not contain a sulfur atom, and such a compound comprises part of the present invention when the sulfur atom is present in a heterocyclic ring.

Specific compounds of structural formula (II) include the following:

GN-29
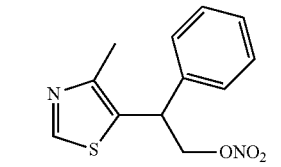

GN-207
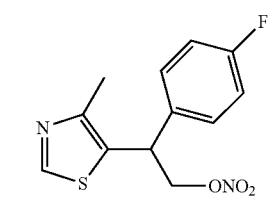

GN-206
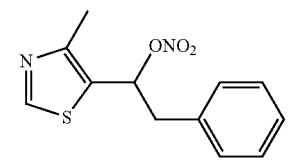

GN-30
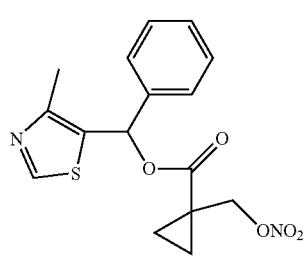

-continued

GM-30
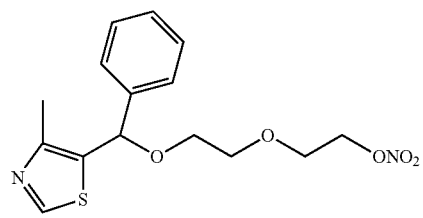

GN-44
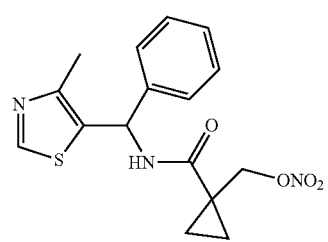

GN-202
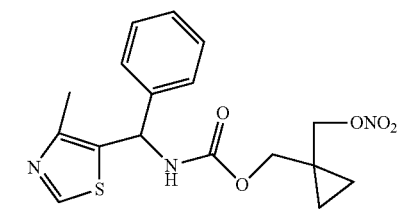

GN-203
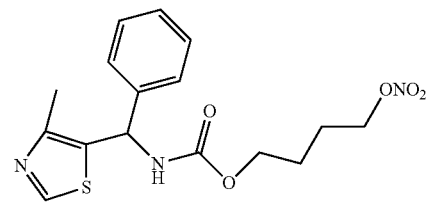

GN-204
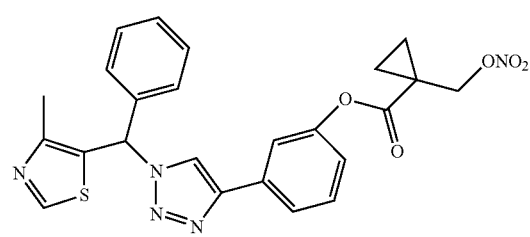

GM-204

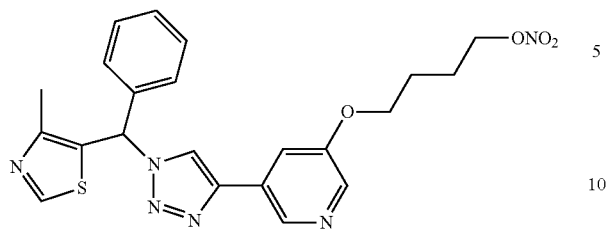

GN-42

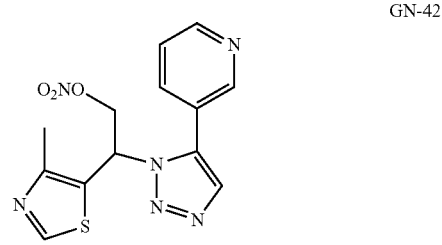

GM-45

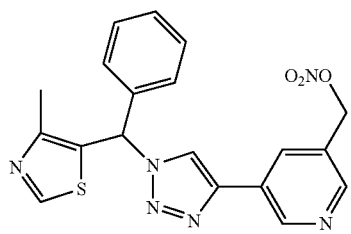

GN-41

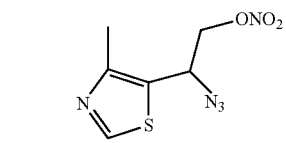

GN-205

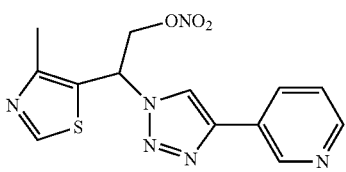

Compounds of structural formula (II) can be synthesized by methods set forth herein and in U.S. Pat. Nos. 5,807,847; 5,883,122; 6,310,052; and 6,365,579, each incorporated herein by reference. Various compounds used in the synthetic methods are commercially available and/or can be synthesized by standard techniques in the art. In general, nitrate esters can be prepared from a corresponding alcohol, oxirane, or alkene by standard methods in the art, that include, for example, nitration of alcohols and oxiranes, mixed aqueous/organic solvents using mixtures of nitric and sulfuric acid and/or their salts with temperature control (see Yang et al., 1996); nitration of alcohols and oxiranes in acetic anhydride using nitric acid or its salts with or without added acid catalyst with temperature control (see, e.g., Louw et al., 1976); nitration of an alcohol with a nitronium salt, e.g. a tetrafluoroborate; and nitration of an alkene with thallium nitrate in an appropriate solvent (see Ouellette et al., 1976).

le;3qThe following synthetic scheme demonstrates the use of a Bunte salt in the preparation of compounds of a structural formula (II).

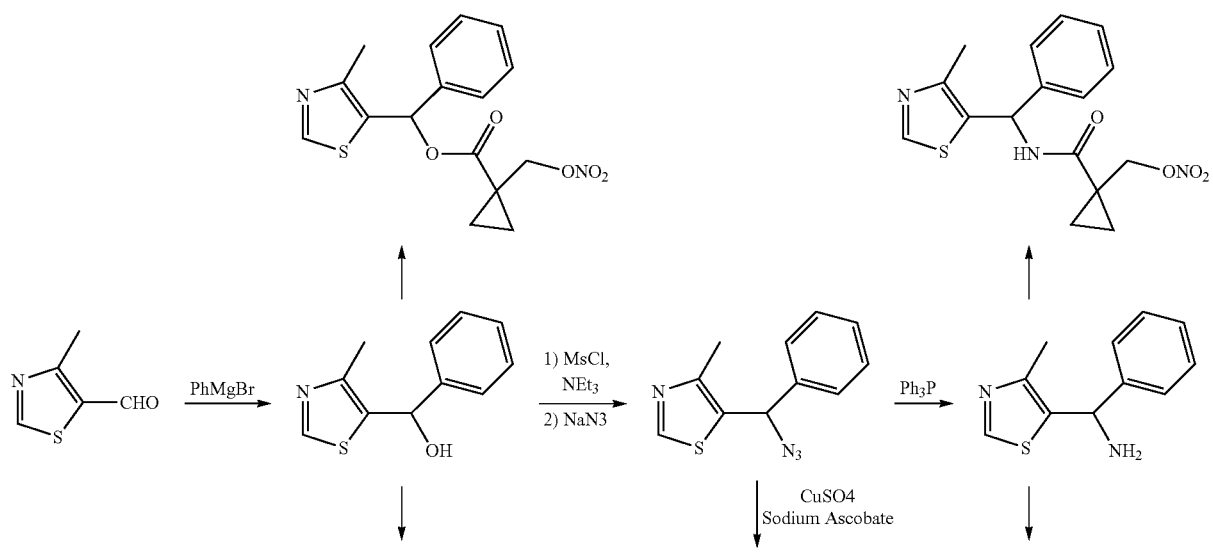

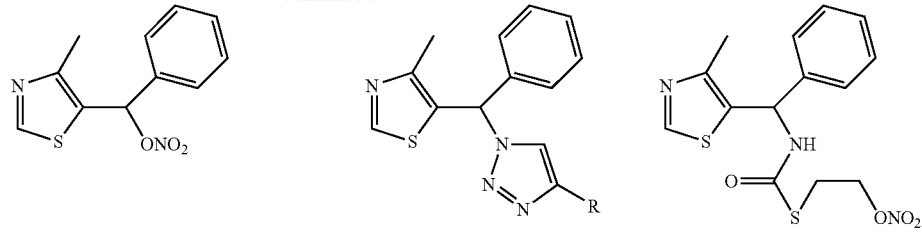

The following synthetic scheme illustrates the preparation of additional compounds of structural formula (II). Esters of cyclopropane carboxylic acid manifest substantial increase in stability under both acid- and base-catalyzed hydrolytic conditions (D. M. Bender et al., *Organic Letters*, 10(3), 2008, 509-511). 1-Nitrooxymethylcyclopropanecarboxylic acid (compound 2) therefore was utilized to prepare the stabilized AR-OH compound GN-30. Carbamate prodrugs GN-202 and GN-203 were obtained by converting AR-A008055 to an isocyanate, then reacting with compound 1 or 4-nitrooxy-butan-1-ol, respectively. GN-39 was a byproduct of the reaction. GM-30 is an AR-OH based prodrug with an ether linkage, using the ethylene glycol linker unit to improve water solubility.

Reaction conditions: a) fuming $HNO_3$, $Ac_2O$, $CH_2Cl_2$, 0° C., 45%; b) TEMPO, $PhI(OAc)_2$, DCM, 70%; c) $NaClO_2$, $NaH_2PO_4$, 2-methyl-2-butene, tBuOH, 90%; d) 2, EDCI, DIPEA, HOBT, DMF, 40%; e) MsCl, $NEt_3$ then $NaN_3$, $CH_3CN$, 80%; f) $LiAlH_4$, THF, 85%; g) triphodgene, AcOEt, reflux; h) 1, $NEt_3$, THF, 51%; i) 4-nitrooxy-butan-1-ol, $NEt_3$, THF, 65%, GN-39 7%; j) bis(2-bromomethyl)ether, NaH, DMF, 86%; k) $AgNO_3$, $CH_3CN$, reflux; l) compound 2, EDCI, DIPEA, HOBT, DMF, 70%.

The stability of compounds of structural formula (II) in phosphate buffer (pH 7.4) was monitored using HPLC. For example, GM-30, GN-44, and GN-203 demonstrated excellent stability.

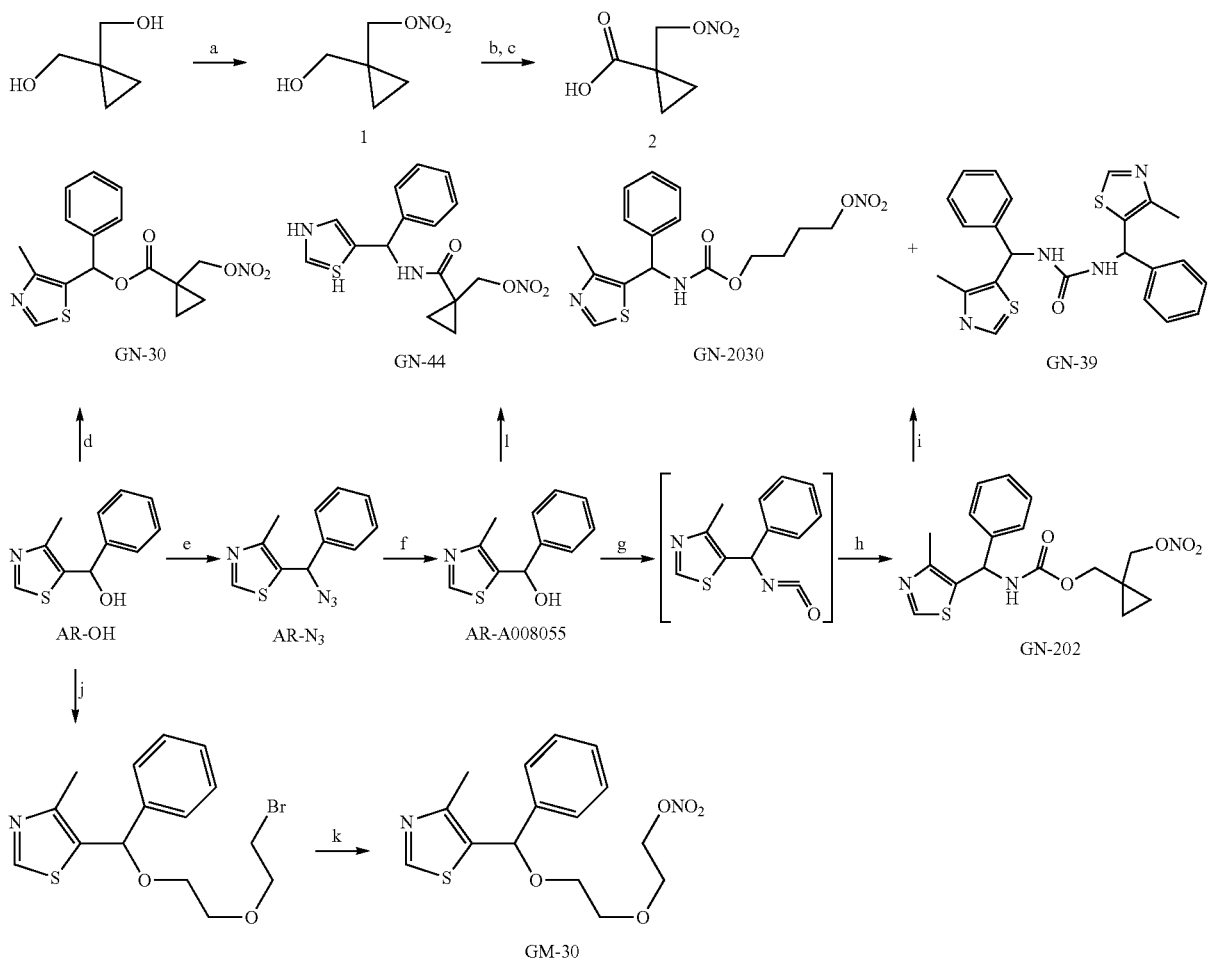

Compound GN-12 of structural formula (II), having a 3-pyridyl group attached at the 4-position of the triazole ring, showed superior neuroprotective and anti-neuroinflammatory activities. Compound GN-12 therefore was selected as a scaffold to synthesize additional compounds of structural formula (II) that could provide even further beneficial effects. As shown below, compound GN-204 has a cyclopropane linker and was synthesized from compound GN-37 under Mitsunobu conditions with a ether linkage.

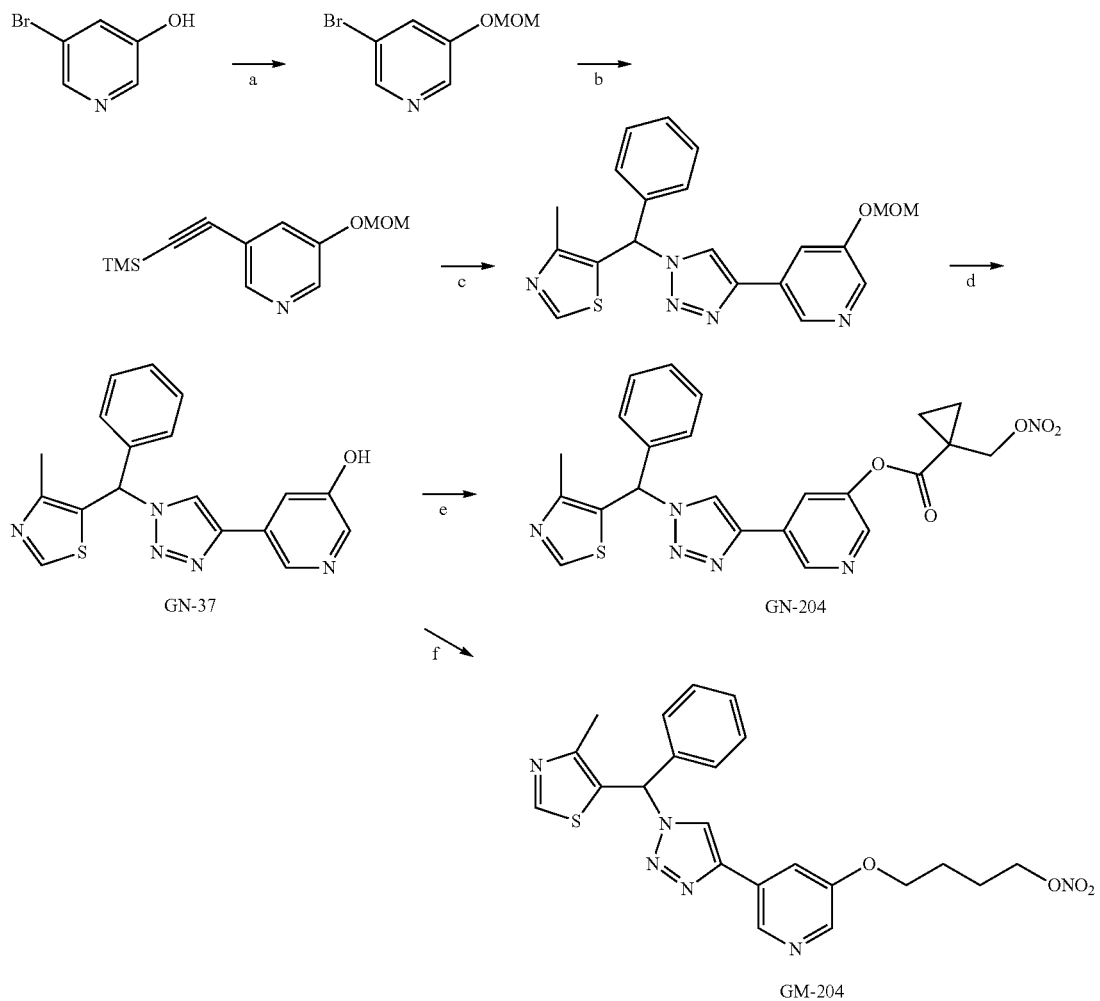

Reaction conditions: a) MOM-Br, $K_2CO_3$, THF, 88%; b) ethynyltrimethylsilane, CuI, $Pd(Ph_3P)_2Cl_2$, $NEt_3$, THF, 81%; c) AR-$N_3$, $K_2CO_3$, $CuSO_4$, NaAsc, MeOH—$H_2O$ (2:1), 86%; d) HCl/i-PrOH(1.5 M), 70° C., 83%; e) compound 2, HBTU, DIPEA, THF, 77%; f) 4-nitrooxy-butan-1-ol, $Ph_3P$, DIAD, 67%.

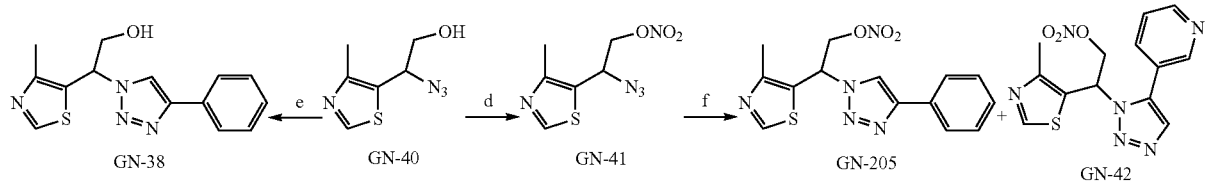

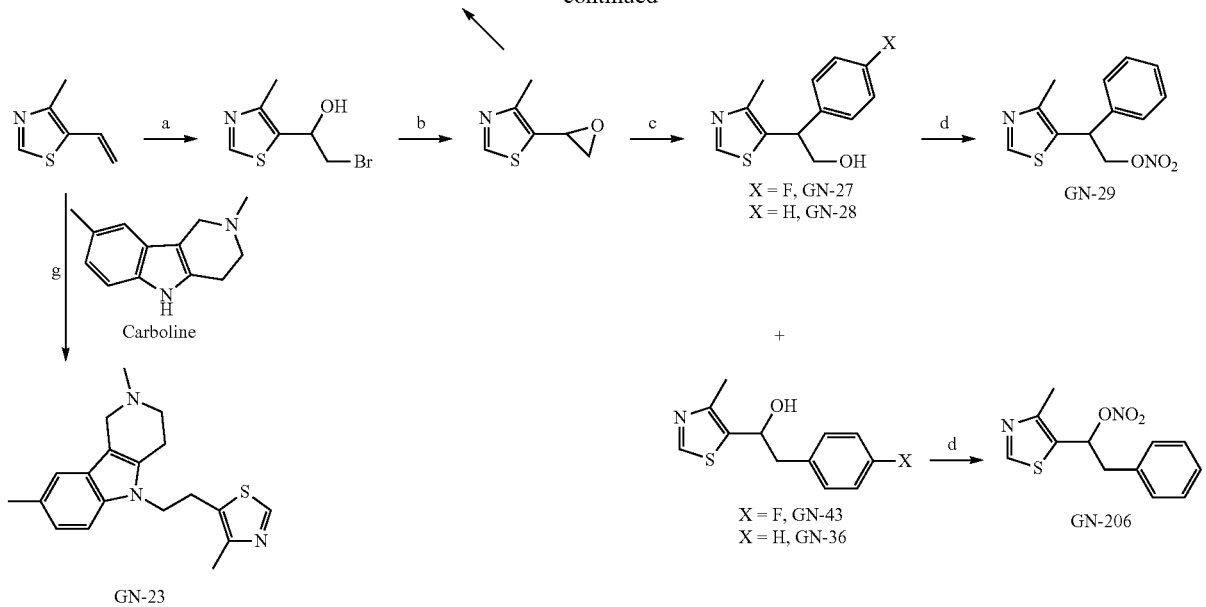

Reaction conditions: a) NBS, dioxane-$H_2O$, 88%; b) $K_2CO_3$, MeOH; c) PhMgBr, THF; d) fuming $HNO_3$, $Ac_2O$, $CH_2Cl_2$, 0° C.; e) 3-ethynyl pyridine, $CuSO_4$, NaAsc, tBuOH—$H_2O$(2:1), 80%; f) 3-ethynyl pyridine, toluene, reflux, 48 h, GN-205 44%, GN-42 33%; g) carboline, NaH, DMSO, 90° C., 5 h, 36%.

Figure 4:
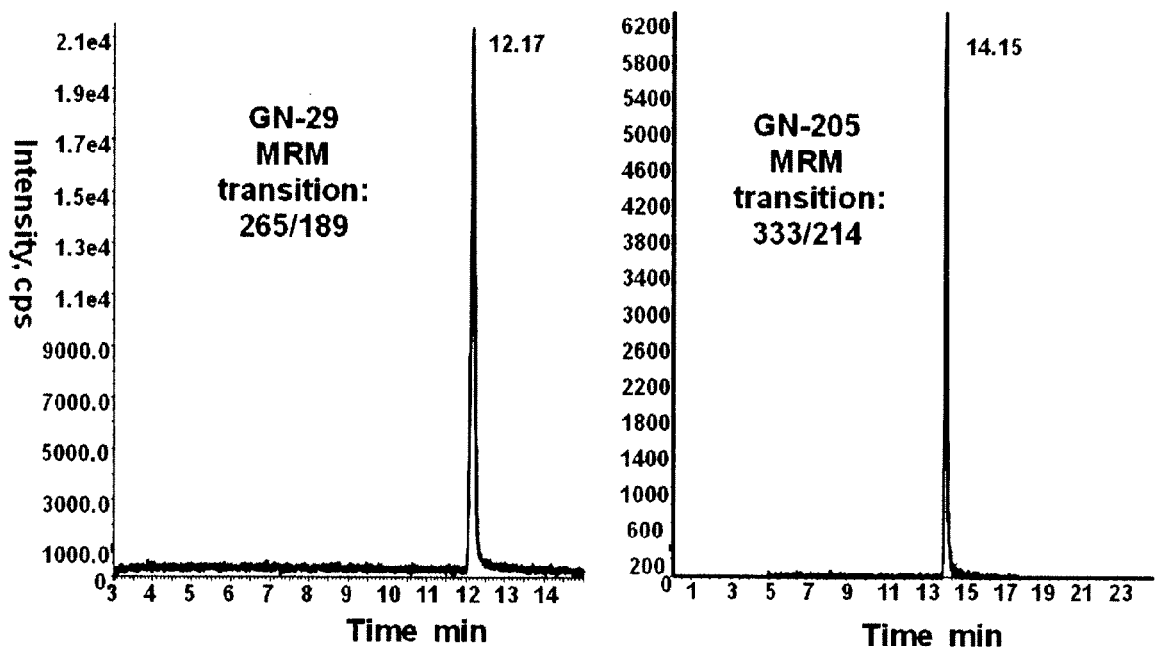
FIG. 4 contains graphs of intensity (cps) vs. time min) showing the ability of two compounds of structural formula (II) to penetrate the brain.

Compounds of structural formula (II), i.e., GN-29 and GN-205, were tested for an ability to penetrate the brain. WT mice were given an i.p. injection at a dose of 1 mg/kg, which is equivalent to transgenic mice studies. The presence of drugs in brain tissue was measured by LC-MS using MRM methods. As exemplified by high S/N (signal/noise) ratio of GN-29 and GN-205 in FIG. 4, the compounds are highly bioavailable in the brain after systemic delivery.

A compound of structural formula (II), i.e., GN-29, also was tested for procognitive and anti-inflammatory actions. Compound GT-1061 was used as a control and has a structure:

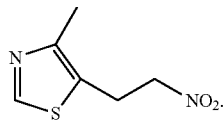

Figure 5:
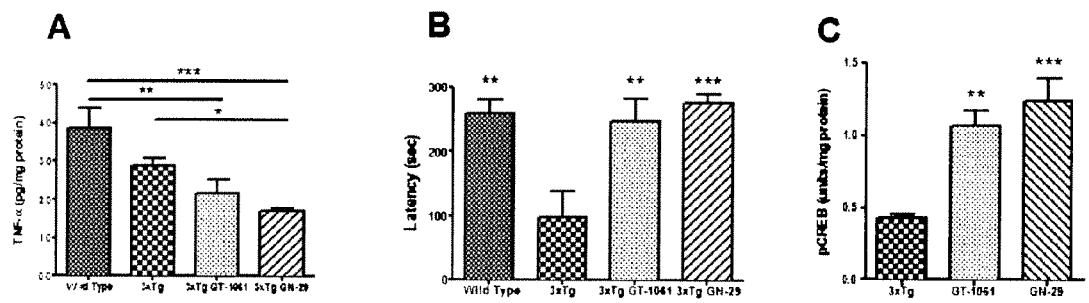
FIG. 5 contains graphs showing the procognitive and anti-inflammatory action of a compound of structural formula (II).

FIG. 5 shows the procognitive and anti-inflammatory actions of a compound of structural formula (II) after an 11 week treatment of LaFerla 3×Tg AD Mice. FIG. 5A shows ELISA performed on cortical/hippocampal protein homogenates showing a reduction in levels of TNF-α compared to WT (3.86±0.53 µg/mg protein) in animals treated with GT-1061 (2.18±0.34 µg/mg protein, p<0.01) or GN-29 (1.70±0.09 µg/mg protein, p<0.001), and a decrease in GN-29 treated animals relative to 3×Tg control (2.9±0.2 µg/mg protein, p<0.05). FIG. 5B shows a reversal of cognitive deficit as demonstrated by an increased latency after 24 h in STPA to WT levels (260±23 s) compared to 3×Tg control (97±41 s, p<0.01) in mice treated with GT-1061 (248±35 s, p<0.01) or GN-29 (277±14 s, p<0.001). Amyloid load also was reduced by drug treatment (data not shown). FIG. 5C shows an increase in levels of CREB phosphorylated at serine 133 compared to 3×Tg control (0.42±0.03 units/mg protein) in groups treated with GT-1061 (1.07±0.11 units/mg protein, p<0.01) or GN-29 (1.2±0.16, p<0.001). The tests show that GN-29 reverses a cognitive deficit in the transgenic mouse model.

The compounds of structural formula (II) therefore are useful in the treating the same diseases and conditions treatable by a compound of structural formula (I), as listed above.

In particular it is appreciated by persons skilled in the art that an organic nitrate compound in which vasodilatory potency is reduced and neuroprotective potency increased represents a new and useful therapeutic agent for use in neuroprotection, particularly in treatment of conditions including but not limited to: stroke; Parkinson's disease; Alzheimer's disease; Huntington's disease; multiple sclerosis; amylotrophic lateral sclerosis; AIDS-induced dementia; epilepsy; alcoholism; alcohol withdrawal; drug-induced seizures; viral/bacterial/fever-induced seizures; trauma to the head; hypoglycemia; hypoxia; myocardial infarction; cerebral vascular occlusion; cerebral vascular hemorrhage; hemorrhage; environmental excitotoxins of plant, animal, or marine origin. GTN itself, proposed as a neuroprotective agent, has no clinical utility as a neuroprotective agent in therapy owing to its extraordinarily high vasodilatory potency. Similarly, by extrapolation, 1,2,3-trinitratopropane (GTN) derivatives are not expected to have clinical utility as neuroprotective agents in therapy owing to their especially high vasodilatory potency.

It will additionally be appreciated by those skilled in the art that the use of an organic nitrate of structural formula (II) in cognition enhancement therapy represents a new and useful treatment for cognition enhancement, particularly in treatment of diseases and conditions including, but not limited to, stroke; dementias of all type, trauma, drug-induced brain damage, and aging.

In particular, the compounds of structural formula (II) comprise at least one nitrate group. The nitrate groups(s) optionally can be covalently bound to a carrier moiety or molecule (e.g., an aromatic group, an aliphatic group, peptide, steroid, nucleoside, peptidomimetic, steroidomimetic, or nucleoside analogue, or the like). In addition to functioning as a carrier for the nitrate functionality, the carrier moiety or molecule can enable the compound to traverse biological membranes and to be biodistributed preferentially, without excessive or premature metabolism. Further, in addition to functioning as a carrier for the nitrate functionality, the carrier moiety or molecule can enable the compound to exert amplified neuroprotective effects and/or cognition enhancement through synergism with the nitrate functionality.

Carrier moieties useful in the present invention also include moieties that allow a present compound to be selectively delivered to a target organ. For example, delivery of a present compound to the brain may be enhanced by a carrier moiety using either active or passive transport (a "targeting moiety"). For example, the carrier molecule can be a redox moiety, as described in, for example, U.S. Pat. Nos. 4,540,654 and 5,389,623, each incorporated herein by reference. These patents disclose drugs linked to dihydropyridine moieties that can enter the brain, where they are oxidized to a charged pyridinium species which is trapped in the brain. The drugs therefore accumulate in the brain. Other carrier moieties include compounds, such as amino acids or thyroxine, that can be passively or actively transported in vivo. Such a carrier moiety can be metabolically removed in vivo, or can remain intact as part of an active compound. Structural mimics of amino acids (and other actively transported moieties) including peptidomimetics, are also useful in the invention. As used herein, the term "peptidomimetic" includes peptide analogues that serve as appropriate substitutes for peptides in interactions with, for example, receptors and enzymes. The peptodomimetic must possess not only affinity, but also efficacy and substrate function. A peptidomimetic therefore exhibits functions of a peptide, without restriction of structure to amino acid constituents. Peptidomimetics and methods for their preparation and use are described in Morgan et al. (1989). Many targeting moieties are known, and include, for example, asialoglycoproteins (see e.g., Wu, U.S. Pat. No. 5,166,320, incorporated herein by reference) and other ligands which are transported into cells via receptor-mediated endocytosis.

The compounds of structural formula (I) and (II) can be formulated to ensure proper distribution in vivo. For example, the blood-brain barrier (BBB) excludes many highly hydrophilic compounds. To ensure that the compounds of structural formula (I) and (II) cross the BBB, they can be formulated, for example, in liposomes. For methods of manufacturing liposomes, see, e.g., U.S. Pat. Nos. 4,522,811; 5,374,548; and 5,399,331, each incorporated herein by reference. The liposomes may comprise one or more moieties which are selectively transported into specific cells or organs ("targeting moieties"), thus providing targeted drug delivery (see, e.g., Ranade et al., 1989). Exemplary targeting moieties include folate and biotin (see, e.g., U.S. Pat. No. 5,416,016, incorporated herein by reference); mannosides (Umezawa et al., 1988), antibodies (Bloeman et al., 1995; Owais et al., 1995), and surfactant protein A receptor (Briscoe et al., 1995). In one preferred embodiment, the compounds of structural formula (I) and (II) are formulated in liposomes. In more preferred embodiments, the liposomes include a targeting moiety.

In one embodiment, the present invention provides a method of treating an above disclosed disease or condition by administering a therapeutically effective amount of a compound of structural formula (I) or (II) to an individual in need thereof. A method of the present invention can be accomplished by administering a compound of structural formula (I) or (II) as the neat compound or as a pharmaceutical composition. Administration of a pharmaceutical composition, or neat compound, can be performed during or after the onset of the disease or condition. Typically, the pharmaceutical compositions are sterile, and contain no toxic, carcinogenic, or mutagenic compounds that would cause an adverse reaction when administered.

The present invention also is directed to pharmaceutical compositions comprising a compound of structural formula (I) or (II). Further provided are kits comprising a compound of structural formula (I) or (II), and an insert having instructions for using the compound.

In the present method, a therapeutically effective amount of one or more compound of structural formula (I) or (II), typically formulated in accordance with pharmaceutical practice, is administered to a mammal in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors. Typically, the mammal is a human being.

A compound of the invention can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a present compound of the invention is administered in an effective amount to achieve its intended purpose. The exact formulation, route of administration, and dosage is determined by an individual physician in view of the diagnosed disease or condition. Dosage amount and interval can be adjusted individually to provide levels of a compound of the invention that is sufficient to maintain therapeutic effects.

Compounds of structural formula (I) and (II) are administered at a therapeutically effective amount sufficient to mitigate neurodegeneration, to effect neuroprotection, to effect cognition enhancement, and/or to prevent or mitigate tissue and/or cellular damage in a subject. A "therapeutically effective amount" mitigates neurodegeneration by about 20%, preferably by about 40%, more preferably by about 60%, and still more preferably by about 80%, relative to untreated subjects. The ability of a compound of structural formula (I) and (II) to mitigate neurodegeneration can be evaluated in model systems predictive of efficacy in mitigating neurodegeneration in human diseases, such as animal model systems known in the art (e.g., the method of transient middle cerebral artery occlusion in the rat) or by in vitro methods, (e.g., the assays described herein).

The ability of a compound of structural formula (I) or (II) to mitigate neurodegeneration can be evaluated by observation of one or more symptoms or signs associated with neurodegeneration in vivo. For example, the ability of a compound of structural formula (I) or (II) to mitigate neurodegeneration can be associated with an observable improvement in a clinical manifestation of the underlying neurodegeneration-related disease or condition, or a slowing or delay in progression of symptoms of the condition. Thus, monitoring of clinical manifestations of disease can be useful in evaluating the neurodegeneration-mitigating efficacy of a compound of the invention.

Toxicity and therapeutic efficacy of a compound of structural formula (I) or (II) can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds that exhibit high therapeutic indices are preferred. The data obtained from such data can be used in formulating a dosage range for use in humans and other mammals. The dosage preferably lies within a range of circulating compound concentrations that include the $ED_{50}$ with little or no toxicity. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a present compound required for use in therapy varies with the nature of the disease or condition being treated, the length of time that activity is desired, and the age and the condition of the patient, and ultimately is determined by the attendant physician. Dosage amounts and intervals can be adjusted individually to provide plasma levels of the compound that are sufficient to maintain the desired therapeutic effects. The desired dose conveniently can be administered in a single dose, or as multiple doses administered at appropriate intervals, for example as one, two, three, four or more subdoses per day. For example, a present compound can be administered at a frequency of: four doses delivered as one dose per day at four-day intervals (q4d×4); four doses delivered as one close per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

The dosage of a composition containing a compound of structural formula (I) or (II), can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, 10 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, or 200 mg/kg. The above dosages are exemplary of the average case, but there can be individual instances in which higher or lower dosages are merited, and such are within the scope of this invention. In practice, the physician determines the actual dosing regimen that is most suitable for an individual patient, which can vary with the age, weight, and response of the particular patient.

A compound of structural formula (I) or (II) used in a method of the present invention can be administered in an amount of about 0.005 to about 200 milligrams per dose, about 0.05 to about 150 milligrams per dose, or about 0.5 to about 100 milligrams per dose. For example, a present compound, can be administered, per dose, in an amount of about 0.005, 0.05, 0.5, 5, 10, 20, 25, 30, 40, 50, 60, 70, 80, 100, 150, or 200 milligrams, including all doses between 0.005 and 200 milligrams.

The compound typically are administered in admixture with a pharmaceutical carrier selected with regard to the intended route of administration and standard pharmaceutical practice. Pharmaceutical compositions for use in accordance with the present invention are formulated in a conventional manner using one or more physiologically acceptable carriers comprising excipients and auxiliaries that facilitate processing of present compounds.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of a present compound is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a compound of structural formula (I) or (II). When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a compound of structural formula (I) or (II).

When a therapeutically effective amount of a compound of structural formula (I) or (II) is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle. A present compound can be infused with other fluids over a 10-30 minute span or over several hours.

A present compound can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding a present compound to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

Prevention of the action of microorganisms can be achieved by various antibacterial and antifungal agents, for example, parabens, chlorobutanol, phenol, ascorbic acid, thimerosal, and the like. In some cases, it is preferable to include isotonic agents, for example, sugars, sodium chloride, or polyalcohols, such as mannitol and sorbitol, in the composition. Prolonged absorption of the injectable compositions can be achieved by including an agent that delays absorption, for example, aluminum monostearate or gelatin.

A compound of structural formula (I) or (II) can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

It is advantageous to formulate parenteral compositions in a unit dosage form for ease of administration and uniformity of dosage. "Unit dosage form" as used herein refers to physically discrete units suited as unitary dosages for the subjects to be treated. Each dose unit contains a predetermined quantity of a present compound calculated to produce the desired therapeutic effect in association with the required pharmaceutical vehicle. The dosage unit forms are dictated by and are directly dependent on (a) the unique characteristics of the compound of structural formula (I) or (II) and (b) the particular therapeutic effect to be achieved.

Pharmaceutical compositions for parenteral administration include aqueous solutions of the active agent in water soluble form. Additionally, suspensions of a compound of structural formula (I) or (II) can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

A compound of structural formula (I) or (II) also can be formulated in rectal compositions, such as suppositories or retention enemas, e.g., containing conventional suppository bases. In addition to the formulations described previously, a present compound also can be formulated as a depot preparation. Such long-acting formulations can be administered by implantation (for example, subcutaneously or intramuscularly) or by intramuscular injection. Thus, for example, a compound can be formulated with suitable polymeric or hydrophobic materials example, as an emulsion in an acceptable oil) or ion exchange resins.

In particular, a compound can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. A present compound also can be injected parenterally, for example, intravenously, intramuscularly, subcutaneously, or intracoronarily. For parenteral administration, a present compound is best used in the form of a sterile aqueous solution which can contain other substances, for example, salts or monosaccharides, such as mannitol or glucose, to make the solution isotonic with blood.

As an additional embodiment, the present invention includes kits which comprise one or more compound of structural formula (I) or (II), or a composition containing the same, packaged in a manner that facilitates their use to practice methods of the invention. In one embodiment, the kit includes a present compound or composition containing the same as useful for practice of a method, packaged in a container, such as a sealed bottle or vessel, with a label affixed to the container or included in the kit that describes use of the compound or composition to practice the method of the invention. Preferably, the compound or composition is packaged in a unit dosage form. The kit further can include a device suitable for administering the composition according to the intended route of administration.

The present invention employed ex vivo or in vitro. For example, studies utilizing tissue homogenates according to the invention. Furthermore, diagnostic tests or studies of efficacy of selected compounds may be performed ex vivo or in vitro, including in animal models. Such tests, studies and assays are within the scope of the invention.

REFERENCES

K. Abe et al., *Eur. J. Pharmacol.* 347 (1998) 145-152.
O. Arancio et al., *Nature* 376 (1995) 74-80.
S. W. Barger et al., *J. Neurochem.* 64 (1995) 2087-2096.
S. M. Berge et al., *J. Pharm. Sci.* 66 (1977) 1-19.
R. Bernabeu et al., *NeuroReport* 8 (1997) 2221-2224.
R. Bernabeu et al., *NeuroReport* 7 (1996) 585-588.
P. G. Bloe et al., *FEBS Lett.* 357 (1995) 140.
P. Briscoe et al., *Am. J. Physiol.* 1233 (1995) 134.
R. Bullock et al., *J. Neurosurg.* 89 (1998) 507-518.
P. H. Chan et al., *J. Neurosci.* 18 (1998) 8292-8299.
J. Chen et al., *J. Neurosci.* 18 (1998) 4914-4928.
G. M. Cohen et al., *Biochem. J.* 326 (1997) 1-16.
Y. Du et al., *Proc. Natl. Acad. Sci. USA* 94 (1997) 11657-11662.
M. Endres et al., *J. Cereb. Blood Flow Metab.* 18 (1998) 238-247.
A. G. Estevez et al., *J. Neurosci.* 18 (1998) 3708-3714.
S. E. Farinelli et al., *J. Neurosci.* 16 (1996) 23-25-2334.
K. Furukawa et al., *Nature* 379 (1996) 74-78.
P. Gaetani et al., *J. Neurosurg.* 89 (1998) 748-754.
H. Goda et al., *Eur. I Pharmacol.* 357 (1998) 149-155.
F. J. Gottron et al., *Mol. Cell. Neurosci.* 9 (1997) 159-169.
R. Haviv et al., *J. Neurosci. Res.* 50 (1997) 69-80.
F. P. Huang et al., *Neurochem. Res.* 23 (1998) 991-996.
D. Ibarrola et al., *Eur. J. Pharmacol.* 352 (1998) 29-35.
Y. M. Kim et al., *J. Biol. Chem.* 272 (1997) 31138-31148.
R. Louw et al., *J. Chem. Soc., Chem. Comm.* (1976) 496-497
R. L. Macdonald et al., *Neurol. Med. Chir.* (Tokyo) 38 (1998) 1-11.
A. Mizuno et al., *Gen. Pharmacol.* 30 (1998) 575-578.
B. A. Morgan et al., In Ann. Rep. Med. Chem. (Virick F. J., et al.) (1989) pp. 243-253, Academic Press, San Diego, Calif.
S. Namura et al., *J. Neurosci.* 18 (1998) 3659-3668.
B. Ni et al., *J. Cereb. Blood Flow Metab.* 18 (1998) 248-256.
D. W. Nicholson et al., *Trends Biochem. Sci.* 22 (1997) 299-306.
M. J. O'Neill et al., *Neuropharmacol.* 37 (1998) 1211-1222.
R. J. Onellette et al., *J. Org. Chem.* 41 (1976) 2782-2783.
M. Owais et al., *Antimicrob. Agents Chemother.* 39 (1995) 180.
M. Pall ares et al., *Neurosci.* 87 (1998) 551-558.
V. V. Ranade et al., *J. Clin. Pharmacol.* 29 (1989) 685.
G. H. Strejan et al., *J. Neuroimmunol.* 7 (1984) 27.
M. Tagami et al., *Lab. Invest.* 78 (1998) 1415-1429.
K. Umemura et al., *Brain Res.* 773 (1997) 61-65.
F. Umezawa et al., *Biochem. Biophys. Res. Commun.* 153 (1988) 1038.
P. G. Venault et al., *J., Encephale,* 18 (1992) 655.
J. Wu et al., *J. Neurosci.* 18 (1998) 3589-3596.
K. Yang et al., *J. Chem. Soc., Perkin Trans.* 1 (1996) 1073-1075.
Y. L. Yang et al., *Brain Res.* 795 (1998) 121-127.

-continued
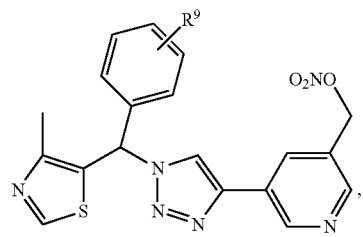
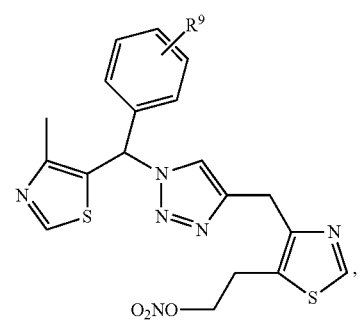
wherein R⁹ is defined as above;
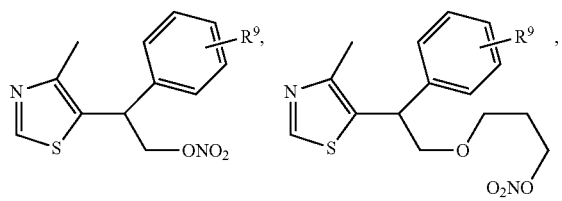
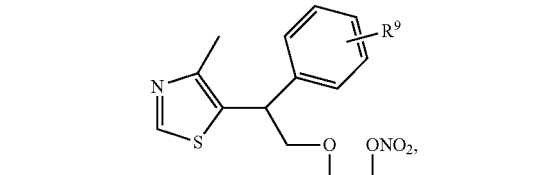
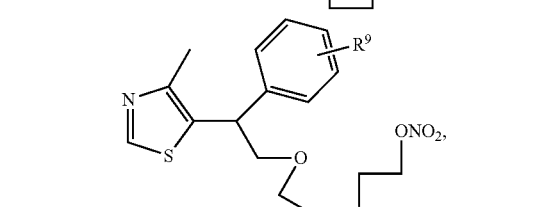
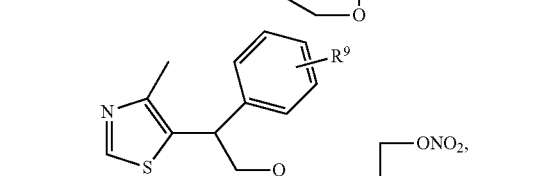
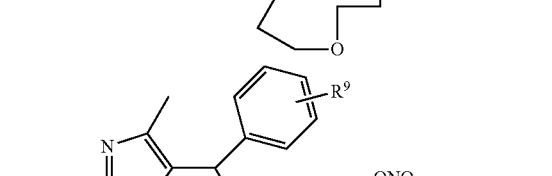
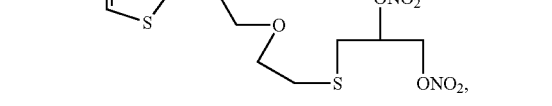
-continued
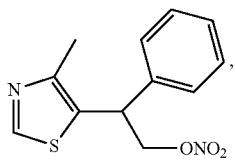
wherein R⁹ is defined as above.
5. The compound of claim 4 wherein R⁹ is selected from the group consisting of F, Cl, Br, Me, OMe, NO₂, CO₂Et, CO₂H, CO₂Me, CONH₂, CO(CH)₂NEt₂, and H.
6. The compound of claim 1 selected from the group consisting of
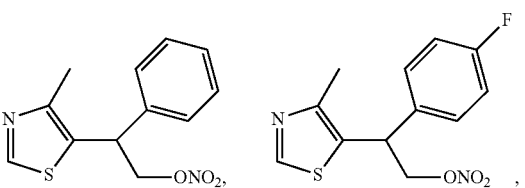
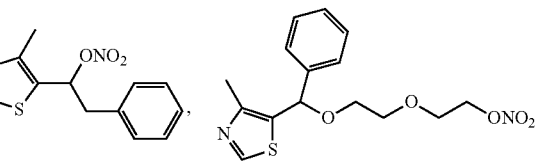
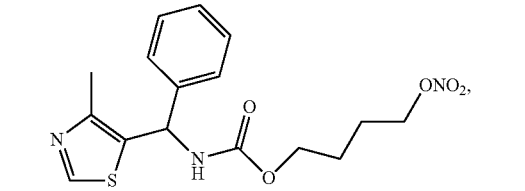
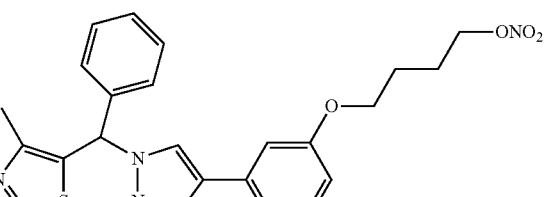
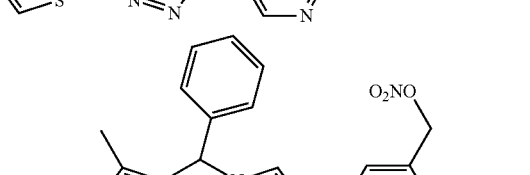
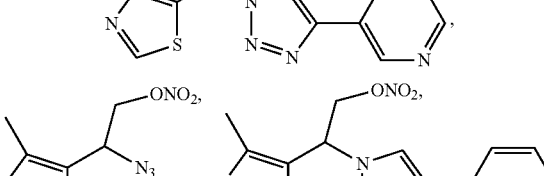
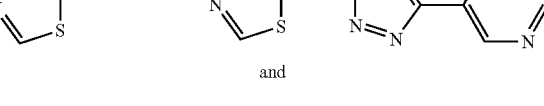
and -continued
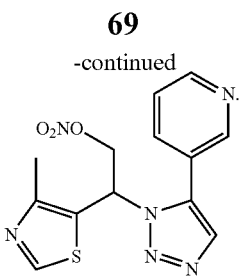
7. The compound of claim 1 having a structure
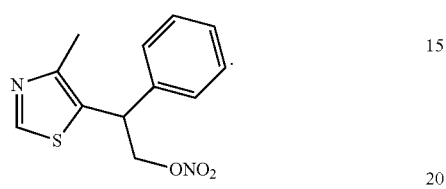

The invention claimed is:
1. A compound having a structure

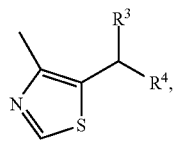

wherein $R^3$ is selected from the group consisting of substituted or unsubstituted aryl, substituted or unsubstituted heteroaryl, an unsubstituted $C_{1-24}$ aliphatic group, —$N_3$, —$(CH_2)_{1-3}$aryl, and —$(CH_2)_{1-3}$heteroaryl;
$R^4$ is selected from the group consisting of $ONO_2$, —$(CH_2)_{1-3}ONO_2$, —$NHC(=O)O(CH_2)_{1-6}ONO_2$, —$NHC(=O)C(R^a)(R^b)CH_2ONO_2$, —$NHC(=O)CH_2C(R^a)(R^b)ONO_2$, —$NHC(=O)YC(R^a)(R^b)CH_2ONO_2$, —$NHC(=O)YCH_2C(R^a)(R^b)ONO_2$, —$OC(=O)CH_2C(R^a)(R^b)ONO_2$, —$OC(=O)C(R^a)(R^b)CH_2ONO_2$, —$O(CH_2)_{1-3}ONO_2$, —$O(CH_2)_{1-2}O(CH_2)_{1-2}ONO_2$, —$O(CH_2)_{1-3}YCH_2$—[$CH(ONO_2)$]$_n$—$(CH_2)_{1-2}ONO_2$, and heteroaryl having at least one aliphatic nitro substituent;
$R^a$ and $R^b$, independently, are selected from the group consisting of H, $C_{1-3}$alkyl, aryl, and heteroaryl;
n is an integer of 1 through 5; and
Y is O, S, or NH;
or a pharmaceutically acceptable salt, prodrug, or hydrate thereof.
2. The compound of claim 1 wherein $R^3$ is phenyl, optionally substituted with one or more of halo, benzyl, $N_3$, or triazolyl optionally substituted with pyridinyl.
3. The compound of claim 1 wherein $R^4$ is selected from the group consisting of —$ONO_2$, —$CH_2ONO_2$, —$O(CH_2)_2O(CH_2)_2ONO_2$, —$O(CH_2)_4ONO_2$,

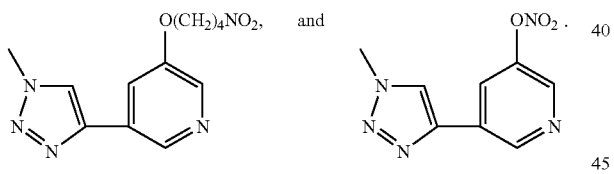

4. The compound of claim 1 selected from the group consisting of

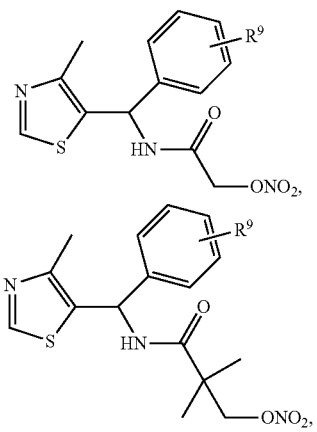

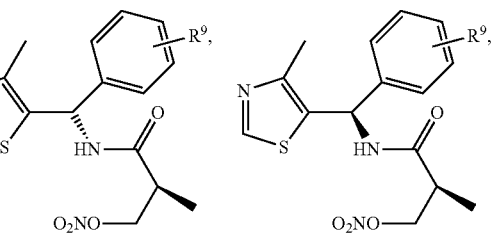

wherein $R^9$ is selected from the group consisting of halo, $C_{1-3}$alkyl, $OR^a$, wherein $R^a$ is H or $C_{1-3}$alkyl, $NO_2$, $CO_2R^a$, $CONR^a_2$, and $CO(CH_2)_{1-3}NR^a_2$, and H;

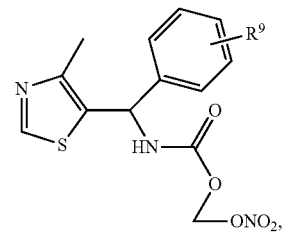

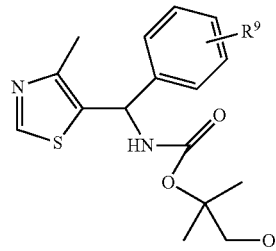

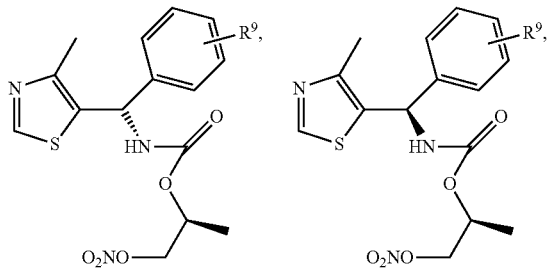

wherein $R^9$ is defined as above;

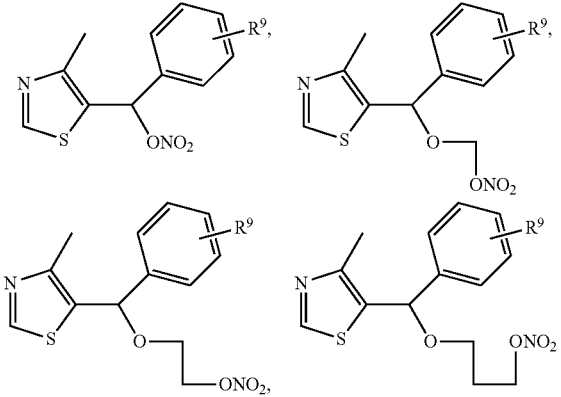

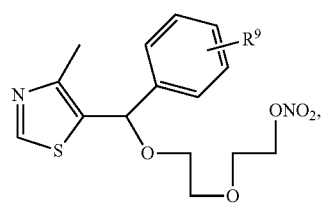
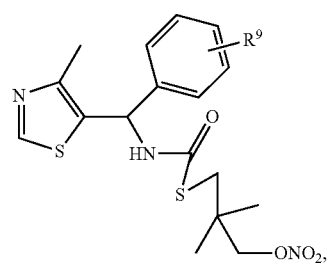
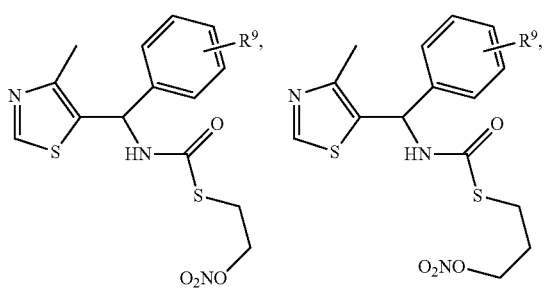
wherein $R^9$ is defined as above;
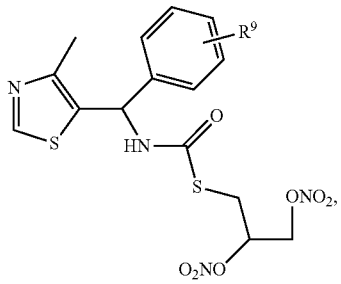
wherein $R^9$ is defined as above; and
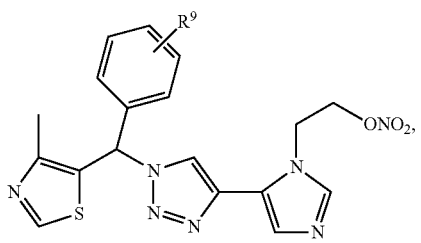
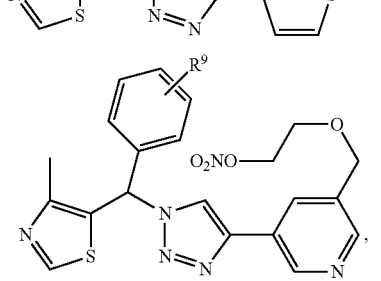
wherein $R^9$ is defined as above;